US009821050B2

(12) United States Patent
De Silva et al.

(10) Patent No.: US 9,821,050 B2
(45) Date of Patent: Nov. 21, 2017

(54) CHIMERIC DENGUE VIRUS E GLYCOPROTEINS COMPRISING MUTANT DOMAIN I AND DOMAIN II HINGE REGIONS

(71) Applicants: The University of North Carolina at Chapel Hill, Chapel Hill, NC (US); Vanderbilt University, Nashville, TN (US)

(72) Inventors: Aravinda M. De Silva, Chapel Hill, NC (US); A. Ruklanthi De Alwis, Dehiwala (LK); Wahala M. P. B. Wahala, Chapel Hill, NC (US); Ralph S. Baric, Haw River, NC (US); William B. Messer, Portland, OR (US); James E. Crowe, Jr., Nashville, TN (US); Scott A. Smith, Nashville, TN (US)

(73) Assignees: The University of North Carolina at Chapel Hill, Chapel Hill, NC (US); Vanderbilt University, Nashville, TN (US)

( * ) Notice: Subject to any disclaimer, the term of this patent is extended or adjusted under 35 U.S.C. 154(b) by 98 days.

(21) Appl. No.: 14/390,312

(22) PCT Filed: Mar. 15, 2013

(86) PCT No.: PCT/US2013/032367
§ 371 (c)(1),
(2) Date: Oct. 2, 2014

(87) PCT Pub. No.: WO2013/151764
PCT Pub. Date: Oct. 10, 2013

(65) Prior Publication Data
US 2015/0328303 A1    Nov. 19, 2015

Related U.S. Application Data

(60) Provisional application No. 61/619,247, filed on Apr. 2, 2012.

(51) Int. Cl.
*A61K 39/12* (2006.01)
*G01N 33/569* (2006.01)
*C12N 7/00* (2006.01)
*C07K 14/005* (2006.01)
*A61K 39/00* (2006.01)

(52) U.S. Cl.
CPC ............ *A61K 39/12* (2013.01); *C07K 14/005* (2013.01); *C12N 7/00* (2013.01); *G01N 33/56983* (2013.01); *A61K 2039/70* (2013.01); *C07K 2319/00* (2013.01); *C12N 2770/24023* (2013.01); *C12N 2770/24122* (2013.01); *C12N 2770/24123* (2013.01); *C12N 2770/24134* (2013.01); *G01N 2333/185* (2013.01); *G01N 2469/20* (2013.01)

(58) Field of Classification Search
CPC ..................... A61K 39/12; C12N 7/00; C12N 2770/24122; C12N 2770/24134; C07K 14/005
See application file for complete search history.

(56) References Cited

U.S. PATENT DOCUMENTS

| 4,501,729 A | 2/1985 | Boucher et al. |
| 4,708,871 A | 11/1987 | Geysen |
| 7,862,829 B2 | 1/2011 | Johnston et al. |
| 2005/0002968 A1 | 1/2005 | Monath et al. |
| 2008/0193477 A1 | 8/2008 | Monath et al. |

FOREIGN PATENT DOCUMENTS

| WO | WO 94/00153 A1 | 1/1994 |
| WO | WO 95/17210 A1 | 6/1995 |
| WO | WO 2012/082073 A1 | 6/2012 |

OTHER PUBLICATIONS

Dubey, K. D., et al., 2011, Role of pH on dimeric interactions for DENV envelope protein: An insight from molecular dynamics study, Biochimica et Biophysica Acta 1814:1796-1801.*
Butrapet, S., et al., 2011, Amino acid changes within the E protein hinge region that affect dengue virus type 2 infectivity and fusion, Virol. 413:118-127.*
Teoh, E. P., et al., 2012, The structural basis for serotype-specific neutralization of dengue virus by a human antibody, Sci. Translational Med. 4(139):1-9.*
Lee et al., 1997, Changes in the dengue virus major envelope protein on passaging and their localization on the three-dimensional structure of the protein, Virol. 232:281-290.*
Thomas, S. J., 2011, The necessity and quandaries of dengue vaccine development, J. Infect. Dis. 203:299-303.*
Rothman, A. L., 2011, Immunity to dengue virus: a tale of original antigenic sin and tropical cytokine storms, Nat. Rev. Immunol. 11:532-543.*
Stephenson, J. R., 2005, Understanding dengue pathogenesis: implications for vaccine design, Bull. WHO 83(4):308-314.*
Beltramello et al. "The Human Immune Response to Dengue Virus Is Dominated by Highly Cross-Reactive Antibodies Endowed with Neutralizing and Enhancing Activity" *Cell Host & Microbe* 8(3):1-25 (2010).

(Continued)

*Primary Examiner* — Jeffrey Parkin
(74) *Attorney, Agent, or Firm* — Myers Bigel, P.A.

(57) ABSTRACT

The present invention provides compositions and methods of use comprising a chimeric dengue virus E glycoprotein comprising a dengue virus E glycoprotein backbone, which comprises amino acid substitutions that introduce a dengue virus E glycoprotein domain I and domain II hinge region from a dengue virus serotype that is different from the dengue virus serotype of the dengue virus E glycoprotein backbone.

24 Claims, 13 Drawing Sheets

(56) References Cited

OTHER PUBLICATIONS

Brien et al. "Genotype-Specific Neutralization and Protection by Antibodies against Dengue Virus Type 3" *Journal of Virology* 84(20):10630-10643 (2010).
Coller et al. "The Development of Recombinant Subunit Envelope-Based Vaccines to Protect Against Dengue Virus Induced Disease" *Vaccine* 29(42):7267-7275 (2011).
De Alwis et al. "In-Depth Analysis of the Antibody Response of Individuals Exposed to Primary Dengue Virus Infection" *PLoS Neglected Tropical Diseases* 5(6):e1188 (2011).
De Alwis et al. "Identification of human neutralizing antibodies that bind to complex epitopes on dengue virions" *Proceedings of the National Academy of Sciences* 109(19):7439-7444 (2012).
Debbink et al. "Genetic Mapping of a Highly Variable Norovirus GII.4 Blockade Epitope: Potential Role in Escape from Human Herd Immunity" *Journal of Virology* 86(2):1214-1226 (2012).
Dejnirattisai et al. "Cross-Reacting Antibodies Enhance Dengue Virus Infection in Humans" *Science* 328:745-748 (2010).
Dejnirattisai et al. "Enhancing cross-reactive anti-prM dominates the human antibody response in dengue infection" *Science* 328(5979):1-12 (2010).
Dias et al. "A Shared Structural Solution for Neutralizing Ebolaviruses" *Natural Structural & Molecular Biology* 18(12):1424-1427 (2012).
GenBank Accession No. DQ211652.1 "West Nile virus strain NY99, complete genome" *NCBI* 5 pages (Jun. 7, 2006).
GenBank Accession No. JQ411814 "Dengue virus 3 isolate UNC3001, complete genome" *NCBI* 5 pages (Apr. 30, 2012).
GenBank Accession No. JX503529 "Yellow fever virus strain YF/Vaccine/USA/Sanofi-Pasteur-17D-204/UF795AA/YFVax, complete genome" *NCBI* 5 pages (Sep. 16, 2012).
GenBank Accession No. NC_001474.2 "Dengue virus 2, complete genome" *NCBI* 6 pages (Nov. 17, 2011).
GenBank Accession No. U14163.1 "Japanese encephalitis virus SA14 polyprotein mRNA, complete cds" *NCBI* 5 pages (Sep. 13, 1994).
GenBank Accession No. U88535.1 "Dengue virus type 1 clone WestPac, complete genome" *NCBI* 5 pages (Sep. 19, 1997).
Geysen et al. "Use of peptide synthesis to probe viral antigens for epitopes to a resolution of a single amino acid" *Proceedings of the National Academy of Sciences* 81:3998-4002 (1984).
Geysen et al. "A Priori Delineation of a Peptide Which Mimics a Discontinuous Antigenic Determinant" *Molecular Immunology* 23(7):709-715 (1986).
Goncalvez et al. "Humanized Monoclonal Antibodies Derived from Chimpanzee Fabs Protect against Japanese Encephalitis Virus In Vitro and In Vivo" *Journal of Virology* 82(14):7009-7021 (2008).
Gromowski et al. "Characterization of an antigenic site that contains a dominant, type-specific neutralization determinant on the envelope protein domain III (ED3) of dengue 2 virus" *Virology* 366:349-360 (2007).
Gromowski et al. "Mutations of an antibody binding energy hot spot on domain III of the dengue 2 envelope glycoprotein exploited for neutralization escape" *Virology* 407:237-246 (2010).
Hopp et al. "Prediction of protein antigenic determinants from amino acid sequences" *Proceedings of the National Academy of Sciences* 78(6):3824-3828 (1981).
Imrie et al. "Antibody to Dengue 1 Detected More Than 60 Years after Infection" *Viral Immunology* 20(4):672-675 (2007).
International Preliminary Report on Patentability corresponding to International Patent Application No. PCT/US2013/032367:11 pages (dated Oct. 7, 2014).
International Search Report and the Written Opinion of the International Searching Authority corresponding to International Patent Application No. PCT/US2013/032367:14 pages (dated Jun. 28, 2013).
Kaufmann et al. "Neutralization of West Nile virus by cross-linking of its surface proteins with Fab fragments of the human monoclonal antibody CR4354" *Proceedings of the National Academy of Sciences* 107(44):18950-18955 (2010).
Kraus et al. "Comparison of Plaque- and Flow Cytometry-Based Methods for Measuring Dengue Virus Neutralization" *Journal of Clinical Microbiology* 45(11):3777-3780 (2007).
Kuhn et al. "Structure of Dengue Virus: Implications for Flavivirus Organization, Maturation, and Fusion" *Cell* 108:717-725 (2002).
Kyte et al. "A Simple Method for Displaying the Hydropathic Character of a Protein" *Journal of Molecular Biology* 157:105-132 (1982).
Li et al. "The Flavivirus Precursor Membrane-Envelope Protein Complex: Structure and Maturation" *Science* 319:1830-1834 (2008).
Lin et al. "Analysis of Epitopes on Dengue Virus Envelope Protein Recognized by Monoclonal Antibodies and Polyclonal Human Sera by a High Throughput Assay" *PLoS Neglected Tropical Diseases* 6(1):e1447 (2012).
Lindesmith et al. "Immunogenetic Mechanisms Driving Norovirus GII.4 Antigenic Variation" *PLoS Pathogens* 8(5):e1002705 (2012).
Lindesmith et al. "Monoclonal Antibody-Based Antigenic Mapping of Norovirus GII.4 2002" *Journal of Virology* 86(2):873-883 (2012).
Lok et al. "Binding of a neutralizing antibody to dengue virus alters the arrangement of surface glycoproteins" *Nature Structural & Molecular Biology* 15(3):312-317 (2008).
Mackenzie et al. "Emerging flaviviruses: the spread and resurgence of Japanese encephalitis, West Nile and dengue viruses" *Nature Medicine* 10(12):S98-S109 (2004).
McMinn et al. "Murray Valley Encephalitis Virus Envelope Protein Antigenic Variants with Altered Hemagglutination Properties and Reduced Neuroinvasiveness in Mice" *Virology* 211:10-20 (1995).
Meloen et al. "Mimotopes: realization of an unlikely concept" *Journal of Molecular Recognition* 13:352-359 (2000).
Messer et al. "Development and Characterization of a Reverse Genetic System for Studying Dengue Virus Serotype 3 Strain Variation and Neutralization" *PLoS Neglected Tropical Diseases* 6(2):e1486 (2012).
Modis et al. "A ligand-binding pocket in the dengue virus envelope glycoprotein" *Proceedings of the National Academy of Sciences* 100(12):6986-6991 (2003).
Modis et al. "Variable Surface Epitopes in the Crystal Structure of Dengue Virus Type 3 Envelope Glycoprotein" *Journal of Virology* 79(2):1223-1231 (2005).
Nybakken et al. "Structural basis of West Nile virus neutralization by a therapeutic antibody" *Nature* 437:764-768 (2005).
Nybakken et al. "Crystal Structure of the West Nile Virus Envelope Glycoprotein" *Journal of Virology* 80(23):11467-11474 (2006).
Oliphant et al. "Antibody Recognition and Neutralization Determinants on Domains I and II of West Nile Virus Envelope Protein" *Journal of Virology* 80(24):12149-12159 (2006).
Oliphant et al. "Induction of Epitope-Specific Neutralizing Antibodies against West Nile Virus" *Journal of Virology* 81(21):11828-11839 (2007).
Rey et al. "The envelope glycoprotein from tick-borne encephalitis virus at 2 Å resolution" *Nature* 375:291-298 (1995).
Sanchez et al. "The neutralizing antibody response against West Nile virus in naturally infected horses" *Virology* 359:336-348 (2007).
Shrestha et al. "The Development of Therapeutic Antibodies That Neutralize Homologous and Heterologous Genotypes of Dengue Virus Type 1" *PLoS Pathogens* 6(4):e1000823 (2010).
Smith et al. "Persistence of Circulating Memory B Cell Clones with Potential for Dengue Virus Disease Enhancement for Decades following Infection" *Journal of Virology* 86(5):2665-2675 (2012).
Spurrier et al. "Structural Analysis of Human and Macaque Monoclonal Antibodies 2909 and 2.5B: Implications for the Configuration of the Quaternary Neutralizing Epitope of HIV-1 gp120" *Structure* 19(5):691-699 (2011).
Sukupolvi-Petty et al. "Type- and Subcomplex-Specific Neutralizing Antibodies against Domain III of Dengue Virus Type 2 Envelope Protein Recognize Adjacent Epitopes" *Journal of Virology* 81(23):12816-12826 (2007).
Sukupolvi-Petty et al. "Structure and Function Analysis of Therapeutic Monoclonal Antibodies against Dengue Virus Type 2" *Journal of Virology* 84(18):9227-9239 (2010).

(56) References Cited

OTHER PUBLICATIONS

Valdes et al. "The Chimeric Protein Domain III-Capsid of Dengue Virus Serotype 2 (DEN-2) Successfully Boosts Neutralizing Antibodies Generated in Monkeys upon Infection with DEN-2" *Clinical and Vaccine Immunology* 18(3):455-459 (2011).
Vogt et al. "Human Monoclonal Antibodies against West Nile Virus Induced by Natural Infection Neutralize at a Postattachment Step" *Journal of Virology* 83(13):6494-6507 (2009).
Wahala et al. "Dengue virus neutralization by human immune sera: Role of envelope protein domain III-reactive antibody" *Virology* 392:103-113 (2009).
Wahala et al. "Natural Strain Variation and Antibody Neutralization of Dengue Serotype 3 Viruses" *PLoS Pathogens* 6(3):e1000821 (2010).
Wahala et al. "Recombinant Dengue Type 2 Viruses with Altered E Protein Domain III Epitopes Are Efficiently Neutralized by Human Immune Sera" *Journal of Virology* 86(7):4019-4023 (2012).
Yu et al. "An optimized electrofusion-based protocol for generating virus-specific human monoclonal antibodies" *Journal of Immunological Methods* 336(2):142-151 (2008).
Zhang et al. "Visualization of membrane protein domains by cryo-electron microscopy of dengue virus" *Nature Structural Biology* 10(11):907-912 (2003).
Azevedo et al. "DNA Vaccines against Dengue Virus Type 2 Based on Truncate Envelope Protein or It's Domain III" *PLoS One* 6(7):e20528 (2011).
Bielefeldt-Ohmann et al. "Analysis of a recombinant dengue-2 virus-dengue-3 virus hybrid envelope protein expressed in a secretory baculovirus system" *Journal of General Virology* 78:2723-2733 (1997).
Butrapet et al. "Amino acid changes within the E protein hinge region that affect dengue virus type 2 infectivity and fusion" *Virology* 413:118-127 (2011).
Chambers et al. "Yellow Fever Virus/Dengue-2 Virus and Yellow Fever Virus/Dengue-4 Virus Chimeras: Biological Characterization, Immunogenicity, and Protection against Dengue Encephalitis in the Mouse Model" *Journal of Virology* 77(6):3655-3668 (2003).
Crill et al. "Localization and Characterization of Flavivirus Envelope Glycoprotein Cross-Reactive Epitopes" *Journal of Virology* 78(24):13975-13986 (2004).
Extended European Search Report corresponding to European Patent Application No. 13772201.3 (16 pages) (dated Sep. 15, 2015).
Guirakhoo et al. "Recombinant Chimeric Yellow Fever-Dengue Type 2 Virus Is Immunogenic and Protective in Nonhuman Primates" *Journal of Virology* 74(12):5477-5485 (2000).
Guirakhoo et al. "Construction, Safety, and Immunogenicity in Nonhuman Primates of a Chimeric Yellow Fever-Dengue Virus Tetravalent Vaccine" *Journal of Virology* 75(16):7290-7341 (2001).
Konishi et al. "Dengue type 2 virus subviral extracellular particles produced by a stably transfected mammalian cell line and their evaluation for a subunit vaccine" *Vaccine* 20:1058-1067 (2002).
Rajamanonmani et al. "On a mouse monoclonal antibody that neutralizes all four dengue virus serotypes" *Journal of General Virology* 90:799-809 (2009).

\* cited by examiner

G

|  | DI | DII | DII | DI |
|---|---|---|---|---|
|  | 44 | 55 | 268 | 285 |
| DENV1 (WP 71) | ELLKTEVTNPAV | (SEQ ID NO:1) | TEIQ-TSG-TTTIFAGHLKC | (SEQ ID NO:5) |
| DENV2 (S16803) | ELIKTEAKQPAT | (SEQ ID NO:2) | TEIQ-MSS-GNLLFTGHLKC | (SEQ ID NO:6) |
| DENV3 (Thai 95) | ELQKTEATQLAT | (SEQ ID NO:3) | TEIQ^NSG-GTSIFAGHLKC | (SEQ ID NO:7) |
| WNV (NY2000) | KMMNMEAANLAE | (SEQ ID NO:4) | IPVE-FSSNTVKLTSGHLKC | (SEQ ID NO:8) |

|  | DIII |  |  |  |
|---|---|---|---|---|
|  | 317 | 327 | 356 | 364 |
| DENV1 (WP 71) | HGTVLVQVKYE | (SEQ ID NO:9) | PIVTDKEK---P | (SEQ ID NO:13) |
| DENV2 (S16803) | HGTIVIRVQYE | (SEQ ID NO:10) | PIVTEKDS---P | (SEQ ID NO:14) |
| DENV3 (Thai 95) | HGTILIKVEYK | (SEQ ID NO:11) | PVVTKKEE---P | (SEQ ID NO:15) |
| WNV (NY2000) | HGTVVLELQYT | (SEQ ID NO:12) | PFVSVATANAK | (SEQ ID NO:16) |

H

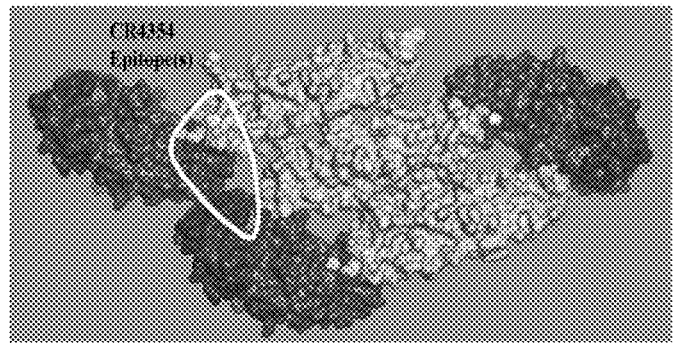

FIG. 3 (Cont'd.)

```
Alignment of DENV1-4, YFV and JEV glycoprotein amino acid sequences
             1                                                  50
DENV3_E_AA#2 MRCVGIGNRD FVEGLSGATW VDVVLEHGGC VTTMAKNKPT LDIELQKTEA 50
  DENV1_E_AA MRCVGIGNRD FVEGLSGATW VDVVLEHGSC VTTMAKDKPT LDIELLKTEV 50
  DENV4_E_AA MRCVGVGNRD FVEGVSGGAW VDLVLEHGGC VTTMAQGKPT LDFELTKTTA 50
  DENV_2_E_AA MRCIGISNRD FVEGVSGGSW VDIVLEHGSC VTTMAKNKPT LDFELIKTEA 50
       YF_17D AHCIGITDRD FIEGVHGGTW VSATLEQDKC VTVMAPDKPS LDISLETVAI 50
       JESA14 FNCLGMGNRD FIEGASGATW VDLVLEGDSC LTIMANDKPT LDVRMINIEA 50

51                                                 100
DENV3_E_AA#2 TQLATLRKLC IEGKITNITT DSRCPTQGEA VLPEEQDQNY VCKHTYVDRG 100
  DENV1_E_AA TNPAVLRKLC IEAKISNTTT DSRCPTQGEA TLVEEQDTNF VCRRTFVDRG 100
  DENV4_E_AA KEVALLRTYC IEASISNITT ATRCPTQGEP YLKEEQDQQY ICRRDVVDRG 100
  DENV_2_E_AA KQPATLRKYC IEAKLTNTTT ESRCPTQGEP SLNEEQDKRF VCKHSMVDRG 100
       YF_17D DRPAEVRKVC YNAVLTHVKI NDKCPSTGEA HLAEENEGDN ACKRTYSDRG 100
       JESA14 SQLAEVRSYC YHASVTDIST VARCPTTGEA HNEKRADSSY VCKQGFTDRG 100

101                                                150
DENV3_E_AA#2 WGNGCGLFGK GSLVTCAKFQ CLEPIEGKVV QYENLKYTVI ITVHTGDQHQ 150
  DENV1_E_AA WGNGCGLFGK GSLITCAKFK CVTKLEGKIV QYENLKYSVI VTVHTGDQHQ 150
  DENV4_E_AA WGNGCGLFGK GGVVTCAKFS CSGKITGNLV QIENLEYTVV VTVHNGDTHA 150
  DENV_2_E_AA WGNGCGLFGK GGIVTCAMFT CKKNMEGKVV QPENLEYTIV VTPHSGEEHA 150
       YF_17D WGNGCGLFGK GSIVACAKFT CAKSMSLFEV DQTKIQYVIR AQLHVGAKQE 150
       JESA14 WGNGCGLFGK GSIDTCAKFS CTSKAIGRTI QPENIKYEVG IFVHGTTTSE 150

151                                                200
DENV3_E_AA#2 VGNET..... ..QGVTAEIT PQASTTEAIL PEYGTLGLEC SPRTGLDFNE 193
  DENV1_E_AA VGNETTE... ..HGTTATIT PQAPTSEIQL TDYGALTLDC SPRTGLDFNE 195
  DENV4_E_AA VGNDTSN... ..HGVTATIT PRSPSVEVKL PDYGELTLDC EPRSGIDFNE 195
  DENV_2_E_AA VGNDTGK... ..HGKEIKVT PQSSITEAEL TGYGTVTMEC SPRTGLDFNE 195
       YF_17D NWTTDI.... ....KTLKFD ALSGSQEVEF IGYGKATLEC QVQTAVDFGN 192
       JESA14 NHGNYSAQVG ASQAAKFTVT PNAPSITLKL GDYGEVTLDC EPRSGLNTEA 200

201                                                250
DENV3_E_AA#2 MILLTMKNKA WMVHRQWFFD LPLPWTSGAT TETPTWNRKE LLVTFKNAHA 243
  DENV1_E_AA MVLLTMEKKS WLVHKQWFLD LPLPWTSGAS TSQETWNRQD LLVTFKTAHA 245
  DENV4_E_AA MILMRMKKKT WLVHKQWFLD LPLPWTAGAD TSEVHWNYKE RMVTFKVPHA 245
  DENV_2_E_AA MVLLQMENKA WLVHRQWFLD LPLPWLPGAD TQGSNWIQKE TLVTFKNPHA 245
       YF_17D SYIAEMETES WIVDRQWAQD LTLPWQSG.. .SGGVWREMH HLVEFEPPHA 239
       JESA14 FYVMTVGSKS FLVHREWFHD LALPWTSP.. .SSTAWRNRE LLMEFEEAHA 247
```

*FIG. 11*

```
            251                                                    300
DENV3_E_AA#2    KKQEVVVLGS QEGAMHTALT GATEIQNSGG TS....IPAG HLKCRLKMDK    289
   DENV1_E_AA   KKQEVVVLGS QEGAMHTALT GATEIQTSGT TT....IPAG HLKCRLKMDK    291
   DENV4_E_AA   KRQDVTVLGS QEGAMHSALA GATEVDSGDG NH....MFAG HLKCKVRMEK    291
   DENV_2_E_AA  KKQDVVVLGS QEGAMHTALT GATEIQMSSG NL....LFTG HLKCRLRMDK    291
        YF_17D  ATIRVLALGN QEGSLKTALT GAMRVTKDTN DNNLYKLHGG HVSCRVKLSA    289
        JESA14  TKQSVVALGS QEGGLHQALA GAIVVEYSSS VK....LTSG HLKCRLKMDK    293

301                                                    350
DENV3_E_AA#2    LELKGMSYAM CTNTFVLKKE VSETQHGTIL IKVEYKGEDA PCKIPF.STE    338
   DENV1_E_AA   LTLKGMSYVM CTGSFKLEKE VAETQHGTVL VQVKYEGTDA PCKIPF.SSQ    340
   DENV4_E_AA   LRIKGMSYTM CSGKFSIDKE MAETQHGTTV VKVKYEGAGA PCKVPI.EIR    340
   DENV_2_E_AA  LQLKGMSYSM CTGKFKVVKE IAETQHGTIV IRVQYEGDGS PCKIPF.EIM    340
        YF_17D  LTLKGTSYKI CTDKMFFVKN PTDTGHGTVV MQVKVSKGAP CRIPVI.VAD    338
        JESA14  LALKGTTYGM CTEKFSFAKN PADTGHGTVV IELSYSGSDG PCKIPIVSVA    343

351                                                    400
DENV3_E_AA#2    DGQGKAHNGR LITANPVVTK KEEPVNIE AEPPFGESNI VIGIGDKALK    386
   DENV1_E_AA   DEKGVTQNGR LITANPIVTD K..EKPVNIE AEPPFGESYI VVGAGEKALK    388
   DENV4_E_AA   DVNKEKVVGR VISSTPLAEN T..NSVTNIE LEPPFGDSYI VIGVGNSALT    388
   DENV_2_E_AA  DLEKRHVLGR LITVNPIVTE K..DSPVNIE AEPPFGDSYI IIGVDPGQLK    388
        YF_17D  DLTAAINKGI LVTVNPIAST N..DDEVLIE VNPPFGDSYI IVGRGDSRLT    386
        JESA14  SLNDMTFVGR LVTVNPFVAT SSANSKVLVE MEPPFGDSYI VVGRGDKQIN    393

401              424
DENV3_E_AA#2    INWYKKGSSI GKMFEATARG ARRM (SEQ ID NO:17)                  410
   DENV1_E_AA   LSWFKKGSSI GKMFEATARG AR..  (SEQ ID NO:18)                 410
   DENV4_E_AA   LHWFRKGSSI GKMFESTYRG AK..  (SEQ ID NO:19)                 410
   DENV_2_E_AA  LNWFKKGSSI GQMFETTMRG AK..  (SEQ ID NO:20)                 410
        YF_17D  YQWHKEGSSI GKLFTQTMKG VERL  (SEQ ID NO:21)                 410
        JESA14  HHWHKAGSTL GKAFSTT... ....  (SEQ ID NO:22)                 410
```

CHIMERIC DENGUE VIRUS E GLYCOPROTEINS COMPRISING MUTANT DOMAIN I AND DOMAIN II HINGE REGIONS

STATEMENT OF PRIORITY

This application is a 35 USC §371 national phase application of International Application Serial No. PCT/US2013/032367, filed Mar. 15, 2013, which claims the benefit under 35 U.S.C. §119(e), of U.S. Provisional Application No. 61/619,247, filed Apr. 2, 2012, the entire contents of each of which are incorporated by reference herein.

STATEMENT OF GOVERNMENT SUPPORT

This invention was made with government support under Grant No. U54 AI057157 awarded by the National Institutes of Health. The United States government has certain rights in the invention.

STATEMENT REGARDING ELECTRONIC FILING OF A SEQUENCE LISTING

A Sequence Listing in ASCII text format, submitted under 37 C.F.R. §1.821, entitled 5470-626TS_ST25.txt, 24,827 bytes in size, generated on Aug. 24, 2016 and filed via EFS-Web, is provided in lieu of a paper copy. This Sequence Listing is hereby incorporated by reference into the specification for its disclosures.

FIELD OF THE INVENTION

The present invention is based, in part, on the discovery by the inventors of a novel complex, quaternary structure dengue virus epitope that spans adjacent E protein dimers in the assembled virus particle. Further, the inventors have demonstrated that antibodies directed against this epitope neutralize dengue virus infection. These findings have significant implications for the design and characterization of immunogenic compositions intended to produce an immune response to dengue virus.

In particular, the inventors have identified a dengue virus epitope that has a footprint that spans the hinge region between domains I and II of the E protein in one E protein homodimer. In some cases, this epitope extends into portions of domain III from an E protein in an adjacent homodimer, where both E proteins are in the same orientation within their respective homodimers.

BACKGROUND

Dengue is a mosquito-borne flavivirus that is spreading at an unprecedented rate and has developed into a major health and economic burden in over 50 countries. Even though infected individuals develop potent and long-lasting serotype-specific neutralizing antibodies (Abs), the epitopes engaged by human neutralizing Abs have not been identified. Here, we demonstrate that the dengue virus (DENV)-specific serum Ab response in humans consists of a large fraction of cross-reactive, poorly neutralizing Abs and a small fraction of serotype-specific, potently inhibitory Abs. Although many mouse-generated, strongly neutralizing monoclonal antibodies (MAbs) recognize epitopes that are present on recombinant DENV envelope (E) proteins, unexpectedly, the majority of neutralizing Abs in human immune sera bound to intact virions but not to the ectodomain of purified soluble E proteins. These conclusions with polyclonal Abs were confirmed with newly generated human MAbs derived from DENV-immune individuals. Two of three strongly neutralizing human MAbs bound to E protein epitopes that were preserved on the virion but not on recombinant E (rE) protein. It is proposed that humans produce Abs that neutralize DENV infection by binding a complex, quaternary structure epitope that is expressed only when E proteins are assembled on a virus particle. Mapping studies indicate that this epitope has a footprint that spans adjacent E protein dimers and includes residues at the hinge between domains I and II of E protein. These results have significant implications for the DENV Ab and vaccine field.

SUMMARY OF THE INVENTION

Thus, the invention provides a dengue virus epitope (e.g., an isolated dengue virus epitope) that spans adjacent dengue virus E protein dimers and comprises the hinge region between domains I and II of a first E protein from a first E protein dimer and domain III of a second dengue virus E protein from a second E protein dimer.

The dengue virus epitope of the invention can be present in an intact virus particle (e.g., a killed or live attenuated virus particle or a recombinant dengue virus vector) or a virus-like particle (VLP), which may optionally be an intact dengue virus particle or dengue virus VLP.

Alternatively, dengue virus particles or VLPs can be processed, for example, chemically cross-linked and/or cleaved with protease to release the epitope from the viral coat and provide the epitope in a processed form.

The invention also provides isolated and/or recombinant polypeptides comprising a dengue virus E protein domain I and domain II hinge region, a peptide spacer, and at least a portion of a dengue virus E protein domain III. While not wishing to be bound by any theory of the invention, it appears that the epitope is formed between adjacent E protein homodimers because the E protein domain III is not in sufficiently close proximity within the same E protein molecule or even homodimer (see, e.g., FIG. 3 of the Appendix). Thus, based on this knowledge, E proteins can be engineered in which the E protein domain III is brought into closer proximity to the E domain I/II hinge region, thereby providing an epitope formed within a single E protein molecule. Such an approach would be desirable from a standpoint of the manufacture and delivery of immunogenic compositions to produce an immune response to dengue virus, for example, as a soluble subunit immunogenic composition.

In further embodiments, the present invention provides a chimeric dengue virus E glycoprotein comprising a dengue virus E glycoprotein backbone, which comprises amino acid substitutions that introduce a dengue virus E glycoprotein domain I and domain II hinge region from a dengue virus serotype that is different from the dengue virus serotype of the dengue virus E glycoprotein backbone. The chimeric dengue virus E glycoprotein described herein can further comprise amino acid substitutions that introduce a dengue virus E glycoprotein domain III region from a dengue virus serotype that is different from the dengue virus serotype of the dengue virus E glycoprotein backbone.

Also provided herein is a chimeric flavivirus E glycoprotein comprising a flavivirus E glycoprotein backbone from a flavivirus that is not dengue virus, which comprises amino acid substitutions that introduce a dengue virus E glycoprotein domain I and domain II hinge region into the flavivirus E glycoprotein backbone. The chimeric flavivirus E glycoprotein described herein can further comprise amino acid substitutions that introduce a dengue virus E glycoprotein domain III region into the flavivirus E glycoprotein backbone.

Furthermore, the present invention provides a method of producing an immune response to a dengue virus in a subject, treating a dengue virus infection in a subject in need thereof, preventing a dengue virus infection in a subject and/or protecting a subject from the effects of dengue virus infection, such methods comprising administering to the subject an effective amount of an isolated dengue virus epitope of this invention, a polypeptide of this invention, an E glycoprotein of this invention, a flavivirus particle or VLP of this invention, a nucleic acid of this invention, a composition of this invention and any combination thereof.

In some embodiments, the epitopes, proteins, virus particles and/or VLPs of this invention can be readily used in diagnostic methods to determine if a subject produces an antibody that specifically binds to the native quaternary epitope, e.g., to determine if the subject has neutralizing antibodies. Such a diagnostic method finds use, for example, to determine the quality of the subject's immune response following natural infection with dengue virus and/or following administration of an immunogenic composition intended to produce an immune response to dengue virus (e.g., to determine if the immunogenic composition induces neutralizing antibodies that specifically bind to the native quaternary epitope on the virus).

A method is also provided herein of detecting a neutralizing antibody to a dengue virus, the method comprising the step of determining whether an antibody binds to an isolated dengue virus epitope of this invention, a polypeptide of this invention, an E glycoprotein of this invention and/or a flavivirus particle or VLP of this invention, wherein binding by the antibody to the isolated dengue virus epitope of this invention, the polypeptide of this invention, the E glycoprotein of this invention and/or the flavivirus particle or VLP of this invention detects a neutralizing antibody to a dengue virus.

Additionally provided herein is a method of identifying a neutralizing antibody to a dengue virus, the method comprising: (a) contacting an antibody with to an isolated dengue virus epitope of this invention, a polypeptide of this invention, an E glycoprotein of this invention and/or a flavivirus particle or VLP of this invention; and (b) determining if the antibody binds to the isolated dengue virus epitope of this invention, the polypeptide of this invention, the E glycoprotein of this invention and/or the flavivirus particle or VLP of this invention, wherein binding by the antibody to the isolated dengue virus epitope of this invention, the polypeptide of this invention, the E glycoprotein of this invention and/or the flavivirus particle or VLP of this invention identifies the antibody as a neutralizing antibody to a dengue virus.

The present invention further provides a method of identifying an immunogenic composition that induces a neutralizing antibody to a dengue virus in a subject, the method comprising: (a) contacting a biological sample from a subject that has been administered the immunogenic composition with an isolated dengue virus epitope of this invention, a polypeptide of this invention, an E glycoprotein of this invention and/or a flavivirus particle or VLP of this invention; (b) determining if the biological sample comprises an antibody that binds to the isolated dengue virus epitope of this invention, the polypeptide of this invention, the E glycoprotein of this invention and/or the flavivirus particle or VLP of this invention; and (c) identifying the immunogenic composition as inducing a neutralizing antibody to a dengue virus in the subject if the biological sample comprises an antibody that binds to the isolated dengue virus epitope of this invention, the polypeptide of this invention, the E glycoprotein of this invention and/or the flavivirus particle or VLP of this invention.

Also provided herein is a method of identifying an immunogenic composition that induces a neutralizing antibody to a dengue virus in a subject, the method comprising: (a administering an immunogenic composition comprising a dengue virus antigen to a subject in an amount effective to induce antibodies against the dengue virus antigen; (b) contacting a biological sample from the subject with an isolated dengue virus epitope of this invention, a polypeptide of this invention, an E glycoprotein of this invention and/or a flavivirus particle or VLP of this invention; (c) determining if the biological sample comprises an antibody that binds the isolated dengue virus epitope of this invention, the polypeptide of this invention, the E glycoprotein of this invention and/or the flavivirus particle or VLP of this invention; and (d identifying the immunogenic composition as inducing a neutralizing antibody to a dengue virus in the subject if the biological sample comprises an antibody that binds to the isolated dengue virus epitope of this invention, the polypeptide of this invention, the E glycoprotein of this invention and/or the flavivirus particle or VLP of this invention.

BRIEF DESCRIPTION OF THE DRAWINGS

FIG. 11. Alignment of E glycoprotein sequences of dengue virus serotypes and other flaviviruses. (SEQ ID NOS: 17-22)

DETAILED DESCRIPTION OF THE INVENTION

Figure 1:
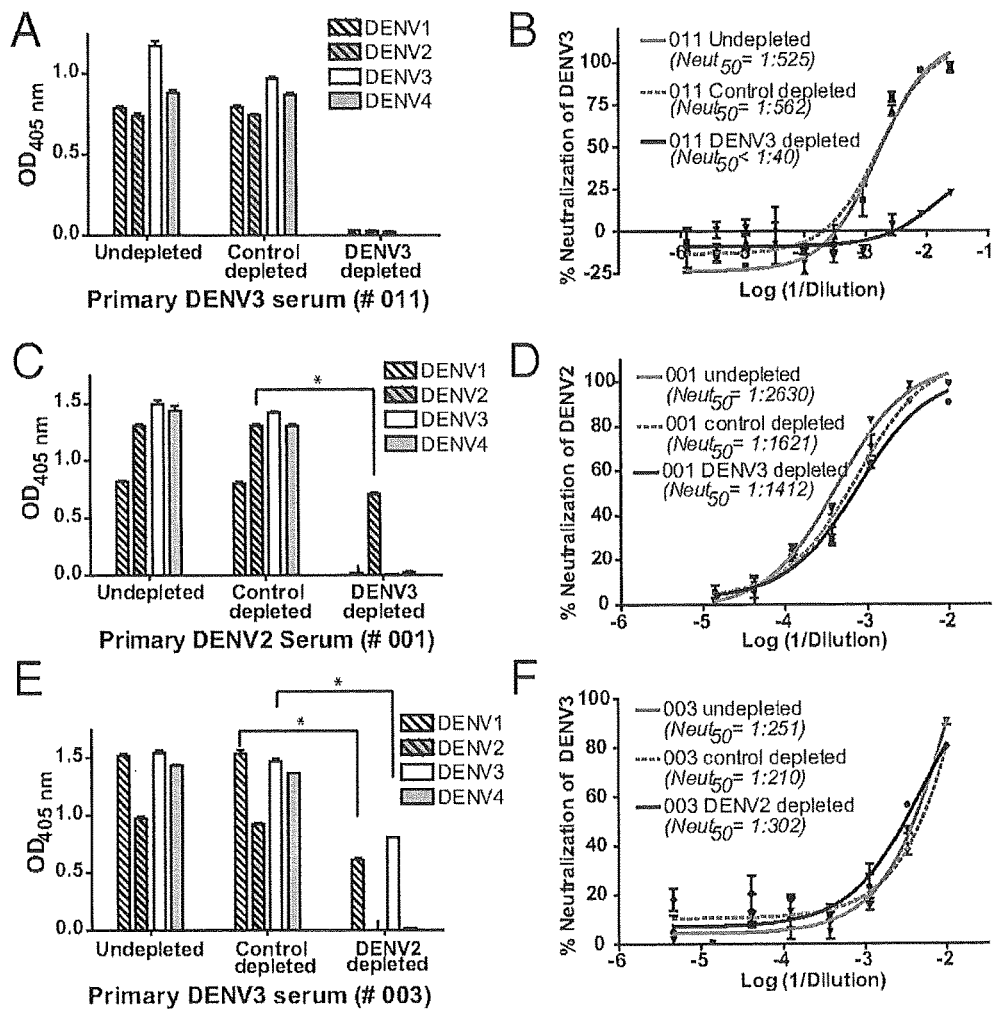
FIG. 1: Binding and neutralization properties of primary DENV-immune sera depleted of total or cross-reactive DENV-binding Abs. (A and B) Total DENV-specific Abs were removed from a DENV3 primary immune serum (e.g. subject 011) using polystyrene beads coated with purified DENV3 and tested for (A) DENV binding and (B) neutralization. The serum depleted with the homologous serotype did not bind to any of the four DENV viruses and failed to neutralize DENV3. Similar results were observed for four other primary immune sera (two DENV2 and two DENV3 sera) depleted with the homologous serotype responsible for infection. (C-F) Primary DENV2 (C and D) and DENV3 (E and F) immune sera were depleted of cross-reactive Abs using beads coated with virus of heterologous serotype, and tested for DENV virus binding (C and E) and neutralization of the homologous serotype (D and F). Immune sera depleted of cross-reactive Abs contained type-specific Abs that bound to virus from the homologous serotype only Immune sera depleted of cross-reactive Abs were as potently neutralizing as undepleted or control depleted sera. Results presented here for cross-reactive antibody depletions are representative of data obtained with four primary DENV2 and three primary DENV3 human immune sera (See Table 1). *P<0.001 by unpaired student t-test of mean binding values.

The present invention is based, in part on the unexpected discovery that epitope regions that define a DENV serotype can be transferred into or created in chimeric molecules. Thus, in one embodiment, the present invention provides a chimeric dengue virus E glycoprotein comprising a dengue virus E glycoprotein backbone, which comprises amino acid substitutions that introduce a dengue virus E glycoprotein domain I and domain II hinge region from a dengue virus serotype that is different from the dengue virus serotype of the dengue virus E glycoprotein backbone. In some embodiments, the chimeric dengue virus E glycoprotein described herein above can further comprise amino acid substitutions that introduce a dengue virus E glycoprotein domain III region from a dengue virus serotype that is different from the dengue virus serotype of the dengue virus E glycoprotein backbone. In such embodiments, the dengue virus E glycoprotein backbone can be from dengue virus serotype 1, dengue virus serotype 2, dengue virus serotype 3 or dengue virus serotype 4.

Furthermore, the domain I and domain II hinge region of the chimeric dengue virus E glycoprotein of this invention can be from dengue virus serotype 1, dengue virus serotype 2, dengue virus serotype 3 or dengue virus serotype 4.

In embodiments wherein the chimeric dengue virus E glycoprotein comprises amino acid substitutions that introduce a dengue virus E glycoprotein domain I and domain II hinge region E and further comprises amino acid substitutions that introduce a dengue virus E glycoprotein domain III region, the domain 1 and domain II hinge region and the domain III region can be from dengue virus serotype 1, dengue virus serotype 2, dengue virus serotype 3 or dengue virus serotype 4.

In additional embodiments, of this invention, a chimeric flavivirus E glycoprotein is provided, said chimeric flavivirus E glycoprotein comprising a flavivirus E glycoprotein backbone from a flavivirus that is not dengue virus, which comprises amino acid substitutions that introduce a dengue virus E glycoprotein domain I and domain II hinge region into the flavivirus E glycoprotein backbone. In some embodiments, the chimeric flavivirus E glycoprotein can further comprise amino acid substitutions that introduce a dengue virus E glycoprotein domain III region into the flavivirus E glycoprotein backbone.

In some embodiments, the flavivirus E glycoprotein backbone can be from any flavivirus, including but not limited to, yellow fever virus (YFV), Japanese encephalitis virus (JEV) or West Nile virus (WNV).

Furthermore, the domain I and domain II hinge region of the chimeric flavivirus E glycoprotein of this invention can be from dengue virus serotype 1, dengue virus serotype 2, dengue virus serotype 3 or dengue virus serotype 4.

In embodiments wherein the chimeric flavivirus E glycoprotein comprises amino acid substitutions that introduce a dengue virus E glycoprotein domain I and domain II hinge region E and further comprises amino acid substitutions that introduce a dengue virus E glycoprotein domain III region, the domain 1 and domain II hinge region and the domain III region can be from dengue virus serotype 1, dengue virus serotype 2, dengue virus serotype 3 or dengue virus serotype 4.

The present invention also provides a flavivirus particle or virus like particle (VLP) comprising the chimeric dengue virus E glycoprotein or chimeric flavivirus E glycoprotein of this invention.

In addition, the present invention provides an isolated nucleic acid encoding the chimeric dengue virus E glycoprotein or the chimeric flavivirus E glycoprotein of this invention, as well as an isolated nucleic acid encoding the isolated dengue virus epitope of this invention, an isolated nucleic acid encoding the polypeptide of this invention, an isolated nucleic acid encoding the flavivirus particle, VLP or viral coat of the chimeric flavivirus of this invention.

Further provided herein is a composition comprising the isolated dengue virus epitope this invention, the polypeptide of this invention, the chimeric VLP of this invention, the chimeric dengue virus E glycoprotein or chimeric flavivirus E glycoprotein of this invention, the flavivirus particle or VLP of this invention, the nucleic acid of this invention and any combination thereof, in a pharmaceutically acceptable carrier.

The dengue virus E glycoprotein domain I and domain II hinge region makes up a conformational epitope that induces the production of neutralizing antibodies. All or part of the domain III region of the E glycoprotein can be included to form a conformational epitope that induces the production of neutralizing antibodies.

The term "dengue virus E protein domain I and domain II hinge region" and similar terms would be understood in the art to include the three-dimensional interface between domain I and II in the dengue virus E glycoprotein and, optionally, the adjacent amino acid residues. In addition, those skilled in the art will appreciate that certain amino acid residues in the hinge region may facilitate proper folding and presentation of the epitope, even if they do not form part of the epitope per se. In representative embodiments, the dengue virus E protein domain I and domain II hinge region comprises, consists essentially of, or consists of amino acid positions 47-59, 124-133, 199-222 and/or 206-228 of the E protein of dengue virus serotype 3 (DENV3; e.g., GenBank® Database Accession No. JQ411814) or the corresponding positions of the E protein of other dengue viruses (e.g., dengue virus serotypes 1 (DENV1; e.g., GenBank® Database Accession No. U88535), 2 (DENV2; e.g., GenBank® Database Accession No. NC_001474) or DENV4; full E glycoprotein sequences are shown in FIG. 11 and corresponding amino acid numbers are provided in Table 6).

The term "at least a portion of a dengue virus E protein domain III" and similar terms refer to those portions of E protein domain III that form part of the epitope as well as those amino acid residues that facilitate proper folding and presentation of the epitope, even if they do not form part of the epitope per se. In representative embodiments, the dengue virus E protein domain III comprises, consists essentially of, or consists of amino acid positions 305-308, 323-325, 359-362 and/or 389-390 of the E protein of dengue virus serotype 3 or the corresponding positions of the E protein of other dengue viruses (e.g., dengue virus serotypes 1 (DENV1), 2 (DENV2) or DENV4; full E glycoprotein sequences are shown in FIG. 11 and corresponding amino acid numbers are provided in Table 6).

Thus, the present invention provides a chimeric dengue virus E glycoprotein comprising a DENV1 domain I and domain II hinge region in a DENV2, DENV3 or DENV4 E glycoprotein backbone. Also provided is a chimeric dengue virus E glycoprotein comprising a DENV1 domain I and domain II hinge region as well as a domain III region in a DENV2, DENV3 or DENV4 E glycoprotein backbone.

Further provided is a chimeric dengue virus E glycoprotein comprising a DENV3 domain I and domain II hinge region in a DENV1, DENV2 or DENV4 E glycoprotein backbone. Also provided is a chimeric dengue virus E glycoprotein comprising a DENV3 domain I and domain II hinge region as well as a domain III region in a DENV1, DENV2 or DENV4 E glycoprotein backbone. Further provided is a chimeric dengue virus E glycoprotein comprising a DENV4 domain I and domain II hinge region in a DENV1, DENV2 or DENV3 E glycoprotein backbone. Also provided is a chimeric dengue virus E glycoprotein comprising a DENV4 domain I and domain II hinge region as well as a domain III region in a DENV1, DENV2 or DENV3 E glycoprotein backbone. Production of these chimeras can be carried out by introducing some (e.g., 1, 2, 3, 4, 5, 6, 7, 8, 9, 10, etc.) or all of the amino acid substitutions identified in Table 6. Not every amino acid identified in Table 6 is required to be substituted to produce a chimeric protein of this invention. For example, in some embodiments further substitutions and/or omission of substitutions of about 1, 2, 3, 4 or 5 amino acids at either end of the contiguous amino acid sequences identified in Table 6 as the respective epitope regions can be included in production of a chimera of this invention. The number of substitutions necessary to produce the desired conformational epitope can be readily determined by one of ordinary skill in the art according to the teachings herein and according to protocols well known in the art.

In some embodiments, the present invention provides a chimeric flavivirus E glycoprotein in which amino acid substitutions are made to introduce a dengue virus epitope into a flavivirus E glycoprotein from a flavivirus that is not a dengue virus. Nonlimiting examples of flaviviruses that can be used include yellow fever virus (YFV) (e.g., GenBank® Database Accession No. JX503529) Japanese encephalitis virus (JEV) (e.g., GenBank® Database Accession No. U14163), West Nile virus (WNV) (e.g., GenBank® Database Accession No. DQ211652) and any other flavivirus now known or later identified. Thus, the present invention provides, for example a chimeric flavivirus E glycoprotein comprising a DENV1, DENV2, DENV3, or DENV4 domain I and domain II hinge region in a YFV, JEV or WNV E glycoprotein backbone. Also provided is a chimeric dengue virus E glycoprotein comprising a DENV1, DENV2, DENV3 or DENV4 domain I and domain II hinge region as well as a domain III region in a YFV, JEV or WNV E glycoprotein backbone.

In other embodiments, "at least a portion of a dengue virus E protein domain III" (and similar terms) comprises, consists essentially of, or consists of at least about 6, 8, 10, 12, 15, 20, 30, 40, 50, 60, 70, 80, 90 or 100 amino acids, optionally contiguous amino acids, and/or less than about 12, 15, 20, 30, 40, 50, 60, 70, 80, 90 or 100 amino acids, optionally contiguous amino acids, including any combination of the foregoing as long as the lower limit is less than the upper limit.

In representative embodiments, the peptide spacer comprises, consists of, or consists essentially of about 1, 2, 3 or less, 4 or less, 5 or less, 6 or less, 7 or less, 8 or less, 9 or less, 10 or less, 11 or less, 12 or less, 13 or less, 14 or less, 15 or less, 16 or less, 17 or less, 18 or less, 19 or less, 20 or less, 25 or less, 30 or less, 35 or less, 40 or less, 45 or less, 50 or less, 55 or less, 60 or less, 70 or less, 80 or less, 90 or less or 100 or less amino acids. In embodiments, the peptide spacer comprises, consists of, or consists essentially of about 1 to about 5, 10, 15, 20, 25, 30, 35, 40, 45, 50, 55, 60, 70, 80, 90 or 100 amino acids. In embodiments, the peptide spacer comprises, consists of, or consists essentially of about 3 to about 10, 15, 20, 25, 30, 35, 40, 45, 50, 55, 60, 70, 80, 90 or 100 amino acids. In embodiments, the peptide spacer comprises, consists of, or consists essentially of about 4 to about 10, 15, 20, 25, 30, 35, 40, 45, 50, 55, 60, 70, 80, 90 or 100 amino acids. In embodiments, the peptide spacer comprises, consists of, or consists essentially of about 5 to about 10, 15, 20, 25, 30, 35, 40, 45, 50, 55, 60, 70, 80, 90 or 100 amino acids. In embodiments, the peptide spacer comprises, consists of, or consists essentially of about 10 to about 20, 25, 30, 35, 40, 45, 50, 55, 60, 70, 80, 90 or 100 amino acids. In embodiments, the peptide spacer comprises, consists of, or consists essentially of about 15 to about 20, 25, 30, 35, 40, 45, 50, 55, 60, 70, 80, 90 or 100 amino acids. In embodiments, the peptide spacer comprises, consists of, or consists essentially of about 20 to about 25, 30, 35, 40, 45, 50, 55, 60, 70, 80, 90 or 100 amino acids.

In embodiments, the spacer brings the E protein domain I/II hinge region and the domain III region involved in the quaternary epitope about 10 or less, 15 or less, 20 or less, 25 or less, 30 or less, 35 or less, 40 or less, 45 or less, 50 or less, 60 or less or 70 or less angstroms apart. In embodiments, the spacer brings the E protein domain I/II hinge region and the domain III region involved in the quaternary epitope about 10 to 20, 25, 30, 35, 40, 45, 50, 60 or 70 angstroms apart. In embodiments, the spacer brings the E protein domain I/II hinge region and the domain III region involved in the quaternary epitope about 15 to 25, 30, 35, 40, 45, 50, 60 or 70 angstroms apart. In embodiments, the spacer brings the E protein domain I/II hinge region and the domain III region involved in the quaternary epitope about 20 to 30, 35, 40, 45, 50, 60 or 70 angstroms apart. In embodiments, the spacer brings the E protein domain I/II hinge region and the domain III region involved in the quaternary epitope about 25 to 35, 40, 45, 50, 60 or 70 angstroms apart. In embodiments, the spacer brings the E protein domain I/II hinge region and the domain III region involved in the quaternary epitope about 30 to 40, 45, 50, 60 or 70 angstroms apart. In embodiments, the spacer brings the E protein domain I/II hinge region and the domain III region involved in the quaternary epitope about 35 to 45, 50, 60 or 70 angstroms apart.

The peptide spacer can be derived in whole or in part from a native E protein, or can be partially or wholly synthetic.

In embodiments, the peptide spacer forms a secondary structure, e.g., a beta-sheet, beta-barrel and/or an alpha helical structure. In embodiments, the peptide spacer comprises one or more disulfide bonds (e.g., cysteine residues).

It is known in the art that many attempts to produce dengue virus vaccines result in the production of non-neutralizing antibodies, which may increase the likelihood of pathology upon subsequence exposure to natural infection or vaccine. Another approach to provide an engineered epitope is to deliver all or a portion of the dengue virus E protein incorporated into another flavivirus particle or VLP. In representative embodiments, the heterologous flavivirus is West Nile virus or Yellow Fever virus. Portions of the E protein can be grafted into the E protein of the heterologous flavivirus backbone, e.g., to reduce the generation of non-neutralizing dengue virus antibodies to non-neutralizing epitopes present in the dengue virus E protein and/or other dengue virus structural proteins.

Thus, a chimeric flavivirus or chimeric flavivirus VLP can present the quaternary dengue virus epitope in proper conformation while reducing the generation of non-neutralizing antibodies to other portions of the dengue virus E protein and/or other structural proteins that are not presented in the chimeric flavivirus or flavivirus VLP.

Thus, as another aspect, the invention provides a chimeric flavivirus particle or chimeric flavivirus VLP comprising a chimeric flavivirus E protein, the chimeric flavivirus E protein comprising a dengue virus E protein domain I and domain II hinge region and at least a portion of the dengue virus E protein domain III. In embodiments of the invention, the dengue virus E protein region(s) are substituted for the corresponding region(s) of the heterologous flavivirus E protein. In embodiments, amino acid sequences from the dengue virus prM protein and/or the dengue virus C protein are not incorporated into the chimeric flavivirus or chimeric flavivirus VLP.

In some embodiments of the invention the individual and conformational epitopes of the flavivirus E glycoprotein or dengue virus E glycoprotein can be presented on a synthetic backbone or support structure so that the epitopes within the synthetic backbone or support structure mimic the conformation and arrangement of the epitopes within the structure of the E glycoprotein, virus particle or VLP.

In still further embodiments of the invention, the present invention provides peptide mimitopes (see, Meloen et al. (2000) *J. Mol. Recognit.* 13, 352-359) that mimic the individual and conformational epitopes of the E glycoproteins of the invention. Mimitopes may be identified using any technique known in the art, such as by surface stimulation, random peptide libraries or phage display libraries, using an antibody or antibodies to the individual and conformational epitopes of the E glycoproteins of the invention.

The invention further provides a nucleic acid (e.g., isolated nucleic acid) encoding a dengue virus epitope or a polypeptide of the invention.

The invention further provides a nucleic acid (e.g., an isolated nucleic acid) encoding a chimeric flavivirus VLP or a viral coat of a chimeric flavivirus particle of the invention.

Also provided are vectors encoding the nucleic acids of the invention.

Also provided are cells comprising the vectors, nucleic acids, dengue virus epitopes, polypeptides, chimeric flavivirus VLPs or chimeric flavivirus particles of the invention.

The invention also provides immunogenic compositions comprising the cells, vectors, nucleic acids, dengue virus epitopes, polypeptides, chimeric flavivirus VLPs or chimeric flavivirus particles of the invention. In embodiments, the immunogenic composition is monovalent. In embodiments, the immunogenic composition is multivalent (e.g., tetravalent) for dengue virus serotypes DEN1, DEN2, DEN 3 and/or DEN4.

The invention encompasses methods of producing an immune response to a dengue virus in a subject, the method comprising administering to the subject an effective amount of a dengue virus epitope, a polypeptide, a chimeric flavivirus VLP or chimeric flavivirus particle, nucleic acid, vector, cell or immunogenic composition of the invention.

Further, the present invention can advantageously be practiced to induce an immune response against one, two, three or all four of DEN1, DEN2, DEN3 and DEN4. It is well-known in the art that effective and safe multivalent dengue vaccines have been a challenge to design because of the problem of interference among serotypes. For example, the immune response may be predominantly directed against only some of the target serotypes. Multiple vaccinations are then required to try to achieve a response against all serotypes; however, in the case of dengue virus, this approach can be dangerous because repeated administrations to a subject with pre-existing antibodies can lead to dengue hemorrhagic fever.

A still further aspect of the invention is a method of treating a dengue virus infection, comprising administering to the subject an effective amount of a dengue virus epitope, a polypeptide, a chimeric flavivirus VLP or chimeric flavivirus particle, nucleic acid, vector, cell, or immunogenic composition of the invention.

A still further aspect of the invention is a method of preventing a dengue virus infection, comprising administering to the subject an effective amount of a dengue virus epitope, a polypeptide, a chimeric flavivirus VLP or chimeric flavivirus particle, nucleic acid, vector, cell, or immunogenic composition of the invention.

A still further aspect of the invention is a method of protecting a subject from the effects of dengue virus infection, comprising administering to the subject an effective amount of a dengue virus epitope, a polypeptide, a chimeric flavivirus VLP or chimeric flavivirus particle, nucleic acid, vector, cell, or immunogenic composition of the invention.

The invention can also be practiced to identify antibodies that bind (e.g., specifically bind) to the quaternary dengue virus epitope, e.g., to identify neutralizing antibodies to a dengue virus. For example, the invention can be employed as a diagnostic to qualitatively determine if a vaccine candidate is inducing neutralizing antibodies. In general, due to the abundance of non-neutralizing antibodies induced by many candidate dengue virus vaccines, antibody titers alone without further characterization of the antibody specificity provides incomplete information.

In representative embodiments, the invention provides a method of detecting a neutralizing antibody to a dengue virus, the method comprising the step of determining whether an antibody binds to a dengue virus epitope, a polypeptide, or a chimeric VLP or chimeric flavivirus of the invention, wherein binding by the antibody to the dengue virus epitope, the polypeptide, the chimeric VLP or the chimeric flavivirus indicates that the antibody is a neutralizing antibody to a dengue virus.

In further representative embodiments, the invention provides a method of identifying a neutralizing antibody to a dengue virus, the method comprising: (a) contacting an antibody to a dengue virus epitope, a polypeptide, or a chimeric VLP or chimeric flavivirus of the invention; and (b) determining if the antibody binds to the dengue virus epitope, the polypeptide, the chimeric VLP or the chimeric flavivirus; wherein binding by the antibody to the dengue virus epitope, the polypeptide, the chimeric VLP or the chimeric flavivirus indicates that the antibody is a neutralizing antibody to a dengue virus.

The invention also provides a method of identifying a neutralizing antibody to a dengue virus, the method comprising: (a) contacting an antibody to a dengue virus epitope, a polypeptide, or a chimeric VLP or chimeric flavivirus of the invention; (b) determining if the antibody binds to the dengue virus epitope, the polypeptide, the chimeric VLP or the chimeric flavivirus; and (c) identifying the antibody as a neutralizing antibody to a dengue virus if the antibody binds to the dengue virus epitope, the polypeptide, the chimeric VLP or the chimeric flavivirus.

Still further, the invention provides a method of identifying an immunogenic composition that induces a neutralizing antibody to a dengue virus in a subject, the method comprising the step of determining whether a biological sample obtained from a subject that has been administered the immunogenic composition comprises an antibody that binds to a dengue virus epitope, a polypeptide, or a chimeric VLP or chimeric flavivirus of the invention, wherein if the biological sample comprises an antibody that binds to the dengue virus epitope, the polypeptide, the chimeric VLP or the chimeric flavivirus, it indicates that the immunogenic composition induces a neutralizing antibody to a dengue virus in the subject.

The invention also provides a method of identifying an immunogenic composition that induces a neutralizing antibody to a dengue virus in a subject, the method comprising: (a) contacting a biological sample from a subject that has been administered the immunogenic composition with a dengue virus epitope, a polypeptide, or a chimeric VLP or chimeric flavivirus of the invention; and (b) determining if the biological sample comprises an antibody that binds to the dengue virus epitope, the polypeptide, the chimeric VLP or the chimeric flavivirus; wherein if the biological sample comprises an antibody that binds to the dengue virus epitope, the polypeptide, the chimeric VLP or the chimeric flavivirus, it indicates that the immunogenic composition induces a neutralizing antibody to a dengue virus in the subject.

In yet another embodiment, the invention provides a method of identifying an immunogenic composition that induces a neutralizing antibody to a dengue virus in a subject, the method comprising: (a) contacting a biological sample from a subject that has been administered the immunogenic composition with a dengue virus epitope, a polypeptide, or a chimeric VLP or chimeric flavivirus of the invention; (b) determining if the biological sample comprises an antibody that binds to the dengue virus epitope, the polypeptide, the chimeric VLP or the chimeric flavivirus; and (c) identifying the immunogenic composition as inducing a neutralizing antibody to a dengue virus in the subject if the biological sample comprises an antibody that binds to the dengue virus epitope, the polypeptide, the chimeric VLP or the chimeric flavivirus.

In other representative embodiments, the invention provides a method of identifying an immunogenic composition that induces a neutralizing antibody to a dengue virus in a subject, the method comprising: (a) administering an immunogenic composition comprising a dengue virus antigen to a subject in an amount effective to induce antibodies against the dengue virus antigen; (b) contacting a biological sample from the subject with a dengue virus epitope, a polypeptide, or a chimeric VLP or chimeric flavivirus of the invention; (c) determining if the biological sample comprises an antibody that binds to the dengue virus epitope, the polypeptide, the chimeric VLP or chimeric flavivirus; and (d) identifying the immunogenic composition as inducing a neutralizing antibody to a dengue virus in the subject if the biological sample comprises an antibody that binds to the dengue virus epitope, the polypeptide, the chimeric VLP or the chimeric flavivirus.

There are four serotypes of dengue virus (DEN1, DEN2, DEN3 and DEN4). Within each serotype there are a number of different strains or genotypes. The dengue virus antigens and epitopes of the invention can be derived from any dengue virus, including all serotypes, strains and genotypes, now known or later identified.

In embodiments of the invention, the dengue virus is UNC1017 strain (DEN1), West Pacific 74 strain (DEN1), 516803 strain (DEN2), UNC2005 strain (DEN2), UNC3001 strain (DEN3), UNC3043 (DEN3 strain 059.AP-2 from Philippines, 1984), UNC3009 strain (DEN3, D2863, Sri Lanka 1989), UNC3066 (DEN3, strain 1342 from Puerto Rico 1977), CH53489 strain (DEN3), UNC4019 strain (DEN4), or TVP-360 (DEN4).

In embodiments of the invention, an "immunogenically active fragment" of a dengue virus polypeptide (e.g., the E protein, or the EDI, EDII or EDIII domain) comprises, consists essentially of or consists of at least about 6, 8, 10, 12, 15, 20, 30, 50, 75, 100, 125, 150, 200, 250, 300, 350, 400, 450 or more amino acids, optionally contiguous amino acids, and/or less than about 495, 475, 450, 425, 400, 350, 300, 250, 200, 150, 100, 75 or 50 amino acids, optionally contiguous amino acids, including any combination of the foregoing as long as the lower limit is less than the upper limit, and the "immunogenically active fragment" induces an immune response (e.g., IgG and/or IgA that react with the native antigen), optionally a protective immune response, against dengue virus in a host and induces the production of antibodies that specifically bind to the quaternary dengue virus epitope newly identified by the inventors.

The term "epitope" as used herein means a specific amino acid sequence that, when present in the proper conformation, provides a reactive site for an antibody (e.g., B cell epitope) or T cell receptor (e.g., T cell epitope).

Portions of a given polypeptide that include a B-cell epitope can be identified using any number of epitope mapping techniques that are known in the art. (See, e.g., *Epitope Mapping Protocols in Methods in Molecular Biology*, Vol. 66, Glenn E. Morris, Ed., 1996, Humana Press, Totowa, N.J.). For example, linear epitopes can be determined by, e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci. USA* 81:3998-4002; Geysen et al. (1986) *Molec. Immunol.* 23:709-715.

Similarly, conformational epitopes can be readily identified by determining spatial conformation of amino acids such as by, e.g., x-ray crystallography and 2-dimensional nuclear magnetic resonance. Antigenic regions of proteins can also be identified using standard antigenicity and hydropathy plots, such as those calculated using, e.g., the Omiga version 1.0 software program available from the Oxford Molecular Group. This computer program employs the Hopp/Woods method (Hopp et al., *Proc. Natl. Acad. Sci USA* (1981) 78:3824-3828) for determining antigenicity profiles and the Kyte-Doolittle technique (Kyte et al., *J. Mol. Biol.* (1982) 157:105-132) for hydropathy plots.

Generally, T-cell epitopes that are involved in stimulating the cellular arm of a subject's immune system are short peptides of about 8-25 amino acids. A common way to identify T-cell epitopes is to use overlapping synthetic peptides and analyze pools of these peptides, or the individual ones, that are recognized by T cells from animals that are immune to the antigen of interest, using, for example, an enzyme-linked immunospot assay (ELISPOT). These overlapping peptides can also be used in other assays such as the stimulation of cytokine release or secretion, or evaluated by constructing major histocompatibility (MHC) tetramers containing the peptide. Such immunogenically active fragments can also be identified based on their ability to stimulate lymphocyte proliferation in response to stimulation by various fragments from the antigen of interest.

The present invention can be practiced for prophylactic, therapeutic and/or diagnostic purposes. In addition, the invention can be practiced to produce antibodies for any purpose, such as diagnostic or research purposes, or for passive immunization by transfer to another subject.

The present invention further provides a kit comprising one or more compositions of this invention. It would be well understood by one of ordinary skill in the art that the kit of this invention can comprise one or more containers and/or receptacles to hold the reagents (e.g., antibodies, antigens, nucleic acids) of the kit, along with appropriate buffers and/or diluents and/or other solutions and directions for using the kit, as would be well known in the art. Such kits can further comprise adjuvants and/or other immunostimulatory or immunomodulating agents, as are well known in the art.

The compositions and kits of the present invention can also include other medicinal agents, pharmaceutical agents, carriers, diluents, immunostimulatory cytokines, etc. Actual methods of preparing such dosage forms are known, or will be apparent, to those skilled in this art.

Administration to a subject can be by any route known in the art. As non-limiting examples, the route of administration can be by inhalation (e.g., oral and/or nasal inhalation), oral, buccal (e.g., sublingual), rectal, vaginal, topical (including administration to the airways), intraocular, transdermal, by parenteral (e.g., intramuscular [e.g., administration to skeletal muscle], intravenous, intra-arterial, intraperitoneal and the like), subcutaneous (including administration into the footpad), intradermal, intrapleural, intracerebral, and/or intrathecal routes.

The epitopes, polypeptides, VLPs and viral vectors of the invention can be delivered per se or by delivering a nucleic acid (e.g., DNA) that encodes the same.

Immunomodulatory compounds, such as immunomodulatory chemokines and cytokines (preferably, CTL inductive cytokines) can be administered concurrently to a subject.

Cytokines may be administered by any method known in the art. Exogenous cytokines may be administered to the subject, or alternatively, a nucleic acid encoding a cytokine may be delivered to the subject using a suitable vector, and the cytokine produced in vivo. In particular embodiments, a viral adjuvant expresses the cytokine.

In embodiments of the invention, multiple dosages (e.g., two, three or more) of a composition of the invention can be administered without detectable pathogenicity (e.g., Dengue Shock Syndrome/Dengue Hemorrhagic Fever).

In embodiments of the invention, the multivalent vaccines of the invention do not result in immune interference, e.g., a balanced immune response is induced against all antigens presented. In embodiments of the invention, the balanced response results in protective immunity against DEN1, DEN2, DEN3 and DEN4.

In embodiments of the invention, the multivalent vaccine can be administered to a subject that has anti-dengue maternal antibodies present.

It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

As used herein, "a," "an" or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount of dose (e.g., an amount of a fatty acid) and the like, is meant to encompass variations of ±20%, ±10%, ±5%, ±1%, ±0.5%, or even ±0.1% of the specified amount.

As used herein, the transitional phrase "consisting essentially of" means that the scope of a claim is to be interpreted to encompass the specified materials or steps recited in the claim, "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP §2111.03. Thus, the term "consisting essentially of" when used in a claim of this invention is not intended to be interpreted to be equivalent to "comprising."

As used herein, the term "nucleic acid" encompasses both RNA and DNA, including cDNA, genomic DNA, synthetic (e.g., chemically synthesized) DNA and chimeras of RNA and DNA. The nucleic acid may be double-stranded or single-stranded. The nucleic acid may be synthesized using nucleotide analogs or derivatives (e.g., inosine or phosphorothioate nucleotides). Such nucleotides can be used, for example, to prepare nucleic acids that have altered base-pairing abilities or increased resistance to nucleases.

As used herein, the term "polypeptide" encompasses both peptides and proteins (including fusion proteins), unless indicated otherwise.

A "fusion protein" is a polypeptide produced when two heterologous nucleotide sequences or fragments thereof coding for two (or more) different polypeptides not found fused together in nature are fused together in the correct translational reading frame.

A "recombinant" nucleic acid, polynucleotide or nucleotide sequence is one produced by genetic engineering techniques.

A "recombinant" polypeptide is produced from a recombinant nucleic acid, polypeptide or nucleotide sequence.

As used herein, an "isolated" polynucleotide (e.g., an "isolated nucleic acid" or an "isolated nucleotide sequence") means a polynucleotide at least partially separated from at least some of the other components of the naturally occurring organism or virus, for example, the cell or viral structural components or other polypeptides or nucleic acids commonly found associated with the polynucleotide. Optionally, but not necessarily, the "isolated" polynucleotide is present at a greater concentration (i.e., is enriched) as compared with the starting material (e.g., at least about a two-fold, three-fold, four-fold, ten-fold, twenty-fold, fifty-fold, one-hundred-fold, five-hundred-fold, one thousand-fold, ten thousand-fold or greater concentration). In representative embodiments, the isolated polynucleotide is at least about 1%, 5%, 10%, 20%, 30%, 40%, 50%, 60%, 70%, 80%, 90%, 95% or more pure.

An "isolated" polypeptide means a polypeptide that is at least partially separated from at least some of the other components of the naturally occurring organism or virus, for example, the cell or viral structural components or other polypeptides or nucleic acids commonly found associated with the polypeptide. Optionally, but not necessarily, the "isolated" polypeptide is present at a greater concentration (i.e., is enriched) as compared with the starting material (e.g., at least about a two-fold, three-fold, four-fold, ten-fold, twenty-fold, fifty-fold, one-hundred-fold, five-hundred-fold, one thousand-fold, ten thousand-fold or greater concentration). In representative embodiments, the isolated polypeptide is at least about 1%, 5%, 10%, 20%, 30%, 40%, 50%, 60%, 70%, 80%, 90%, 95% or more pure.

Furthermore, an "isolated" cell is a cell that has been partially or completely separated from other components with which it is normally associated in nature. For example, an isolated cell can be a cell in culture medium and/or a cell in a pharmaceutically acceptable carrier.

The terms "immunogen" and "antigen" are used interchangeably herein and mean any compound (including polypeptides) to which a cellular and/or humoral immune response can be directed. In particular embodiments, an immunogen or antigen can induce a protective immune response against the effects of dengue virus infection.

"Effective amount" as used herein refers to an amount of a vector, nucleic acid, epitope, polypeptide, cell, composition or formulation of the invention that is sufficient to produce a desired effect, which can be a therapeutic and/or beneficial effect. The effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an "effective amount" in any individual case can be determined by one of ordinary skill in the art by reference to the pertinent texts and literature and/or by using routine experimentation.

The term "immunogenic amount" or "effective immunizing dose," as used herein, unless otherwise indicated, means an amount or dose sufficient to induce an immune response (which can optionally be a protective response) in the treated subject that is greater than the inherent immunity of non-immunized subjects. An immunogenic amount or effective immunizing dose in any particular context can be routinely determined using methods known in the art.

The terms "vaccine," "vaccination" and "immunization" are well-understood in the art, and are used interchangeably herein. For example, the terms vaccine, vaccination or immunization can be understood to be a process or composition that increases a subject's immune reaction to an immunogen (e.g., by providing an active immune response), and therefore its ability to resist, overcome and/or recover from infection (i.e., a protective immune response).

By the term "treat," "treating" or "treatment of" (and grammatical variations thereof) it is meant that the severity of the subject's condition is reduced, at least partially improved or ameliorated and/or that some alleviation, mitigation or decrease in at least one clinical symptom is achieved and/or there is a delay in the progression of the disease or disorder. In representative embodiments, the term "treat,", "treating" or "treatment of" (and grammatical variations thereof) refer to a reduction in the severity of viremia and/or a delay in the progression of viremia, with or without other signs of clinical disease.

A "treatment effective" amount as used herein is an amount that is sufficient to treat (as defined herein) the subject. Those skilled in the art will appreciate that the therapeutic effects need not be complete or curative, as long as some benefit is provided to the subject.

The term "prevent," "preventing" or "prevention of" (and grammatical variations thereof) refer to prevention and/or delay of the onset and/or progression of a disease, disorder and/or a clinical symptom(s) in a subject and/or a reduction in the severity of the onset and/or progression of the disease, disorder and/or clinical symptom(s) relative to what would occur in the absence of the methods of the invention. In representative embodiments, the term "prevent,", "preventing" or "prevention of" (and grammatical variations thereof) refer to prevention and/or delay of the onset and/or progression of viremia in the subject, with or without other signs of clinical disease. The prevention can be complete, e.g., the total absence of the disease, disorder and/or clinical symptom(s). The prevention can also be partial, such that the occurrence of the disease, disorder and/or clinical symptom(s) in the subject and/or the severity of onset and/or the progression is less than what would occur in the absence of the present invention.

A "prevention effective" amount as used herein is an amount that is sufficient to prevent (as defined herein) the disease, disorder and/or clinical symptom in the subject. Those skilled in the art will appreciate that the level of prevention need not be complete, as long as some benefit is provided to the subject.

The efficacy of treating and/or preventing dengue virus infection by the methods of the present invention can be determined by detecting a clinical improvement as indicated by a change in the subject's symptoms and/or clinical parameters (e.g., viremia), as would be well known to one of skill in the art.

Unless indicated otherwise, the terms "protect," "protecting," "protection" and "protective" (and grammatical variations thereof) encompass both methods of preventing and treating dengue virus infection in a subject, whether against one or multiple strains, genotypes or serotypes of dengue virus.

The terms "protective" immune response or "protective" immunity as used herein indicates that the immune response confers some benefit to the subject in that it prevents or reduces the incidence and/or severity and/or duration of disease or any other manifestation of infection. For example, in representative embodiments, a protective immune response or protective immunity results in reduced viremia, whether or not accompanied by clinical disease. Alternatively, a protective immune response or protective immunity may be useful in the therapeutic treatment of existing disease.

An "active immune response" or "active immunity" is characterized by "participation of host tissues and cells after an encounter with the immunogen. It involves differentiation and proliferation of immunocompetent cells in lymphoreticular tissues, which lead to synthesis of antibody or the development of cell-mediated reactivity, or both." Herbert B. Herscowitz, *Immunophysiology: Cell Function and Cellular Interactions in Antibody Formation*, in IMMUNOLOGY: BASIC PROCESSES 117 (Joseph A. Bellanti ed., 1985). Alternatively stated, an active immune response is mounted by the host after exposure to immunogens by infection or by vaccination. Active immunity can be contrasted with passive immunity, which is acquired through the "transfer of preformed substances (antibody, transfer factor, thymic graft, interleukin-2) from an actively immunized host to a non-immune host." Id.

A "subject" of the invention includes any animal susceptible to dengue virus infection. Such a subject is generally a mammalian subject (e.g., a laboratory animal such as a rat, mouse, guinea pig, rabbit, primates, etc.), a farm or commercial animal (e.g., a cow, horse, goat, donkey, sheep, etc.), or a domestic animal (e.g., cat, dog, ferret, etc.). In particular embodiments, the subject is a primate subject, a non-human primate subject (e.g., a chimpanzee, baboon, monkey, gorilla, etc.) or a human. Subjects of the invention can be a subject known or believed to be at risk of infection by dengue virus. Alternatively, a subject according to the invention can also include a subject not previously known or suspected to be infected by dengue virus or in need of treatment for dengue virus infection.

Subjects may be treated for any purpose, such as for eliciting a protective immune response or for eliciting the production of antibodies in that subject, which antibodies can be collected and used for other purposes such as research or diagnostic purposes or for administering to other subjects to produce passive immunity therein, etc.

Subjects include males and/or females of any age, including neonates, juvenile, mature and geriatric subjects. With respect to human subjects, in representative embodiments, the subject can be an infant (e.g., less than about 12 months, 10 months, 9 months, 8 months, 7 months, 6 months, or younger), a toddler (e.g., at least about 12, 18 or 24 months and/or less than about 36, 30 or 24 months), or a child (e.g., at least about 1, 2, 3, 4 or 5 years of age and/or less than about 14, 12, 10, 8, 7, 6, 5, or 4 years of age). In embodiments of the invention, the subject is a human subject that is from about 0 to 3, 4, 5, 6, 9, 12, 15, 18, 24, 30, 36, 48 or 60 months of age, from about 3 to 6, 9, 12, 15, 18, 24, 30, 36, 48 or 60 months of age, from about 6 to 9, 12, 15, 18, 24, 30, 36, 48 or 60 months of age, from about 9 to 12, 15, 18, 24, 30, 36, 48 or 60 months of age, from about 12 to 18, 24, 36, 48 or 60 months of age, from about 18 to 24, 30, 36, 48 or 60 months of age, or from about 24 to 30, 36, 48 or 60 months of age.

In embodiments of the invention, the subject has maternal antibodies to dengue virus.

A "subject in need" of the methods of the invention can be a subject known to be, or suspected of being, infected with, or at risk of being infected with, dengue virus.

Pharmaceutical formulations (e.g., immunogenic formulation) comprising the dengue virus epitopes, polypeptides, chimeric flavivirus VLPs or chimeric flavivirus particles, nucleic acids, vectors, cells or compositions of the invention and a pharmaceutically acceptable carrier are also provided, and can be formulated for administration in a pharmaceutical carrier in accordance with known techniques. See, e.g., Remington, *The Science And Practice of Pharmacy* (latest edition). In the manufacture of a pharmaceutical composition according to embodiments of the present invention, the composition of the invention is typically admixed with, inter alia, a pharmaceutically acceptable carrier. By "pharmaceutically acceptable carrier" is meant a carrier that is compatible with other ingredients in the pharmaceutical composition and that is not harmful or deleterious to the subject. The carrier may be a solid or a liquid, or both, and is preferably formulated with the composition of the invention as a unit-dose formulation, for example, a tablet, which may contain from about 0.01 or 0.5% to about 95% or 99% by weight of the composition. The pharmaceutical compositions are prepared by any of the well-known techniques of pharmacy including, but not limited to, admixing the components, optionally including one or more accessory ingredients. In certain embodiments, the pharmaceutically acceptable carrier is sterile and would be deemed suitable for administration into human subjects according to regulatory guidelines for pharmaceutical compositions comprising the carrier.

Furthermore, a "pharmaceutically acceptable" component such as a salt, carrier, excipient or diluent of a composition according to the present invention is a component that (i) is compatible with the other ingredients of the composition in that it can be combined with the compositions of the present invention without rendering the composition unsuitable for its intended purpose, and (ii) is suitable for use with subjects as provided herein without undue adverse side effects (such as toxicity, irritation, and allergic response). Side effects are "undue" when their risk outweighs the benefit provided by the composition. Non-limiting examples of pharmaceutically acceptable components include any of the standard pharmaceutical carriers such as phosphate buffered saline solutions, water, emulsions such as oil/water emulsion, microemulsions and various types of wetting agents.

In some embodiments, the compositions of the invention can further comprise one or more than one adjuvant. The adjuvants of the present invention can be in the form of an amino acid sequence, and/or in the form or a nucleic acid encoding an adjuvant. When in the form of a nucleic acid, the adjuvant can be a component of a nucleic acid encoding the polypeptide(s) or fragment(s) or epitope(s) and/or a separate component of the composition comprising the nucleic acid encoding the polypeptide(s) or fragment(s) or epitope(s) of the invention. According to the present invention, the adjuvant can also be an amino acid sequence that is a peptide, a protein fragment or a whole protein that functions as an adjuvant, and/or the adjuvant can be a nucleic acid encoding a peptide, protein fragment or whole protein that functions as an adjuvant. As used herein, "adjuvant" describes a substance, which can be any immunomodulating substance capable of being combined with a composition of the invention to enhance, improve or otherwise modulate an immune response in a subject.

In further embodiments, the adjuvant can be, but is not limited to, an immunostimulatory cytokine (including, but not limited to, GM/CSF, interleukin-2, interleukin-12, interferon-gamma, interleukin-4, tumor necrosis factor-alpha, interleukin-1, hematopoietic factor flt3L, CD40L, B7.1 co-stimulatory molecules and B7.2 co-stimulatory molecules), SYNTEX adjuvant formulation 1 (SAF-1) composed of 5 percent (wt/vol) squalene (DASF, Parsippany, N.J.), 2.5 percent Pluronic, L121 polymer (Aldrich Chemical, Milwaukee), and 0.2 percent polysorbate (Tween 80, Sigma) in phosphate-buffered saline. Suitable adjuvants also include an aluminum salt such as aluminum hydroxide gel (alum), aluminum phosphate, or algannmulin, but may also be a salt of calcium, iron or zinc, or may be an insoluble suspension of acylated tyrosine, or acylated sugars, cationically or anionically derivatized polysaccharides, or polyphosphazenes.

Other adjuvants are well known in the art and include without limitation MF 59, LT-K63, LT-R72 (Pal et al., *Vaccine* 24(6):766-75 (2005)), QS-21, Freund's adjuvant (complete and incomplete), aluminum hydroxide, N-acetyl-muramyl-L-threonyl-D-isoglutamine (thr-MDP), N-acetyl-normuramyl-L-alanyl-D-isoglutamine (CGP 11637, referred to as nor-MDP), N-acetylmuramyl-L-alanyl-D-isoglutami-nyl-L-alanine-2-(1'-2'-dipalmitoyl-sn-glycero-3-hydroxy-phosphoryloxy)-ethylamine (CGP 19835A, referred to as MTP-PE) and RIBI, which contains three components extracted from bacteria, monophosphoryl lipid A, trealose dimycolate and cell wall skeleton (MPL+TDM+CWS) in 2% squalene/Tween 80 emulsion.

Additional adjuvants can include, for example, a combination of monophosphoryl lipid A, preferably 3-de-O-acy-lated monophosphoryl. lipid A (3D-MPL) together with an aluminum salt. An enhanced adjuvant system involves the combination of a monophosphoryl lipid A and a saponin derivative, particularly the combination of QS21 and 3D-MPL as disclosed in PCT publication number WO 94/00153, or a less reactogenic composition where the QS21 is quenched with cholesterol as disclosed in PCT publication number WO 96/33739. A particularly potent adjuvant formulation involving QS21 3D-MPL & tocopherol in an oil in water emulsion is described in PCT publication number WO 95/17210. In addition, the nucleic acid compositions of the invention can include an adjuvant by comprising a nucleotide sequence encoding the antigen and a nucleotide sequence that provides an adjuvant function, such as CpG sequences. Such CpG sequences, or motifs, are well known in the art.

An adjuvant for use with the present invention, such as, for example, an immunostimulatory cytokine, can be administered before, concurrent with, and/or within a few hours, several hours, and/or 1, 2, 3, 4, 5, 6, 7, 8, 9, and/or 10 days before and/or after the administration of a composition of the invention to a subject.

Furthermore, any combination of adjuvants, such as immunostimulatory cytokines, can be co-administered to the subject before, after and/or concurrent with the administration of an immunogenic composition of the invention. For example, combinations of immunostimulatory cytokines, can consist of two or more immunostimulatory cytokines, such as GM/CSF, interleukin-2, interleukin-12, interferon-gamma, interleukin-4, tumor necrosis factor-alpha, interleukin-1, hematopoietic factor flt3L, CD40L, B7.1 co-stimulatory molecules and B7.2 co-stimulatory molecules. The effectiveness of an adjuvant or combination of adjuvants can be determined by measuring the immune response produced in response to administration of a composition of this invention to a subject with and without the adjuvant or combination of adjuvants, using standard procedures, as described herein and as known in the art.

In embodiments of the invention, the adjuvant comprises an alphavirus adjuvant as described, for example in U.S. Pat. No. 7,862,829.

Boosting dosages can further be administered over a time course of days, weeks, months or years. In chronic infection, initial high doses followed by boosting doses may be advantageous.

The pharmaceutical formulations of the invention can optionally comprise other medicinal agents, pharmaceutical agents, stabilizing agents, buffers, carriers, diluents, salts, tonicity adjusting agents, wetting agents, and the like, for example, sodium acetate, sodium lactate, sodium chloride, potassium chloride, calcium chloride, sorbitan monolaurate, triethanolamine oleate, etc.

For injection, the carrier will typically be a liquid. For other methods of administration, the carrier may be either solid or liquid. For inhalation administration, the carrier will be respirable, and is typically in a solid or liquid particulate form.

The compositions of the invention can be formulated for administration in a pharmaceutical carrier in accordance with known techniques. See, e.g., Remington, The Science And Practice of Pharmacy ($9^{th}$ Ed. 1995). In the manufacture of a pharmaceutical composition according to the invention, the VLPs are typically admixed with, inter alia, an acceptable carrier. The carrier can be a solid or a liquid, or both, and is optionally formulated with the compound as a unit-dose formulation, for example, a tablet. A variety of pharmaceutically acceptable aqueous carriers can be used, e.g., water, buffered water, 0.9% saline, 0.3% glycine, hyaluronic acid, pyrogen-free water, pyrogen-free phosphate-buffered saline solution, bacteriostatic water, or Cremophor EL[R] (BASF, Parsippany, N.J.), and the like. These compositions can be sterilized by conventional techniques. The formulations of the invention can be prepared by any of the well-known techniques of pharmacy.

The pharmaceutical formulations can be packaged for use as is, or lyophilized, the lyophilized preparation generally being combined with a sterile aqueous solution prior to administration. The compositions can further be packaged in unit/dose or multi-dose containers, for example, in sealed ampoules and vials.

The pharmaceutical formulations can be formulated for administration by any method known in the art according to conventional techniques of pharmacy. For example, the compositions can be formulated to be administered intranasally, by inhalation (e.g., oral inhalation), orally, buccally (e.g., sublingually), rectally, vaginally, topically, intrathecally, intraocularly, transdermally, by parenteral administration (e.g., intramuscular [e.g., skeletal muscle], intravenous, subcutaneous, intradermal, intrapleural, intracerebral and intra-arterial, intrathecal), or topically (e.g., to both skin and mucosal surfaces, including airway surfaces).

For intranasal or inhalation administration, the pharmaceutical formulation can be formulated as an aerosol (this term including both liquid and dry powder aerosols). For example, the pharmaceutical formulation can be provided in a finely divided form along with a surfactant and propellant. Typical percentages of the composition are 0.01-20% by weight, preferably 1-10%. The surfactant is generally non-toxic and soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1-20% by weight of the composition, preferably 0.25-5%. The balance of the composition is ordinarily propellant. A carrier can also be included, if desired, as with lecithin for intranasal delivery. Aerosols of liquid particles can be produced by any suitable means, such as with a pressure-driven aerosol nebulizer or an ultrasonic nebulizer, as is known to those of skill in the art. See, e.g., U.S. Pat. No. 4,501,729. Aerosols of solid particles can likewise be produced with any solid particulate medicament aerosol generator, by techniques known in the pharmaceutical art. Intranasal administration can also be by droplet administration to a nasal surface.

Injectable formulations can be prepared in conventional forms, either as liquid solutions or suspensions, solid forms suitable for solution or suspension in liquid prior to injection, or as emulsions. Alternatively, one can administer the pharmaceutical formulations in a local rather than systemic manner, for example, in a depot or sustained-release formulation.

Extemporaneous injection solutions and suspensions can be prepared from sterile powders, granules and tablets of the kind previously described. For example, an injectable, stable, sterile formulation of the invention in a unit dosage form in a sealed container can be provided. The formulation can be provided in the form of a lyophilizate, which can be reconstituted with a suitable pharmaceutically acceptable carrier to form a liquid composition suitable for injection into a subject. The unit dosage form can be from about 1 µg to about 10 grams of the formulation. When the formulation is substantially water-insoluble, a sufficient amount of emulsifying agent, which is pharmaceutically acceptable, can be included in sufficient quantity to emulsify the formulation in an aqueous carrier. One such useful emulsifying agent is phosphatidyl choline.

Pharmaceutical formulations suitable for oral administration can be presented in discrete units, such as capsules, cachets, lozenges, or tables, as a powder or granules; as a solution or a suspension in an aqueous or non-aqueous liquid; or as an oil-in-water or water-in-oil emulsion. Oral delivery can be performed by complexing a compound(s) of the present invention to a carrier capable of withstanding degradation by digestive enzymes in the gut of an animal. Examples of such carriers include plastic capsules or tablets, as known in the art. Such formulations are prepared by any suitable method of pharmacy, which includes the step of bringing into association the protein(s) and a suitable carrier (which may contain one or more accessory ingredients as noted above). In general, the pharmaceutical formulations are prepared by uniformly and intimately admixing the compound(s) with a liquid or finely divided solid carrier, or both, and then, if necessary, shaping the resulting mixture. For example, a tablet can be prepared by compressing or molding a powder or granules, optionally with one or more accessory ingredients. Compressed tablets are prepared by compressing, in a suitable machine, the formulation in a free-flowing form, such as a powder or granules optionally mixed with a binder, lubricant, inert diluent, and/or surface active/dispersing agent(s). Molded tablets are made by molding, in a suitable machine, the powdered protein moistened with an inert liquid binder.

Pharmaceutical formulations suitable for buccal (sublingual) administration include lozenges comprising the compound(s) in a flavored base, usually sucrose and acacia or tragacanth; and pastilles in an inert base such as gelatin and glycerin or sucrose and acacia.

Pharmaceutical formulations suitable for parenteral administration can comprise sterile aqueous and non-aqueous injection solutions, which preparations are preferably isotonic with the blood of the intended recipient. These preparations can contain anti-oxidants, buffers, bacteriostats and solutes, which render the composition isotonic with the blood of the intended recipient. Aqueous and non-aqueous sterile suspensions, solutions and emulsions can include suspending agents and thickening agents. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Pharmaceutical formulations suitable for rectal administration are optionally presented as unit dose suppositories. These can be prepared by admixing the active agent with one or more conventional solid carriers, such as for example, cocoa butter and then shaping the resulting mixture.

Pharmaceutical formulations suitable for topical application to the skin preferably take the form of an ointment, cream, lotion, paste, gel, spray, aerosol, or oil. Carriers that can be used include, but are not limited to, petroleum jelly, lanoline, polyethylene glycols, alcohols, transdermal enhancers, and combinations of two or more thereof. In some embodiments, for example, topical delivery can be performed by mixing a pharmaceutical formulation of the present invention with a lipophilic reagent (e.g., DMSO) that is capable of passing into the skin.

Pharmaceutical formulations suitable for transdermal administration can be in the form of discrete patches adapted to remain in intimate contact with the epidermis of the subject for a prolonged period of time. Formulations suitable for transdermal administration can also be delivered by iontophoresis (see, for example, *Pharmaceutical Research* 3:318 (1986)) and typically take the form of a buffered aqueous solution of the compound(s). Suitable formulations can comprise citrate or bis\tris buffer (pH 6) or ethanol/water and can contain from 0.1 to 0.2M active ingredient.

In embodiments of the invention, the dosage of a virus particle of this invention can be in a range of about $10^4$ to about $10^7$ plaque forming units (PFUs). In embodiments of this invention, the dosage of a VLP of this invention can be in a range of about 500 micrograms to about 5 milligrams. In embodiments of this invention, the dosage of a protein of this invention can be in a range of about $10^0$ to about $10^4$ micrograms+/−adjuvant.

Further, the composition can be formulated as a liposomal formulation. The lipid layer employed can be of any conventional composition and can either contain cholesterol or can be cholesterol-free. The liposomes that are produced can be reduced in size, for example, through the use of standard sonication and homogenization techniques.

The liposomal formulations can be lyophilized to produce a lyophilizate which can be reconstituted with a pharmaceutically acceptable carrier, such as water, to regenerate a liposomal suspension.

The immunogenic formulations of the invention can optionally be sterile, and can further be provided in a closed pathogen-impermeable container.

Example 1: Identification of Human Neutralizing Antibodies that Bind to Complex Epitopes of Dengue Virions Serum Samples.

Human serum samples were collected from individuals who had experienced a DENV infection during travel to an endemic region. Rhesus macaque (*Macaca mulatta*) sera were taken from animals vaccinated with a VEEV replicon particle (VRP-rE) expressing 80% of DENV3 E protein. More information is provided in SI Methods.

Virus and rE Proteins.

The DENV1 (West Pac 74), DENV2 (S-16803), DENV3 (CH-53489 and Thailand 95), and DENV4 (TVP-360) strains were used in the present study. All viruses used in the neutralization assays were grown in C6/36 *Aedes albopictus* mosquito cells at 28° C. and titered on Vero-81 cells as previously described (15). DENV was purified as previously described (42). The rE proteins from each of the four DENV serotypes were purchased from Hawaii Biotech, Inc.

Depletion of DENV-Specific Abs from Human Immune Sera.

Purified DENVs were adsorbed onto 4.0 µm Polybead polystyrene microspheres following the manufacturer's instructions (Polysciences, Inc.). Control beads were adsorbed with BSA instead. Human immune sera were depleted of virus-specific Abs by incubating sera with virus-adsorbed beads at 37° C. Detailed information is given in SI Methods.

Depletion of DENV rE-Specific Abs from Human and Monkey Immune Sera.

DENV rE proteins were covalently conjugated to cyanogen bromide (CNBr)-activated beads following the manufacturer's protocol (Sigma). Control beads were conjugated with the blocking reagent instead of rE protein. DENV rE-specific Abs were depleted by incubating human and rhesus macaque immune sera with rE-conjugated beads at 37° C. Detailed information is given in SI Methods.

Detection of DENV or rE-Binding Abs by ELISA.

ELISAs were conducted as previously described (5). Sera were used at dilutions of 1:40 and 1:25 for the depletion confirmation ELISAs in the virus and rE depletion experiments, respectively. More information is provided in SI Methods.

Detection of rE-Binding by Western Blot.

Detailed information is provided in SI Methods.

SI Methods

Serum Samples.

Human blood donor recruitment and sample collection were in compliance with the Institutional Review Board of the University of North Carolina at Chapel Hill. All individuals were informed, and written consent was obtained before blood donation. The rhesus macaques (~7 y of age) were vaccinated with a VEEV replicon particle (VRP-rE) expressing amino acids 1-424 of DENV3 E ectodomain (85% of full-length E protein, also designated as E85), boosted at 7 wk. The serum used for the present experiments was collected at 3 wk after the boost.

Depletion of DENV-Specific Abs from Human Immune Sera.

Beads were washed three times with 0.1 M borate buffer (pH 8.5) and incubated with the relevant purified DENV in borate buffer overnight at room temperature (RT). Control beads were incubated overnight with an equivalent amount of BSA. The control and virus-adsorbed beads were blocked with BSA (10 mg/mL) in borate buffer for 30 min at RT three times and washed six times with PBS. Human immune sera were depleted of virus-specific Abs by incubating sera with virus-adsorbed beads for 2 h at 37° C. with end-over-end mixing. Each immune serum was subjected to at least three sequential rounds of depletions before confirming successful removal of the respective Abs by coated (antigen directly coated on plate) and capture (antigen captured by the mouse MAb 4G2) ELISA.

Depletion of DENV rE-Specific Abs from Human and Monkey Immune Sera.

Cyanogen bromide (CNBr)-activated beads were covalently conjugated with rE protein following the manufacturer's protocol (Sigma). CNBr beads were washed four times with distilled water, followed by three additional washes with coupling buffer [0.1M NaHCO3, 0.5 M NaCl (pH 8.5)]. The relevant DENV rEprotein diluted in coupling buffer was incubated with CNBr-activated beads for 2 h at RT. Control beads were incubated longer with the blocking reagent instead of rE protein. The unreacted groups on the rE-conjugated beads and control beads were blocked and incubated with 0.2 M glycine (pH 8.0), washed three times with coupling buffer, and then washed four times with PBS. Human and rhesus macaque immune sera were incubated with rE conjugated beads for 2 h at 37° C. Each serum sample was subjected to at least three sequential rounds of Ab depletion before confirming successful removal of the respective Abs detectable by coated or capture ELISA.

Detection of DENV or rE-Binding Abs by ELISA.

ELISA plates were coated with either 50 ng per well of intact purified virus or 100 ng per well of rE protein in carbonate buffer (pH 9.6) for 2 h at RT. Plates were blocked with 3% (vol/vol) normal goat sera in Trisbuffered saline (TBS) containing 0.05% (vol/vol) Tween 20 (blocking buffer). Undepleted, control-depleted, and antigen depleted immune serum were diluted in blocking buffer and incubated on plates for 1 h at 37° C. Sera were used at dilutions of 1:40 and 1:25 for the depletion confirmation ELISAs in the virus and rE depletion experiments, respectively. DENV or rE reactive Abs were detected using an alkaline phosphatase-conjugated goat anti-human IgG secondary Ab and paranitrophenyl phosphate substrate as previously described (5).

Detection of rE-Binding Abs by Western Blot.

Purified DENV (700 ng per well) and DENV rE protein (500 ng per well) were diluted with nonreducing SDS sample buffer, loaded onto a 12% polyacrylamide SDS/PAGE gel, and electrophoresed. Viral proteins were transferred onto polyvinylidene fluoride membranes and blocked overnight at 4° C. with 5% (wt/vol) dried nonfat milk Membrane was then probed with immune sera (diluted 1:1,000) for 1 h at 37° C., washed three times with TBS containing 0.2% (vol/vol) Tween-20, incubated with a goat anti-human IgG-HRP secondary for 1 h at 37° C., washed three times, and developed using ECL substrate.

Measuring DENV Neutralization by Immune Sera and Monoclonal Antibodies.

Neutralizing activity of both immune sera and monoclonal antibodies were measured using a flow cytometry based neutralization assay with U937 monocytic cells stably transfected with dendritic cell-specific intercellular adhesion molecule-3-grabbing non-integrin (DC-SIGN) as previously described (15). Briefly, virus and antibody mixtures were pre-incubated for 1 hr at 37° C., prior to the addition of DC-SIGN expressing U937 cells (U937+DC-SIGN). After 2 hrs of incubation at 37° C. with virus-antibody immune complexes, cells were washed twice with infection media. Cells were fixed and permeabilized 24 hrs after infection, probed with 2H2 (anti-prM antibody) conjugated to 488 and infected cells quantified using a Guava flow-cytometer (Milipore).

Focus reduction neutralization assays (FRNT) were conducted using Vero-81 cells as described previously (15). Briefly, virus and serially diluted serum were pre-incubated for 1 hr at 37° C., incubated with Vero-81 cells (grown to 80% confluency) for 2 hrs at 37° C. and then overlaid with methylcellulose containing nutrient media. The cells were fixed at either day 3 (for DENV2 and DENV4) or day 4 (for DENV1 and DENV3) and stained for foci using the anti-E MAb, 4G2, and goat anti-mouse HRP and True blue substrate.

Generation of Anti-DENV hMAbs.

Supernatants from EBV-transformed lymphoblastoid cell lines were screened for binding to DENV by ELISA and, in some cases, tested for neutralization of DENV using a flow cytometry-based assay. Positive wells were fused with HMMA2.5 myeloma cells to generate hybridoma lines as previously described (33, 43). Hybridoma lines then were biologically cloned and grown in serum-free medium (no. 12045084, Gibco Hybridoma-SFM; Invitrogen), and hMAbs were purified using protein G chromatography.

Generation and Characterization of hMAb Neutralization Escape Mutant Viruses.

Virus-Ab mixtures were added to Vero cells and passaged every 3-5 d in the presence of Ab to enrich for escape mutant viruses. Virus growth in the presence of Ab was monitored by quantitative RT-PCR and by immunofluorescent detection of DENV antigens in cell monolayers. Following four to six passages under Ab selection, the capsid, prM, and E genes of the escape variants were amplified by RT-PCR and sequenced to identify mutations associated with the Ab escape phenotype.

Statistical Analysis.

Sigmoidal binding and neutralization curves were compared between undepleted, control-depleted, and virus-depleted or rE-depleted groups using a one-way ANOVA analysis, followed by a Tukey multiple comparison test at P<0.05. The one-dilution binding data (represented in bar charts) for control-depleted and virus-depleted or rE-depleted samples were compared using an unpaired Student t test of means. All statistical analyses were conducted using GraphPad Prism4.

Depletion of Homologous DENV-Specific Abs from Immune Sera.

Studies were undertaken to characterize Abs in human immune sera responsible for potent and long-term neutralization of the homologous virus serotype. We assembled a panel of eight immune sera from healthy volunteers who had been exposed to primary DENV2 or DENV3 infections ~2-9 yrs before blood collection (Table 4). Human serum from individuals lacking a past history of DENV infections (confirmed by ELISA and neutralization assays) was used as a negative control.

To define the Ab subpopulation in immune sera responsible for DENV neutralization, we developed a bead-based technique to fractionate DENV-specific Abs in immune sera. Polystyrene beads coated with virions of the homologous serotype were incubated with immune sera at 37° C. to deplete DENV-binding Abs. Untreated and control-depleted serum samples bound to whole virus from each of the four DENV serotypes by ELISA and efficiently neutralized DENV (FIGS. 1A and 1B). Serum samples depleted using beads coated with the homologous DENV displayed greatly reduced binding and neutralization of DENV (FIGS. 1A and 1B), indicating that beads coated with the homologous serotype successfully removed most DENV-specific Abs from immune sera.

Depletion of Heterologous DENV-Specific Abs from Immune Sera.

Figure 4:
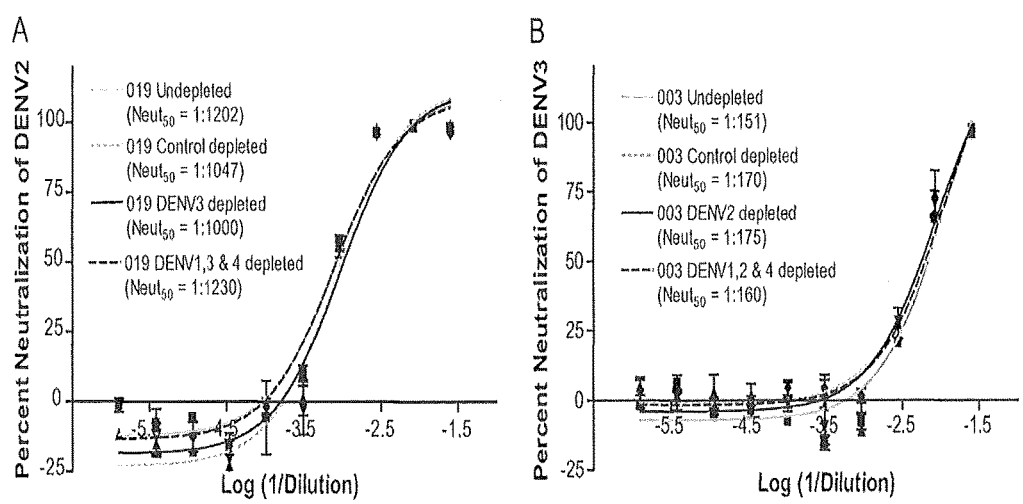
FIG. 4: Comparison of neutralization properties of primary DENV-immune human sera depleted with either one heterologous virus or all three heterologous viruses. (A) Depletion of primary DENV2-immune sera (e.g. subject 019) with DENV3 virus, or DENV1, 3, and 4 viruses, had no statistically significant effect on the $Neut_{50}$ against the homotypic virus, DENV2. (B) Depletion of primary DENV3-immune sera (e.g. subject 003) with DENV2 virus or DENV1, 2 and 4 viruses, had no statistically significant effect on the $Neut_{50}$ against DENV3. Data are representative of single experiments conducted in duplicate. The $Neut_{50}$ values of undepleted, control depleted and cross-reactive depleted sera were compared for each serum using one-way ANOVA analysis followed by a Tukey's multiple comparison test at $P<0.05$.

Next, we assessed the contribution of DENV cross-reactive Abs in immune sera to virus binding and neutralization. We used polystyrene beads coated with virus of a heterologous serotype (a serotype that has not infected the DENV-immune subject) to deplete cross-reactive Abs from primary immune sera (FIG. 1 and Table 1). Depletion of primary DENV2-immune sera with DENV3-coated beads led to the removal of all cross-reactive Abs, with the remaining Abs binding to DENV2 in a type-specific manner (FIG. 1C). Reciprocal depletion of primary DENV3-immune sera with DENV2-coated beads removed all binding to DENV2 and DENV4 but not to DENV3 and, to a lesser extent, DENV1 (FIG. 1E). This residual DENV1-binding signal may be attributable to Abs targeting sub-complex epitopes that are preferentially shared between DENV1 and DENV3 (11, 18, 36). Removal of cross-reactive Abs from primary immune sera did not change the capacity of the sera to neutralize the virus responsible for infection (FIGS. 1D and 1F, FIG. 4, and Table 1). These results demonstrate that the DENV-specific human Ab response consists of both cross-reactive and type-specific Abs. Although the serotype cross-reactive Abs were abundant, in the samples we analyzed, their contribution to neutralization was negligible. Thus, type-specific Abs appear to be primarily responsible for neutralizing the homologous serotype.

Depletion of DENV Recombinant E Protein-Binding Abs from Immune Sera.

Figure 2:
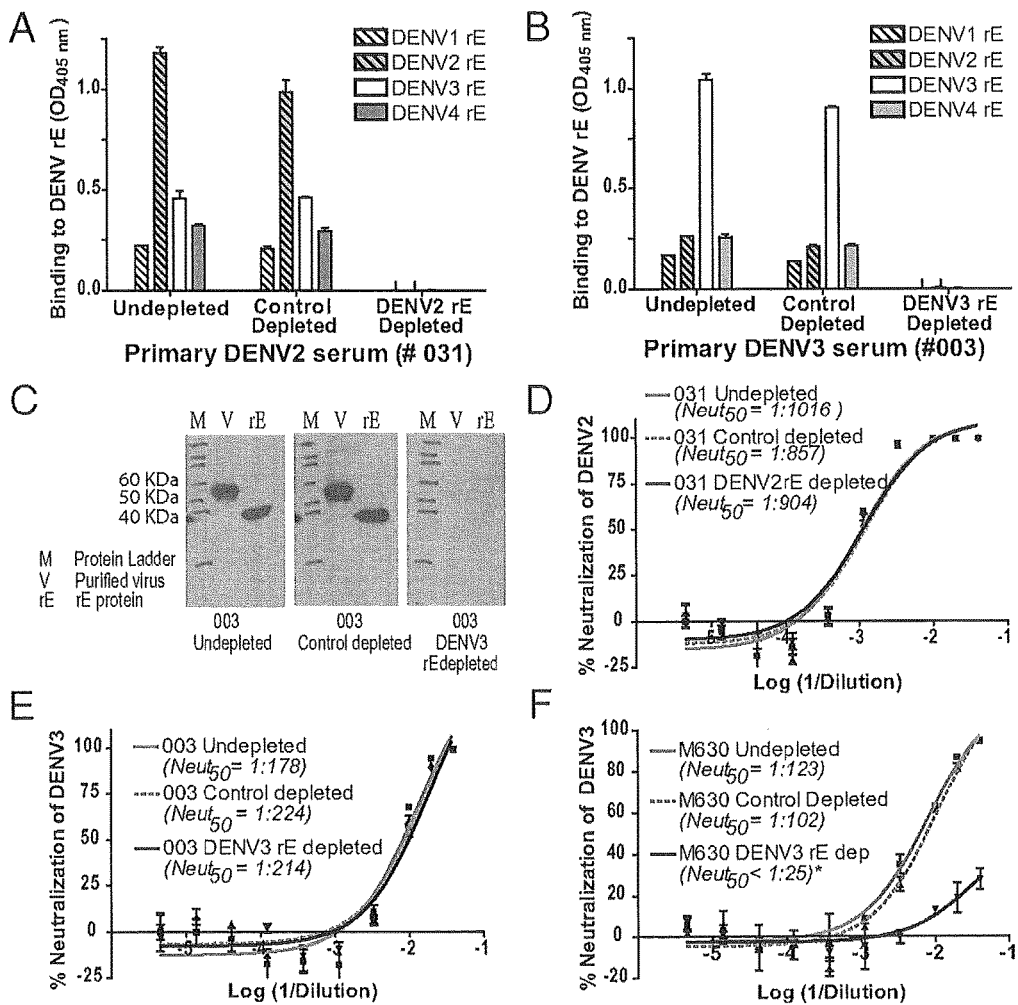
FIG. 2: Binding and neutralization properties of primary DENV-immune sera depleted of rE-binding Abs. DENV rE from the homotypic strain was coupled covalently to agarose beads and incubated with the relevant DENV-immune sera to deplete DENV rE-specific Abs. (A-B) Binding of immune sera to rE protein. (A) Primary DENV2 and (B) DENV3-immune sera were depleted with DENV2 and DENV3 rE protein respectively, and binding to rE protein from each of the four serotypes was measured by ELISA. Depletion with the rE from the homologous serotype led to a loss of binding to rE protein from each of the four serotypes. (C) Successful removal of all rE-reactive Abs from sera (e.g. primary DENV3-immune subject 003) also was confirmed by Western blot analysis. Purified homotypic DENV virus (700 ng/well) and rE protein (500 ng/well) were electrophoresed, transferred to nitrocellulose membrane and probed with undepleted, control depleted or rE-depleted sera (at 1:1000 dilution). (D-E) Neutralization of the homologous DENV virus by rE-depleted sera was measured using the U937+DC-SIGN flow cytometry-based assay. Homologous DENV neutralization by (D) primary DENV2 (subject 031), (E) primary DENV3 (subject 003)-human immune sera depleted of rE-binding Abs was tested. No reduction in neutralization potency was observed following removal of rE-binding Abs from either of these two serum samples. A total of six primary immune sera were depleted of rE-binding Abs and tested (see Table 2). (F) Non-human primates vaccinated with rE develop neutralizing Abs that can be depleted with rE antigen. Rhesus macaques (*Macaca mulatta*) were vaccinated and boosted with an alphavirus vector expressing DENV3 E ectodomain and sera were collected 10 weeks post-vaccination. Depletion of rE-binding Abs from sera of vaccinated animals (e.g. M630) removed greater than 98% (value estimated by comparing $Neut_{50}$ values between control depleted and rE depleted) of the neutralizing Abs. Data is representative of two vaccinated rhesus macaque controls.
Figure 5:
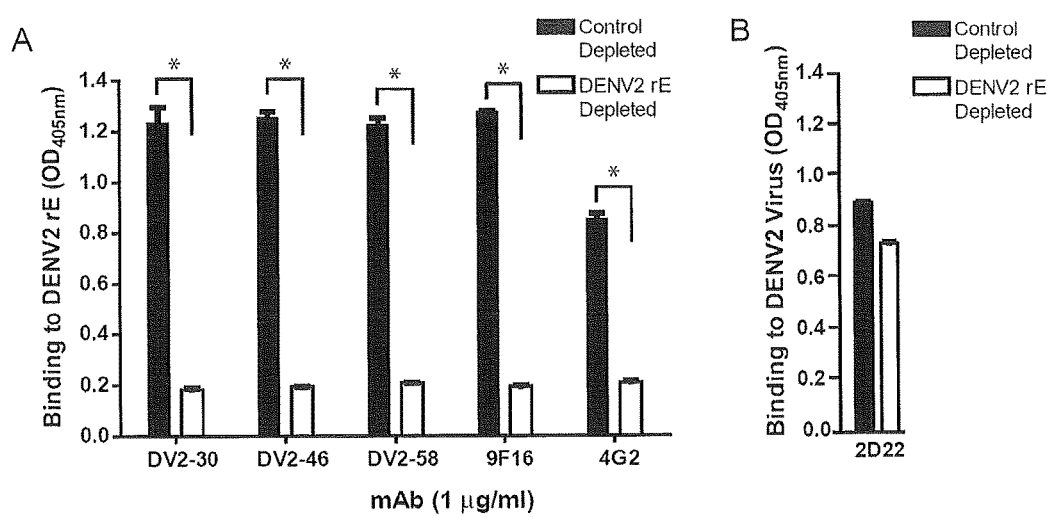
FIG. 5: Confirmation of the DENV2 rE structure on the CnBr-activated beads using mouse MAbs. Mouse MAbs, 9F16 (E DIII-specific) (12), 4G2 (fusion loop-specific), DV2-30, DV2-46, and DV2-58 (dimer interface-specific) (11), and human mAbs, 2D22 (virus-specific) were incubated three consecutive times with either control beads or DENV2 rE-conjugated beads for 2 hrs at 37° C. The depleted samples were tested for binding to DENV2 rE by capture ELISA. (A) All previously mapped mouse MAbs that bound epitopes on DENV rE protein were successfully depleted with rE protein covalently conjugated to beads. (B) The virus-specific human mAb, 2D22, was not depleted by rE protein. Data are representative of individual experiments conducted in duplicate. *$P<0.001$ by unpaired student t-test of mean binding values.
Figure 6:
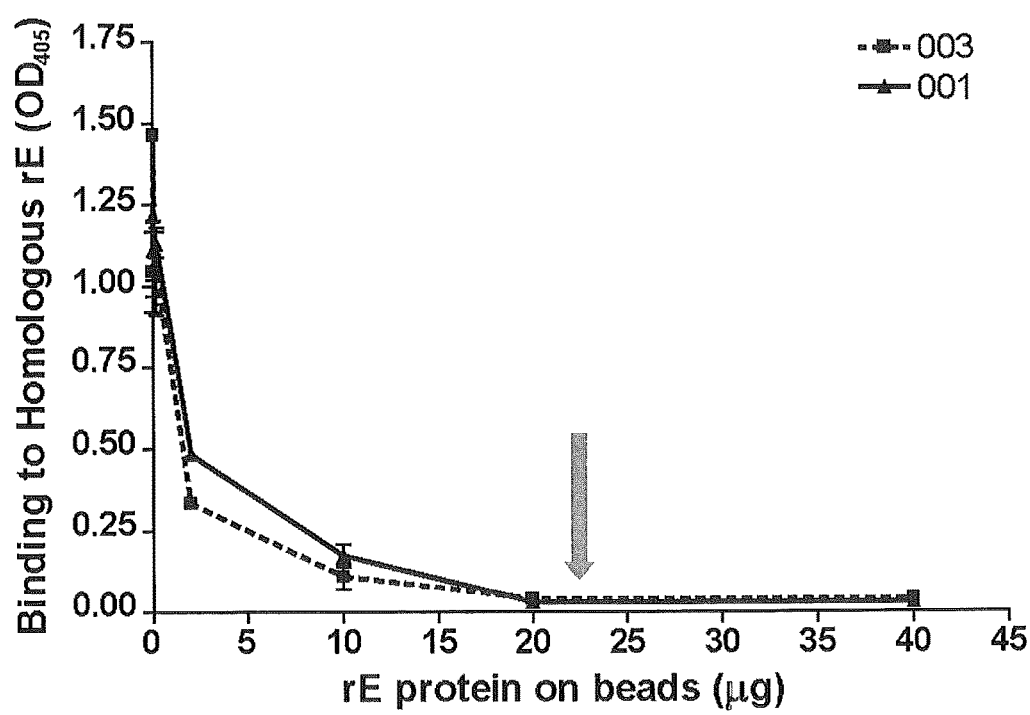
FIG. 6: Titration of DENV rE quantities that were covalently conjugated to beads. CnBr-activated beads were mixed with varying quantities (i.e. 0, 0.02, 0.2, 2, 10, 20 and 40 µg/ml) of DENV2 and DENV3 rE protein, and then incubated with primary DENV2 (i.e. subject 001) and DENV3 (i.e. subject 003) sera respectively. The remaining supernatant was tested for the presence of homologous rE-binding antibodies by capture ELISA. The grey arrow represents the amount of rE added to beads during ensuing rE depletion experiments with immune sera.
Figure 7:
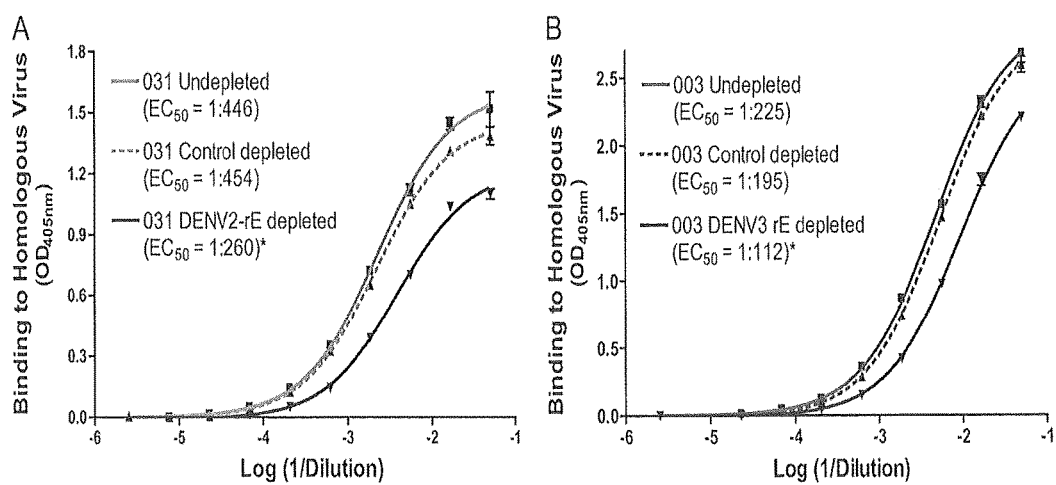
FIG. 7: Binding properties of rE-depleted sera to the homotypic DENV virus. Removal of rE-binding antibodies from (A) primary DENV2 and (B) DENV3 sera resulted in a statistically significant ($P<0.05$) 45±7% decrease in binding ($EC_{50}$) to the homologous virus. Statistical analysis was conducted using a one way ANOVA. Data are representative of three primary DENV2 and three primary DENV3 human immune sera (See Table 5).

The organization of DENV E protein dimers on the surface of the infectious virus has been modeled using crystal structures of DENV recombinant E (rE) and cryo-EM reconstructions of the virion (16, 17, 22, 44). Furthermore, neutralizing mouse MAbs have been mapped extensively to the rE protein, and DENV subunit vaccines using the rE protein are currently being developed (3, 4, 10, 11, 35-37, 39). We next assessed whether epitopes targeted by neutralizing Abs in human immune sera were preserved on the rE protein. DENV rE protein that was covalently coupled to agarose beads was used to deplete Abs in immune sera. Sera were incubated with either control beads or homologous rE-conjugated beads at 37° C. The structure of DENV rE on the beads was confirmed to be conformationally preserved, and rE dimers were confirmed to be intact by successfully depleting mouse MAbs previously mapped to the fusion loop (MAb 4G2), EDIII (MAb 9F16) (36), and E dimer interface (MAbs DV2-10, DV2-46, and DV2-58) (35) (FIG. 5). We also titrated the amount of rE protein on the beads required to deplete rE-binding Abs efficiently from immune sera (FIG. 6). Both untreated and control-depleted immune sera bound to rE from all four serotypes, but the binding was greatest for the homologous serotype (FIGS. 2A and 2B). Depletion of primary immune sera using homologous rE ablated binding to rE from each of the four serotypes (FIGS. 2A and 2B). Successful depletion of rE-binding Abs was also confirmed by Western blot, where rE and solubilized virions were used as the antigen on the blot (FIG. 2C). By Western blot, we could not detect binding to rE protein (which is missing 20% of the native protein at the C terminus) or to full-length E protein from the virus (FIG. 2C). These results established that beads coated with the rE from the homologous serotype efficiently removed all Abs recognizing purified rE protein. We also measured the relative proportion of virion-binding Abs in human immune sera that bound to rE by comparing the binding of untreated, control-depleted, and rE-depleted sera with the homologous virus by ELISA. Results demonstrated an approximate 45+7% reduction in DENV binding following the removal of rE-binding Abs (FIG. 7 and Table 5), indicating that approximately half of the DENV-specific Abs in primary immune sera recognized the intact virus but not rE protein. Next, we assessed the neutralizing activity of six immune sera depleted of rE-binding Abs. Unexpectedly, four of the six immune sera displayed no loss of neutralization potency after removal of rE-binding Abs (FIGS. 2D and 2E and Table 2). One of the three primary DENV2-immune sera and all three of the primary DENV3-immune sera tested displayed no significant loss of neutralization against the homotypic virus after removal of rE-specific Abs. In contrast, two of the three primary DENV2-immune sera displayed a statistically significant two- to threefold drop ($P<0.05$) in the 50% neutralization ($Neut_{50}$) titer when rE-specific Abs were removed (Table 2). Sera from rhesus macaques (*Macaca mulatta*) immunized with Venezuelan equine encephalitis virus (VEEV) replicons expressing DENV3 E85 protein were used as a positive control in these experiments. These animals should develop neutralizing Abs that bind to rE protein; accordingly, rE-coated beads removed >98% of the neutralizing Abs from these vaccine sera (FIG. 2F). We conclude that although there was some variation among human immune sera in the contribution of rE-reactive Abs to homotypic DENV neutralization, a large fraction of DENV neutralizing Abs in humans consists of neutralizing Abs that bind to intact virions but not the rE protein.

Characterization of hMAbs that Strongly Neutralize DENV.

As an alternate approach to identify neutralizing viral epitopes targeted by DENV-immune individuals, we generated a panel of hMAbs that strongly neutralized DENV. These Abs were generated by transforming memory B cells from DENV-immune subjects with EBV and generating hMAbs by electro-fusion as previously described (33). Because strongly neutralizing hMAbs comprise a minor fraction of the total hMAbs isolated from immune subjects (2, 6, 7), we used a two-step screen to isolate strongly inhibitory Abs: We first identified Abs that bound to DENV virions and then tested them for neutralizing activity. We isolated three strongly neutralizing type-specific hMAbs (Neut$_{50}$ value <0.2 µg/mL), designated 1F4, 2D22, and 5J7, that inhibited infection of DENV1, DENV2, and DENV3, respectively. Two of these hMAbs bound to the intact virus but not to rE (Table 3).

Generation of DENV Mutants that Escape Neutralization by hMAbs.

Figure 3:
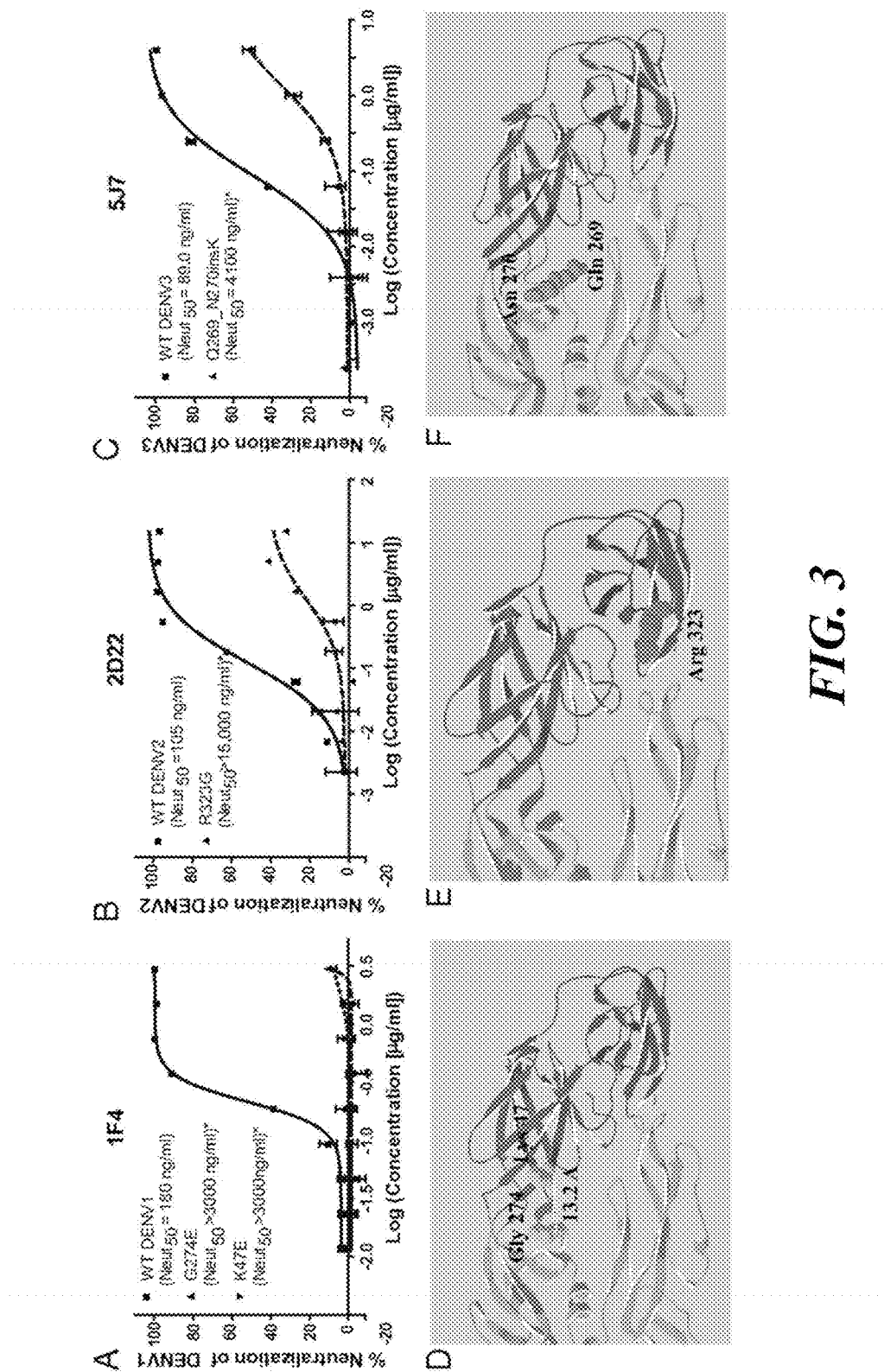
FIG. 3: Epitope mapping of escape mutants generated from type-specific neutralizing hMAbs. (A-C) Neutralization profiles of respective wild type (WT) and escape mutants against (A) 1F4, (B) 2D22 and (C) 5J7. Neutralization escape by the mutant viruses was confirmed using the U937+DC-SIGN flow cytometry-based neutralization assay for 1F4 and 2D22, and by FRNT for 5J7. (D-F) Display enlarged views indicating the positions of the original amino acids of the escape mutations on EDIII and EDI-EDII hinge region for 1F4 (D), 2D22 (E) and 5J7 (F). Images were generated with DENV1, DENV2 and DENV3 E dimer structure respectively. The DENV2 and DENV3 E dimer structures (RCSB accession no. 1OAN and 1UZG respectively) (8, 9) were modeled using Swiss PDB viewer and Pymol to generate structures for DENV1 and DENV3 (Thai 95) E dimers. (G) Alignment of E protein segments from DENV (SEQ ID NOS:1-3, 5-7, 9-11 and 13-15) and WNV (SEQ ID NOS: 4, 8, 12 and 16) identified in the neutralizing hMAb binding epitope of CR4354. Mutations leading to escape from 1F4 (blue), 2D22 (green) or 5J7 (pink) are highlighted on relevant regions of the aligned DENV E protein sequences. A portion of the CR4354 epitope that overlaps with the corresponding DENV escape mutations described here is highlighted in bold on the aligned WNV (New York 2000) sequence. H. The escape mutations were mapped on to the E polymeric structure generated for TBEV (RCSB accession no. 1K4R) (10). The position of escape mutations generated from 1F4, 2D22 and 5J7 are highlighted on the structure in blue (Gly274, K47), green (Arg323, His282, Asp362) and pink (Gln271, Asn272, i.e. residues surrounding the lysine insertion) respectively. The footprint of the anti-WNV CR4354 hMAb that spans E protein dimers is circled with a white line. Note that all escape mutations for 1F4, 2D22, and 5J7 fall within the CR4354 footprint. *$Neut_{50}$ values for each escape mutant differed significantly from the respective WT virus ($P<0.0001$).

To map the epitopes engaged by neutralizing hMAbs, we subjected the appropriate DENV serotype to Ab pressure and selected for neutralization escape mutant viruses in vitro. DENV1, DENV2, or DENV3 was passaged several times under varying concentrations (0.2-10 µg/mL) of the neutralizing hMAb 1F4, 2D22, or 5J7, respectively. The original WT virus was passaged in parallel in the absence of hMAb treatment. Structural genes of the mutant and WT viruses were sequenced and compared to identify the mutation(s) responsible for neutralization escape. We successfully isolated two escape mutants against DENV1 type-specific MAb 1F4, with two independent single-nucleotide mutations resulting in amino acid changes at position 274 (G→E) in the DI-DII hinge and 47 (K→E) in DI of the E protein (FIGS. 3A and 3D) that conferred loss of neutralization. K47 and G274 are located 13.2 Å apart and likely comprise part of the same 1F4 epitope. For the DENV2-specific neutralizing hMAb 2D22, we isolated one mutant with an EDIII mutation at residue 323 (R→G) that resulted in neutralization escape (FIGS. 3B and 3E). Selection with the neutralizing DENV3 specific hMAb 5J7 resulted in an escape mutant with a lysine insertion in the E DI-DII hinge region between the amino acid residues Q269 and N270 (FIGS. 3C and 3F). All the mutated residues are surface exposed on the structure of the E protein dimer and within the footprint of a complex epitope described for an hMAb (CR4354) that strongly neutralized West Nile virus (WNV) (14, 34) (FIGS. 3G and 3H and Table 3).

TABLE 1

Homologous DENV serotype neutralization titers of immune sera depleted of cross-reactive Abs from subjects following primary injection

| Infection Serotype | Sample ID | Reciprocal of 50% neutralization titer against the homologous virus (SEM)[a,b] | | |
|---|---|---|---|---|
| | | Undepleted | Control depleted | Cross-reactive Ab depleted |
| Primary DENV2 | 001 | 2600 (2040-2700) | 1650 (1100-1650) | 1412 (1060-1600) |
| | 013 | 350 (260-470) | 320 (260-380) | 420 (370-550) |

TABLE 1-continued

Homologous DENV serotype neutralization titers of immune sera depleted of cross-reactive Abs from subjects following primary injection

| Infection Serotype | Sample ID | Reciprocal of 50% neutralization titer against the homologous virus (SEM)[a,b] | | |
|---|---|---|---|---|
| | | Undepleted | Control depleted | Cross-reactive Ab depleted |
| | 019 | 1202 (1000-1550) | 1047 (930-1580) | 1000 (800-1420) |
| | 031 | 1150 (1000-1310) | 790 (650-950) | 640 (540-740) |
| Primary DENV3 | 003 | 250 (230-350) | 210 (160-260) | 300 (250-360) |
| | 011 | 320 (265-390) | 300 (260-380) | 252 (211-300) |
| | 118 | 628 (510-770) | 720 (610-860) | 618 (500-750) |

[a]Data is representative of experiments repeated at least thrice for each serum sample. The flow-based neutralization assay using U937 cells stably expressing DC-SIGN (U937 + DC-SIGN) was used to generate the reciprocal Neut$_{50}$ values. The Neut$_{50}$ values of undepleted, control depleted and cross-reactive antibody depleted sera were compared for each serum by one-way ANOVA analysis. No statistical significance was found between control depleted and cross-reactive depleted groups for any of the tested sera.
[b]Standard error of mean (SEM) for reciprocal Neut$_{50}$ values were calculated from the sigmoidal neutralization curves using GraphPad Prism4 and given in parenthesis.

TABLE 2

Homologous DENV serotype neutralization titers of primary immune sera depleted of rE-binding Abs

| Infection Serotype | Sample ID | Reciprocal of 50% Neutralization titer against the homologous virus (SEM)[a] | | |
|---|---|---|---|---|
| | | Undepleted | Control depleted | rE depleted |
| Primary DENV2 | 001[b] | 660 (510-840) | 850 (690-950) | 260 (210-310) |
| | 019[c] | 1250 (1010-1500) | 1120 (950-1350) | 500 (400-600) |
| | 031 | 1020 (790-1300) | 860 (670-1150) | 900 (690-1190) |
| Primary DENV3 | 003 | 180 (155-250) | 225 (210-310) | 215 (150-220) |
| | 105 | 180 (140-235) | 200 (160-275) | 160 (130-185) |
| | 118 | 1580 (1180-2020) | 1480 (1200-1790) | 1120 (900-1400) |

[a]Data is representative of experiments repeated at least thrice for each serum sample. Standard errors of mean (SEM) for reciprocal Neut$_{50}$ values were calculated from the sigmoidal neutralization curves using GraphPad Prism4 and are given in parenthesis.
[b]There was a statistically significant difference between the undepleted/control depleted and rE depleted groups for sample by a one-way ANOVA analysis followed by a Tukey's multiple comparison test at P < 0.01.
[c]There was a statistically significant difference between the undepleted and rE depleted groups when analyzed by a one-way ANOVA at P < 0.05.

TABLE 3

Binding and neutralization properties of strongly neutralizing hmAbs

| MAbs | Virus | Binding (2 µg/ml)[a] | | | Neut$_{50}$ titer (µg/ml)[d] | | | | Escape mutant | Escape Mutation | Mutation Location | Analogous residue in WNV Comparison to CR4354 epitope)[e] |
|---|---|---|---|---|---|---|---|---|---|---|---|---|
| | | rE | EDIII | prM[c] | DENV1 | DENV2 | DENV3 | DENV4 | | | | |
| 1F4 | Type-Specific (DENV1) | – | – | – | 0.11 | >10 | >10 | >10 | 1 | G274E | DI-DII hinge | 276 (Contact site) |
| | | | | | | | | | 2 | K47E | DI | 49 (Contact site) |

TABLE 3-continued

Binding and neutralization properties of strongly neutralizing hmAbs

| MAbs | Virus | Binding (2 μg/ml)[a] | | | Neut$_{50}$ titer (μg/ml)[d] | | | | Escape mutant | Escape Mutation | Mutation Location | Analogous residue in WNV Comparison to CR4354 epitope[e] |
|---|---|---|---|---|---|---|---|---|---|---|---|---|
| | | rE | EDIII | prM[c] | DENV1 | DENV2 | DENV3 | DENV4 | | | | |
| 2D22[b] | Type-Specific (DENV2) | − | − | − | >10 | 0.08 | >10 | >10 | 3 | R323G | DIII | 326 (Near contact site 328) |
| 5J7[b] | Type-Specific (DENV3) | + | − | − | >10 | >10 | 0.10 | >10 | 4 | Q269_N270insK | DI-DII hinge | Before 274 (near contact site 276) |

[a]Binding of Human MAbs (at 2 μg/ml) to DENV antigens were measured by ELISA.
[b]Binding and neutralization properties of 2D22 and 5J7 were taken from previous study (32).
[c]Binding to prM was determined by western blot analysis.
[d]Neut$_{50}$ values were generated using the flow-based neutralization assay with U937-DC-SIGN cells. Values in bold indicate the lowest Neut$_{50}$ concentration and the most neutralization sensitive serotype for each MAb.
[e]Comparison of the escape mutations generated against 1F4, 2D22 and 5J7 to the CR4354 epitope in WNV (14, 38)

TABLE 4

Panel of late convalescent DENV-immune sera from individuals with past primary DENV2 or DENV3 infection

| Sample ID | Location of Infection | Year of Infection | Interval between infection and sample collection | DENV Neutralization[b] (FRNT$_{50}$ reciprocal titer) DENV serotype | | | | Infecting Serotype |
|---|---|---|---|---|---|---|---|---|
| | | | | 1 | 2 | 3 | 4 | |
| 001[a] | Sri Lanka | 1996 | 9 years | <20 | 271 | <20 | 42 | Primary DENV2 |
| 013[a] | South Pacific | 1997 | 8 years | 178 | >1280 | 65 | 140 | |
| 019 | Thailand | 1997 | 8 years | 95 | >1280 | 120 | 105 | |
| 031 | South Pacific | 1997 | 8 years | 28 | >320 | 88 | 167 | |
| 003[a] | Thailand | 2001 | 4 years | 30 | 87 | 338 | <20 | Primary DENV3 |
| 011[a] | El Salvador | 1998 | 7 years | 84 | 124 | 1032 | 169 | |
| 105 | Thailand | 2002 | 8 years | <20 | <20 | 210 | <20 | |
| 118 | Nicaragua | 2009 | 1.5 years | 60 | 32 | 980 | 76 | |

[a]The FRNT$_{50}$ values for these serum samples were reported in a previous study (42).
[b]FRNT$_{50}$ values in bold signify the highest 50% neutralization reciprocal titers for each serum sample.

TABLE 5

Binding properties of DENV-immune sera with and without rE-binding Abs to the homologous virus serotype

| Infection Serotype | Sample ID | 50% Reciprocal binding titers to the homologous virus (SEM)[a] | | |
|---|---|---|---|---|
| | | Undepleted | Control depleted | Homotypic rE Depleted[d] |
| Primary DENV2 | 001[b] | 280 (260-290) | 310 (290-335) | 133 (130-140) |
| | 031[b] | 445 (415-475) | 455 (435-475) | 260 (240-275)[b] |
| Primary DENV3 | 003[b] | 216 (205-225) | 190 (180-200) | 108 (105-115)[b] |
| | 105[b] | 60 (53-66) | 63 (60-68) | 37[b] (34-42) |
| | 118[c] | 440 (400-490) | 350 (325-375) | 265[c] (250-280) |

[a]Data representative of experiments repeated at least twice for each serum sample. Standard error of mean for each reciprocal 50% reciprocal binding titer (EC$_{50}$) given in parentheses.
[b]There is a statistically significant difference between the control depleted and rE depleted groups by a one way ANOVA analysis followed by a Tukey's multiple comparison test at P < 0.001.
[c]There is a statistically significant difference between the control depleted and rE depleted group when analyzed by a one way ANOVA at P < 0.05.
[d]The rE-reactive antibodies account for about 45 ± 7% of the total homotypic virus binding antibodies.

TABLE 6

Amino acid residues of the DI-DII hinge region and DIII region of dengue virus E glycoproteins of DENV1, DENV2, DENV3, DENV4 and corresponding regions of YFV and JEV. Amino acid numbering is based on amino acid sequences shown in the sequence alignment in FIG. 11.

| Epitope | Amino acid residues |
|---|---|
| DI-DII hinge of E protein | DENV1, 2, 3, 4: AA 47-59 |
| | YFV: AA 47-59 |
| | JEV: AA 47-59 |
| | DENV1, 2, 3, 4: AA 124-133 |
| | YFV: AA 124-133 |
| | JEV: AA124-133 |
| | DENV3: AA 199-222 |
| | DENV1, 2, 4: AA 201-224 |
| | YFV: AA 198-220 |
| | JEV: AA 206-228 |
| | DENV3: AA 269-278 |
| | DENV1, 2, 4: AA 271-280 |
| | YFV: AA 265-278 |
| | JEV: AA 273-282 |
| DIII of E protein | DENV3: AA 305-308 |
| | DENV1, 2, 4: AA 307-310 |
| | YFV: AA305-308 |
| | JEV: AA 309-312 |
| | DENV3: AA 323-325 |

TABLE 6-continued

Amino acid residues of the DI-DII hinge region and DIII region of dengue virus E glycoproteins of DENV1, DENV2, DENV3, DENV4 and corresponding regions of YFV and JEV. Amino acid numbering is based on amino acid sequences shown in the sequence alignment in FIG. 11.

| Epitope | Amino acid residues |
|---|---|
| | DENV1, 2, 4: AA 325-327 |
| | YFV: AA 323-325 |
| | JEV: AA327-329 |
| | DENV3: AA 359-362 |
| | DENV1, 2, 4: AA 361-364 |
| | YFV: AA 359-362 |
| | JEV: AA 364-369 |
| | DENV3: AA 382-383 |
| | DENV1, 2, 4: AA 384-385 |
| | YFV: AA 382-383 |
| | JEV: AA 389-390 |

REFERENCES FOR EXAMPLE 1

1. Beasley, D. W. C., and A. D. T. Barrett. 2008. The Infectious Agent, p. 29-73. In S. B. P. Halstead, G; Hoffman, S. L. (ed.), Dengue, 1 ed, vol. 5. Imperial College Press, London.
2. Beltramello, M., K. L. Williams, C. P. Simmons, A. Macagno, L. Simonelli, N. T. Quyen, S. Sukupolvi-Petty, E. Navarro-Sanchez, P. R. Young, A. M. de Silva, F. A. Rey, L. Varani, S. S. Whitehead, M. S. Diamond, E. Harris, A. Lanzavecchia, and F. Sallusto. 2010. The human immune response to Dengue virus is dominated by highly cross-reactive antibodies endowed with neutralizing and enhancing activity. Cell Host Microbe 8:271-83.
3. Brien, J. D., S. K. Austin, S. Sukupolvi-Petty, K. M. O'Brien, S. Johnson, D. H. Fremont, and M. S. Diamond. 2010. Genotype-specific neutralization and protection by antibodies against dengue virus type 3. J Virol 84:10630-43.
4. Coller, B. A., D. E. Clements, A. J. Bett, S. L. Sagar, and J. H. Ter Meulen. 2011. The development of recombinant subunit envelope-based vaccines to protect against dengue virus induced disease. Vaccine 29:7267-75.
5. de Alwis, R., M. Beltramello, W. B. Messer, S. Sukupolvi-Petty, W. M. Wahala, A. Kraus, N. P. Olivarez, Q. Pham, J. Brian, W. Y. Tsai, W. K. Wang, S. Halstead, S. Kliks, M. S. Diamond, R. Baric, A. Lanzavecchia, F. Sallusto, and A. M. de Silva. 2011. In-depth analysis of the antibody response of individuals exposed to primary dengue virus infection. PLoS Negl Trop Dis 5:e1188.
6. de Alwis, R., M. Beltramello, W. B. Messer, S. Sukupolvi-Petty, W. M. Wahala, A. Kraus, N. P. Olivarez, Q. Pham, J. D. Brien, W. Y. Tsai, W. K. Wang, S. Halstead, S. Kliks, M. S. Diamond, R. Baric, A. Lanzavecchia, F. Sallusto, and A. M. de Silva. 2011. In-depth analysis of the antibody response of individuals exposed to primary dengue virus infection. PLoS Negl Trop Dis 5:e1188.
7. Dejnirattisai, W., A. Jumnainsong, N. Onsirisakul, P. Fitton, S. Vasanawathana, W. Limpitikul, C. Puttikhunt, C. Edwards, T. Duangchinda, S. Supasa, K. Chawansuntati, P. Malasit, J. Mongkolsapaya, and G. Screaton. 2010. Cross-reacting antibodies enhance dengue virus infection in humans. Science 328:745-8.
8. Dias, J. M., A. I. Kuehne, D. M. Abelson, S. Bale, A. C. Wong, P. Halfmann, M. A. Muhammad, M. L. Fusco, S. E. Zak, E. Kang, Y. Kawaoka, K. Chandran, J. M. Dye, and E. O. Saphire. 2011. A shared structural solution for neutralizing ebolaviruses. Nat Struct Mol Biol 18:1424-7.
9. Goncalvez, A. P., C. H. Chien, K. Tubthong, I. Gorshkova, C. Roll, O. Donau, P. Schuck, S. Yoksan, S. D. Wang, R. H. Purcell, and C. J. Lai. 2008. Humanized monoclonal antibodies derived from chimpanzee Fabs protect against Japanese encephalitis virus in vitro and in vivo. J Virol 82:7009-21.
10. Gromowski, G. D., and A. D. Barrett. 2007. Characterization of an antigenic site that contains a dominant, type-specific neutralization determinant on the envelope protein domain III (ED3) of dengue 2 virus. Virology 366:349-60.
11. Gromowski, G. D., J. T. Roehrig, M. S. Diamond, J. C. Lee, T. J. Pitcher, and A. D. Barrett. 2010. Mutations of an antibody binding energy hot spot on domain III of the dengue 2 envelope glycoprotein exploited for neutralization escape. Virology 407:237-46.
12. Halstead, S. B. 2003. Neutralization and antibody-dependent enhancement of dengue viruses. Adv Virus Res 60:421-67.
13. Imrie, A., J. Meeks, A. Gurary, M. Sukhbaatar, T. T. Truong, C. B. Cropp, and P. Effler. 2007. Antibody to dengue 1 detected more than 60 years after infection. Viral Immunol 20:672-5.
14. Kaufmann, B., M. R. Vogt, J. Goudsmit, H. A. Holdaway, A. A. Aksyuk, P. R. Chipman, R. J. Kuhn, M. S. Diamond, and M. G. Rossmann. 2010. Neutralization of West Nile virus by cross-linking of its surface proteins with Fab fragments of the human monoclonal antibody CR4354. Proc Natl Acad Sci USA 107:18950-5.
15. Kraus, A. A., W. Messer, L. B. Haymore, and A. M. de Silva. 2007. Comparison of plaque- and flow cytometry-based methods for measuring dengue virus neutralization. J Clin Microbiol 45:3777-80.
16. Kuhn, R. J., W. Zhang, M. G. Rossmann, S. V. Pletnev, J. Corver, E. Lenches, C. T. Jones, S. Mukhopadhyay, P. R. Chipman, E. G. Strauss, T. S. Baker, and J. H. Strauss. 2002. Structure of dengue virus: implications for flavivirus organization, maturation, and fusion. Cell 108:717-25.
17. Li, L., S. M. Lok, I. M. Yu, Y. Zhang, R. J. Kuhn, J. Chen, and M. G. Rossmann 2008. The flavivirus precursor membrane-envelope protein complex: structure and maturation. Science 319:1830-4.
18. Lok, S. M., V. Kostyuchenko, G. E. Nybakken, H. A. Holdaway, A. J. Battisti, S. Sukupolvi-Petty, D. Sedlak, D. H. Fremont, P. R. Chipman, J. T. Roehrig, M. S. Diamond, R. J. Kuhn, and M. G. Rossmann. 2008. Binding of a neutralizing antibody to dengue virus alters the arrangement of surface glycoproteins. Nat Struct Mol Biol 15:312-7.
19. Mackenzie, J. S., D. J. Gubler, and L. R. Petersen. 2004. Emerging flaviviruses: the spread and resurgence of Japanese encephalitis, West Nile and dengue viruses. Nat Med 10:S98-109.
20. Mantel, N., Y. Girerd, C. Geny, I. Bernard, J. Pontvianne, J. Lang, and V. Barban. 2011. Genetic stability of a dengue vaccine based on chimeric yellow fever/dengue viruses. Vaccine 29:6629-35.
21. McMinn, P. C., E. Lee, S. Hartley, J. T. Roehrig, L. Dalgarno, and R. C. Weir. 1995. Murray valley encephalitis virus envelope protein antigenic variants with altered hemagglutination properties and reduced neuroinvasiveness in mice. Virology 211:10-20.
22. Modis, Y., S. Ogata, D. Clements, and S. C. Harrison. 2003. A ligand-binding pocket in the dengue virus envelope glycoprotein. Proc Natl Acad Sci USA 100:6986-91.

23. Modis, Y., S. Ogata, D. Clements, and S. C. Harrison. 2005. Variable surface epitopes in the crystal structure of dengue virus type 3 envelope glycoprotein. J Virol 79:1223-31.
24. Nybakken, G. E., T. Oliphant, S. Johnson, S. Burke, M. S. Diamond, and D. H. Fremont. 2005. Structural basis of West Nile virus neutralization by a therapeutic antibody. Nature 437:764-9.
25. Oliphant, T., G. E. Nybakken, S. K. Austin, Q. Xu, J. Bramson, M. Loeb, M. Throsby, D. H. Fremont, T. C. Pierson, and M. S. Diamond. 2007. Induction of epitope-specific neutralizing antibodies against West Nile virus. J Virol 81:11828-39.
26. Oliphant, T., G. E. Nybakken, M. Engle, Q. Xu, C. A. Nelson, S. Sukupolvi-Petty, A. Mani, B. E. Lachmi, U. Olshevsky, D. H. Fremont, T. C. Pierson, and M. S. Diamond. 2006. Antibody recognition and neutralization determinants on domains I and II of West Nile Virus envelope protein. J Virol 80:12149-59.
27. Osorio, J. E., C. Y. Huang, R. M. Kinney, and D. T. Stinchcomb. 2011. Development of DENVax: a chimeric dengue-2 PDK-53-based tetravalent vaccine for protection against dengue fever. Vaccine 29:7251-60.
28. Rey, F. A., F. X. Heinz, C. Mandl, C. Kunz, and S. C. Harrison. 1995. The envelope glycoprotein from tick-borne encephalitis virus at 2 A resolution. Nature 375:291-8.
29. Roehrig, J. T. 2003. Antigenic structure of flavivirus proteins. Adv Virus Res 59:141-75.
30. Sanchez, M. D., T. C. Pierson, M. M. Degrace, L. M. Maffei, S. L. Hanna, F. Del Piero, and R. W. Doms. 2007. The neutralizing antibody response against West Nile virus in naturally infected horses. Virology 359:336-48.
31. Shrestha, B., J. D. Brien, S. Sukupolvi-Petty, S. K. Austin, M. A. Edeling, T. Kim, K. M. O'Brien, C. A. Nelson, S. Johnson, D. H. Fremont, and M. S. Diamond. 2010. The development of therapeutic antibodies that neutralize homologous and heterologous genotypes of dengue virus type 1. PLoS Pathog 6:e1000823.
32. Smith, S. A., Y. Zhou, N. P. Olivarez, A. H. Broadwater, A. M. de Silva, and J. E. Crowe, Jr. 2011. Persistence of circulating B memory cell clones with potential for dengue virus disease enhancement for decades following infection. J Virol.
33. Smith, S. A., Y. Zhou, N. P. Olivarez, A. H. Broadwater, A. M. de Silva, and J. E. Crowe, Jr. 2012. Persistence of circulating memory B cell clones with potential for dengue virus disease enhancement for decades following infection. J Virol 86:2665-75.
34. Spurrier, B., J. M. Sampson, M. Totrov, H. Li, T. O'Neal, C. Williams, J. Robinson, M. K. Gorny, S. Zolla-Pazner, and X. P. Kong. 2011. Structural analysis of human and macaque MAbs 2909 and 2.5B: implications for the configuration of the quaternary neutralizing epitope of HIV-1 gp120. Structure 19:691-9.
35. Sukupolvi-Petty, S., S. K. Austin, M. Engle, J. D. Brien, K. A. Dowd, K. L. Williams, S. Johnson, R. Rico-Hesse, E. Harris, T. C. Pierson, D. H. Fremont, and M. S. Diamond. 2010. Structure and function analysis of therapeutic monoclonal antibodies against dengue virus type 2. J Virol 84:9227-39.
36. Sukupolvi-Petty, S., S. K. Austin, W. E. Purtha, T. Oliphant, G. E. Nybakken, J. J. Schlesinger, J. T. Roehrig, G. D. Gromowski, A. D. Barrett, D. H. Fremont, and M. S. Diamond. 2007. Type- and subcomplex-specific neutralizing antibodies against domain III of dengue virus type 2 envelope protein recognize adjacent epitopes. J Virol 81:12816-26.
37. Valdes, I., L. Gil, Y. Romero, J. Castro, P. Puente, L. Lazo, E. Marcos, M. G. Guzman, G. Guillen, and L. Hermida. 2011. The chimeric protein domain III-capsid of dengue virus serotype 2 (DEN-2) successfully boosts neutralizing antibodies generated in monkeys upon infection with DEN-2. Clin Vaccine Immunol 18:455-9.
38. Vogt, M. R., B. Moesker, J. Goudsmit, M. Jongeneelen, S. K. Austin, T. Oliphant, S. Nelson, T. C. Pierson, J. Wilschut, M. Throsby, and M. S. Diamond. 2009. Human monoclonal antibodies against West Nile virus induced by natural infection neutralize at a postattachment step. J Virol 83:6494-507.
39. Wahala, W. M., E. F. Donaldson, R. de Alwis, M. A. Accavitti-Loper, R. S. Baric, and A. M. de Silva. 2010. Natural strain variation and antibody neutralization of dengue serotype 3 viruses. PLoS Pathog 6:e1000821.
40. Wahala, W. M., C. Huang, S. Butrapet, L. White, and A. M. de Silva. 2012. Recombinant dengue type 2 viruses with altered E protein domain III epitopes are efficiently neutralized by human immune sera. J Virol.
41. Wahala, W. M., C. Huang, S. Butrapet, L. J. White, and A. M. de Silva. 2012. Recombinant dengue type 2 viruses with altered e protein domain III epitopes are efficiently neutralized by human immune sera. J Virol 86:4019-23.
42. Wahala, W. M., A. A. Kraus, L. B. Haymore, M. A. Accavitti-Loper, and A. M. de Silva. 2009. Dengue virus neutralization by human immune sera: role of envelope protein domain III-reactive antibody. Virology 392:103-13.
43. Yu, X., P. A. McGraw, F. S. House, and J. E. Crowe, Jr. 2008. An optimized electrofusion-based protocol for generating virus-specific human monoclonal antibodies. J Immunol Methods 336:142-51.
44. Zhang, W., P. R. Chipman, J. Corver, P. R. Johnson, Y. Zhang, S. Mukhopadhyay, T. S. Baker, J. H. Strauss, M. G. Rossmann, and R. J. Kuhn. 2003. Visualization of membrane protein domains by cryo-electron microscopy of dengue virus. Nat Struct Biol 10:907-12.

Example 2: Escape Mutant Studies

Infection with one DENV serotype elicits protective antibodies against that serotype, but also cross-reactive with other DENV serotypes. These cross-reactive antibodies enhance the risk of severe dengue on second infection in that individual with another DENV serotype. The envelope protein (E) is the major antigenic determinant of dengue virus, and the epitopes that exclusively provide neutralization, but are not cross reactive, have not been previously identified. This represents a major challenge in dengue virus vaccine design.

Figure 8:
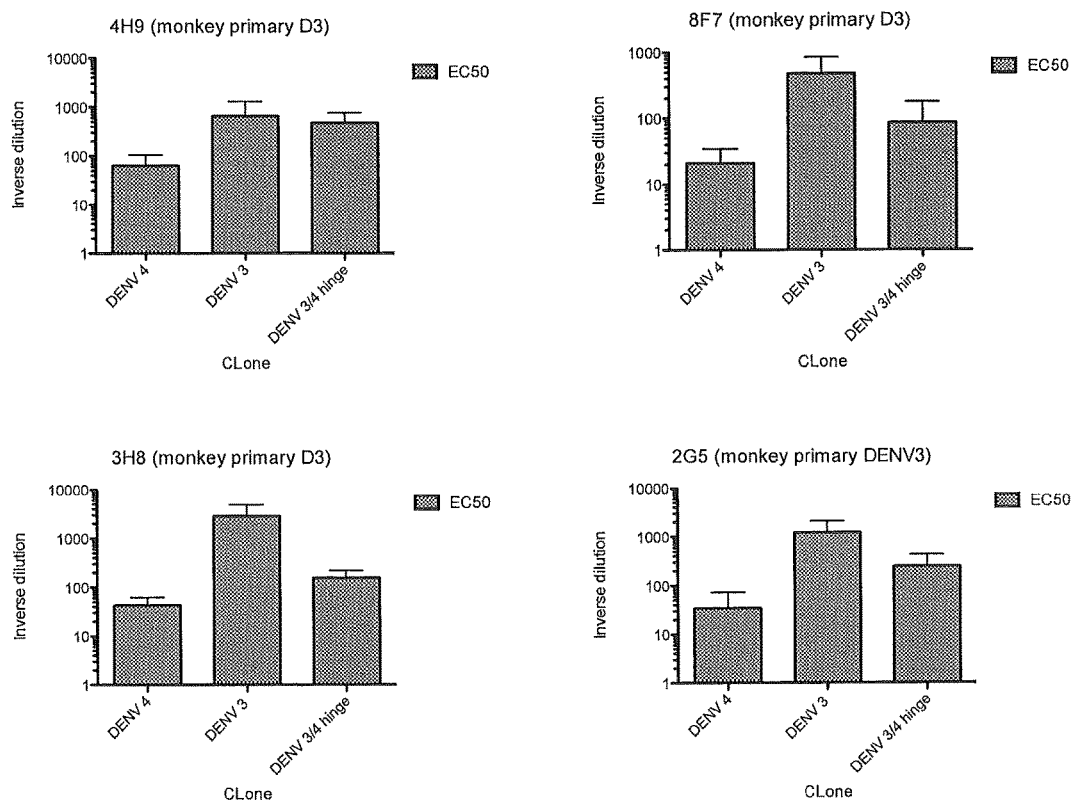
FIG. 8. Loss of function: 50% neutralization titers for primary monkey anti-DENV3 sera against DENV 4, DENV 3 and DENV 3 with DENV 4 hinge (3/4 Hinge). X axis shows virus and Y axis shows inverse serum dilution on a log scale. The higher the inverse dilution value the more potent the sera is against a particular virus. Three of the sera, 8F7, 3H3 and 2G5 clearly lose potency against DENV 3/4 hinge virus.
Figure 9:
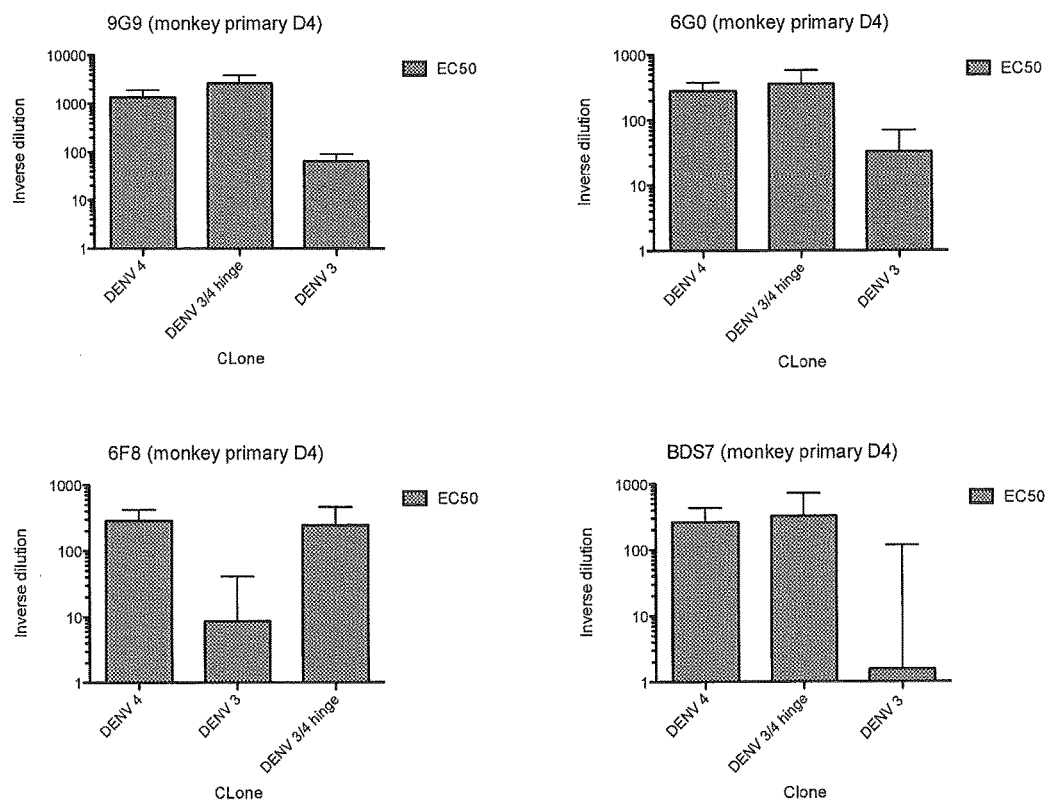
FIG. 9. Gain of function: 50% neutralization titers for primary monkey anti-DENV4 sera against DENV 4, DENV 3 and DENV 3 with DENV 4 hinge (3/4 Hinge). X axis shows virus and Y axis shows inverse serum dilution on a log scale. The higher the inverse dilution value the more potent the serum is against a particular virus. All four of the sera clearly gain potency against DENV 3/4 hinge virus.
Figure 10:
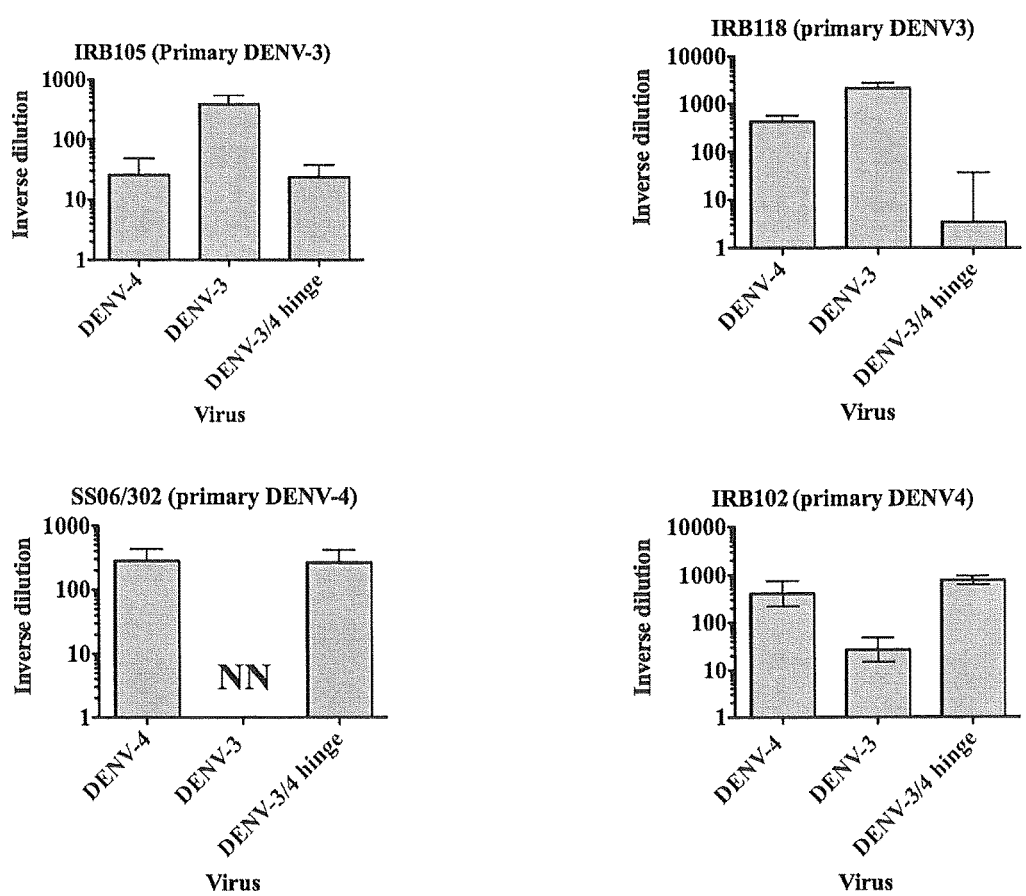
FIG. 10. Gain and loss of function: 50% neutralization titers for primary human anti-DENV 3 sera and anti-DENV 4 against DENV 4, DENV 3 and DENV 3 with DENV 4 hinge (3/4 Hinge). X axis shows virus and Y axis shows inverse serum dilution on a log scale. The higher the inverse dilution value the more potent the sera is against a particular virus. The two primary DENV-3 sera clearly lost potency against DENV 3/4 hinge virus and the two primary DENV-4 sera clearly gain potency against DENV 3/4 hinge virus.

A set of discontinuous strands have been identified that make up the EDI-II hinge region of the DENV E glycoprotein, as the key epitope region targeted by neutralizing human antibodies. This epitope is conserved in the E protein of all four DENV serotypes. This region was identified through a multi-step process. Initially, DENV-3 was serial passaged in the presence of the DENV-3 type specific potentially neutralizing human mAb, 5J7, resulting in the generation of several viral escape mutants. These mutants were sequenced and three key amino acid mutations conferring escape were identified. To generate a model of the putative 5J7 epitope, the escape mutant residues were located on the DENV-3 E crystal structure. Using a strategy initially developed to identify norovirus epitopes, (1-3) modeling software was used to identify all residues within 12 Å of all three mutation sites. The DENV-4 E sequence was then aligned with the DENV-3 structure and each DENV-4 residue that varied from DENV-3 residues within that 12 Å region was identified, 25 residues in total (Table and FIG. 3, attached PDF). To assess the role of this antigenic region identified by the 5J7 escape mutants; a "chimeric" nucleotide E gene sequence that introduced the variable DENV-4 residues into the DENV-3 E backbone was synthesized by Biobasic. The DENV 3/4 12 Å (25 residues changed) E genes was then recombined into the existing DENV-3 3001 clone using reverse genetics, see methods (4). The new clone was designated 3001A12. 3001A12 was screened in a 50% Focus Reduction Neutralization Assay (FRNT$_{50}$), using human sera to dengue virus serotypes 3 and 4 (4). The assay results clearly demonstrated that 3001A12 was completely neutralized by human and monkey immune sera to DENV 4, while the capacity of DENV-3 immune sera to neutralize 3001A12 were significantly diminished (FIGS. 8-10). This is the first "proof-of-concept" for identification and transfer of the epitope region that defines a DENV serotype. Studies are underway to assess the immunogenic potential of these chimeric viruses in mice to stimulate the generation of neutralizing antibodies, and in DENV-3 and -4 immune nonhuman primates to assess whether or not the gain and loss of neutralization in vitro is preserved in vivo.

REFERENCES FOR EXAMPLE 2

1. Debbink et al. "Genetic mapping of a highly variable norovirus GII.4 blockade epitope: Potential role in escape from human herd immunity" *J Virol.* 86(2):1214-26 (2012)
2. Lindesmith et al. "Monoclonal antibody-based antigenic mapping of norovirus GII.4-2002" *J Virol.* 86(2):873-83 (2012)
3. Lindesmith et al. "Immunogenetic mechanisms driving norovirus GII.4 antigenic variation. *PLoS Pathog.* 8(5): e1002705 (2012)
4. Messer et al. "Development and characterization of a reverse genetic system for studying dengue virus serotype 3 strain variation and neutralization" *PLoS Negl Trop Dis.* 6(2):e1486 (2012)

The foregoing is illustrative of the present invention, and is not to be construed as limiting thereof. The invention is defined by the following claims, with equivalents of the claims to be included therein.

All publications, patent applications, patents and other references cited herein are incorporated by reference in their entireties for the teachings relevant to the sentence and/or paragraph in which the reference is presented.

TABLE 7

Mutations in 3001A12. The letter to the left of the number indicates original amino acid, the number indicates amino acid position, and the letter to the right of the number indicates the amino acid replacing the original amino acid. Positions are based on the DENV3 E glycoprotein amino acid sequence.

| |
|---|
| T51K |
| Q52E |
| L53V |
| T55L |
| K58T |
| L59Y |
| P124K |
| E126T |
| K128N |
| V129L |
| T198K |
| N201K |
| A203T |
| M205L |
| R208K |
| F212L |
| S220A |
| I268V |
| Q269D |
| N270S |
| S271G |
| G272D |
| T274N |
| S275H |
| I276M |

What is claimed is:

1. A chimeric dengue virus E glycoprotein selected from the group consisting of:
   a) a first dengue virus E glycoprotein backbone from dengue virus serotype 1 (SEQ ID NO:18) comprising a V50A substitution, a T51K substitution, an N52Q substitution, a V55T substitution, an L59Y substitution, a K124N substitution, an L125M substitution, an I129V substitution, a Y132P substitution, a K203N substitution, an S205A substitution, a K210R substitution, a T221L substitution, an S222P substitution, a T272M substitution, a G274S substitution, a T275G substitution, a T276N substitution, a T277L substitution, an I278L substitution, and an A280T substitution;
   b) a second dengue virus E glycoprotein backbone from dengue virus serotype 1 (SEQ ID NO:18) comprising a V50A substitution, an N52Q substitution, a P53L substitution, a V55T substitution, a K124P substitution, an L125I substitution, an I129V substitution, an E202K substitution, a K203N substitution, an S205A substitution, an L207M substitution, a K210R substitution, a L2141F substitution, a T272N substitution, a T275G substitution, and a T277S substitution; and
   c) a third dengue virus E glycoprotein backbone from dengue virus serotype 1 (SEQ ID NO:18) comprising an E49T substitution, a V50A substitution, a T51K substitution, an N52E substitution, a P53V substitution, a V55L substitution, a K58T substitution, an L59Y substitution, an L125I substitution, an EL26T substitution, a K128N substitution, an I129L substitution, a Y132I substitution, an E202K substitution, an S205T substitution, an S222A substitution, a Q271D substitution, a T272S substitution, an S273G substitution, a G274D substitution, a T275G substitution, a T276N substitution, a T277H substitution, and an I278M substitution.

2. A chimeric dengue virus E glycoprotein selected from the group consisting of:
   a) a first dengue virus E glycoprotein backbone from dengue virus serotype 2 (SEQ ID NO:20) comprising an A50V substitution, a K51T substitution, a Q52N substitution, a T55V substitution, a Y59L substitution, an N124K substitution, an M125L substitution, a V129I substitution, a P132Y substitution, an N203K substitution, an A205S substitution, an R210K substitution, an L221T substitution, a P222S, an M272T substitution, an S274G substitution, a G275T substitution, an N276T substitution, an L277T substitution, an L278I substitution, and a T280A substitution;
   b) a second dengue virus E glycoprotein backbone from dengue virus serotype 2 (SEQ ID NO:20) comprising a K51T substitution, a P53L substitution, a Y59L substitution, an N124P substitution, an M125I substitution, a P132Y substitution, an E202K substitution, an L207M substitution, an L214F substitution, an L221T substitution, a P222S substitution, an M272N substitution, an S274G substitution, an N276T substitution, an L277S substitution, an L278I substitution, and a I280A substitution; and c) a third dengue virus E glycoprotein backbone from dengue virus serotype 2 (SEQ ID NO:20) comprising an E49T substitution, a Q52E substitution, a P53V substitution, a T55L substitution, a K58T substitution, an N124K substitution, an M125I substitution, an E126T substitution, a K128N substitution, a V129L substitution, a P132I substitution, an E202K substitution, an N203K substitution, an A205T substitution, an R210K substitution, an L221T substitution, a P222A substitution, a Q271D substitution, an M272S substitution, an S273G substitution, an S274D substitution, an L277H substitution, an L278M substitution, and a T280A substitution.

3. A chimeric dengue virus E glycoprotein selected from the group consisting of:
a) a first dengue virus E glycoprotein backbone from dengue virus serotype 3 (SEQ ID NO:17) comprising an A50V substitution, a Q52N substitution, an L53P substitution, a T55V substitution, a P124K substitution, an I125L substitution, a V129I substitution, a K200E substitution, an N201K substitution, an A203S substitution, an M205L substitution, an R208K substitution, an F212L substitution, an N270T substitution, a G273T substitution, and an S275T substitution;
b) a second dengue virus E glycoprotein backbone from dengue virus serotype 3 (SEQ ID NO:17) comprising a T51K substitution, an L53P substitution, an L59Y substitution, a P124N substitution, an 125M substitution, a Y132P substitution, a K200E substitution, an M205L substitution, an F212L substitution, a T219L substitution, an S220P substitution, an N270M substitution, a G272S substitution, a T274N substitution, an S275L substitution, an I276L substitution, and an A278T substitution;
c) a third dengue virus E glycoprotein backbone from dengue virus serotype 3 (SEQ ID NO:17) comprising an E49T substitution, a T51K substitution, a Q52E substitution, an L53V substitution, a T55L substitution, a K58T substitution, an L59Y substitution, a P124K substitution, an E126T substitution, a K128N substitution, a V129L substitution, a Y132I substitution, an N201K substitution, an A203T substitution, an M205L substitution, an R208K substitution, an F212L substitution, an S220A substitution, a Q269D substitution, an N270S substitution, an S271G substitution, a G272D substitution, a T274N substitution, an S275H substitution, and an I276M substitution; and
d) a fourth dengue virus E glycoprotein backbone from dengue virus serotype 3 (SEQ ID NO:17) comprising a T51K substitution, a Q52E substitution, an L53V substitution, a T55L substitution, a K58T substitution, an L59Y substitution, a P124K substitution, an E126T substitution, a K128N substitution, a V129I, substitution, a T198K substitution, N201K substitution, an A203T substitution, an M205L substitution, an R208K substitution, an F212L substitution, an S220A substitution, an I268V substitution, a Q269D substitution, an N270S substitution, an S271G substitution, a G272D substitution, a T274N substitution, an S275H substitution, and an I276M substitution.

4. A chimeric dengue virus E glycoprotein selected from the group consisting of:
a) a first dengue virus E glycoprotein backbone from dengue virus serotype 4 (SEQ ID NO:19) comprising a T49E substitution, an A50V substitution, a K51T substitution, an E52N substitution, a V53P substitution, an L55V substitution, a T58K substitution, a Y59L substitution, an I125L substitution, a T126E substitution, an N128K substitution, an L129I substitution, an I132Y substitution, a K202E substitution, a T205S substitution, an A222S substitution, a D271Q substitution, an S272T substitution, a G273S substitution, a D274G substitution, a G275T substitution, an N276T substitution, an H277T substitution, and an M278I substitution;
b) a second dengue virus E glycoprotein backbone from dengue virus serotype 4 (SEQ ID NO: 19) comprising a T49E substitution, an E52Q substitution, a V53P substitution, an L55T substitution, a T58K substitution, a K124N substitution, an I125M substitution, a T126E substitution, an N28K substitution, an L129V substitution, an I132P substitution, a K202E substitution, a K203N substitution, a T205A substitution, a K210R substitution, a T221L substitution, an A222P substitution, a D271Q substitution, an S272M substitution, a G273S substitution, a D274S substitution, an H277L substitution, an M278L substitution, and an A280T substitution; and
c) a third dengue virus E glycoprotein backbone from dengue virus serotype 4 (SEQ ID NO:19) comprising a T49E substitution, a K51T substitution, an E52Q substitution, a V53L substitution, an L55T substitution, a T58K substitution, a Y59L substitution, a K124P substitution, a T126E substitution, an N128K substitution, an L129V substitution, an I132Y substitution, a K203N substitution, a T205A substitution, an I207M substitution, a K210R substitution, an L214F substitution, an A222S substitution, a D271Q substitution, an S272N substitution, a G273S substitution, a D274G substitution, an N276T substitution, an H277S substitution, and an M278I substitution.

5. The first dengue virus E glycoprotein of claim 1, further comprising an L308V substitution, an E309V substitution, a K325Q substitution, an E362D substitution, a K363S substitution, an E384P substitution, and a K385G substitution.

6. The second dengue virus E glycoprotein of claim 1, further comprising a K307V substitution, an E309K substitution, a K325E substitution, an E327K substitution, a K363E substitution, an E384D substitution, and a K385N substitution.

7. The third dengue virus E glycoprotein of claim 1, further comprising a K307S substitution, an L308I substitution, an E309D substitution, a K361T substitution, an E362N substitution, a K363S substitution, a P364V substitution, an E384N substitution, and a K385S substitution.

8. The first dengue virus E glycoprotein of claim 2, further comprising a V308L substitution, a V309E substitution, a Q325K substitution, a D362E substitution, an S363K substitution, a P384E substitution, and a G385K substitution.

9. The second dengue virus E glycoprotein of claim 2, further comprising a K307V substitution, a V308L substitution, a V309K substitution, a Q325E substitution, an E327K substitution, a D362E substitution, an S363E substitution, a P384D substitution, and a G385N substitution.

10. The third dengue virus E glycoprotein of claim 2, further comprising a K307S substitution, a V308I substitution, a V309D substitution, a Q325K substitution, a K361T substitution, a D362N substitution, a P364V substitution, a P384N substitution, and a G385S substitution.

11. The first dengue virus E glycoprotein of claim 3, further comprising a V305K substitution, a K307E substitution, an E323K substitution, a K325E substitution, an E361K substitution, a D382E substitution, and an N383K substitution.

12. The second dengue virus E glycoprotein of claim 3, further comprising a V305K substitution, an L306V substitution, a K307V substitution, an E323Q substitution, a K325E substitution, an E360D substitution, an E361S substitution, a D382P substitution, and an N383G substitution.

13. The third dengue virus E glycoprotein of claim 3, further comprising a V305S substitution, an L306I substitution, a K307D substitution, an E323K substitution, a K325E substitution, a K359T substitution, an E360N substitution, an E361S substitution, a P362V substitution, a D382N substitution, and an N383S substitution.

14. The first dengue virus E glycoprotein of claim 4, further comprising an S307K substitution, an I308L substitution, a D309E substitution, a T361K substitution, an N362E substitution, an S363K substitution, a V364P substitution, an N384E substitution, and an S385K substitution.

15. The second dengue virus E glycoprotein of claim 4, further comprising an S307K substitution, an I308V substitution, a D309V substitution, a K325Q substitution, a T361K substitution, an N362D substitution, a V364P substitution, an N384P substitution, and an S385G substitution.

16. The third dengue virus E glycoprotein of claim 4, further comprising an S307V substitution, an I308L substitution, a D309K substitution, a K325E substitution, an E327K substitution, a T361K substitution, an N362E substitution, an S363E substitution, a V364P substitution, an N384D substitution, and an S385N substitution.

17. A composition comprising the chimeric dengue virus E glycoprotein of claim 1, in a pharmaceutically acceptable carrier.

18. A composition comprising the chimeric dengue virus E glycoprotein of claim 2, in a pharmaceutically acceptable carrier.

19. A composition comprising the chimeric dengue virus E glycoprotein of claim 3, in a pharmaceutically acceptable carrier.

20. A composition comprising the chimeric dengue virus E glycoprotein of claim 4, in a pharmaceutically acceptable carrier.

21. A method of producing an immune response to a dengue virus in a subject, the method comprising administering to the subject an effective amount of the chimeric dengue virus E glycoprotein of claim 1.

22. A method of producing an immune response to a dengue virus in a subject, the method comprising administering to the subject an effective amount of the chimeric dengue virus E glycoprotein of claim 2.

23. A method of producing an immune response to a dengue virus in a subject, the method comprising administering to the subject an effective amount of the chimeric dengue virus E glycoprotein of claim 3.

24. A method of producing an immune response to a dengue virus in a subject, the method comprising administering to the subject an effective amount of the chimeric dengue virus E glycoprotein of claim 4.

* * * * *

UNITED STATES PATENT AND TRADEMARK OFFICE
CERTIFICATE OF CORRECTION

PATENT NO. : 9,821,050 B2  
APPLICATION NO. : 14/390312  
DATED : November 21, 2017  
INVENTOR(S) : De Silva et al.

It is certified that error appears in the above-identified patent and that said Letters Patent is hereby corrected as shown below:

On the Title Page

Page 2, Column 2, Line 22, Item (56) References Cited, Other Publications, Guirakhoo et al. cite:
Please correct "7290-7341" to read -- 7290-7304 --

In the Specification

Column 13, Line 60: Please correct "516803" to read -- S16803 --

In the Claims

Column 56, Claim 1, Line 45: Please correct "EL26T" to read -- E126T --

Column 57, Claim 2, Line 7: Please correct "I280A" to read -- T280A --

Column 57, Claim 3, Line 37: Please correct "125M" to read -- I125M --

Column 57, Claim 3, Line 62: Please correct "V129I" to read -- V129L --

Column 58, Claim 4, Line 8: Please correct "VS3P" to read -- V53P --

Column 58, Claim 4, Line 24: Please correct "N28K" to read -- N128K --

Column 58, Claim 4, Line 39: Please correct "I207M" to read -- L207M --

Signed and Sealed this  
Tenth Day of July, 2018

Andrei Iancu  
*Director of the United States Patent and Trademark Office*

SEQUENCE LISTING

<160> NUMBER OF SEQ ID NOS: 22

<210> SEQ ID NO 1
<211> LENGTH: 12
<212> TYPE: PRT
<213> ORGANISM: Dengue virus

<400> SEQUENCE: 1

Glu Leu Leu Lys Thr Glu Val Thr Asn Pro Ala Val
1               5                   10

<210> SEQ ID NO 2
<211> LENGTH: 12
<212> TYPE: PRT
<213> ORGANISM: Dengue virus

<400> SEQUENCE: 2

Glu Leu Ile Lys Thr Glu Ala Lys Gln Pro Ala Thr
1               5                   10

<210> SEQ ID NO 3
<211> LENGTH: 12
<212> TYPE: PRT
<213> ORGANISM: Dengue virus

<400> SEQUENCE: 3

Glu Leu Gln Lys Thr Glu Ala Thr Gln Leu Ala Thr
1               5                   10

<210> SEQ ID NO 4
<211> LENGTH: 12
<212> TYPE: PRT
<213> ORGANISM: West Nile virus

<400> SEQUENCE: 4

Lys Met Met Asn Met Glu Ala Ala Asn Leu Ala Glu
1               5                   10

<210> SEQ ID NO 5
<211> LENGTH: 18
<212> TYPE: PRT
<213> ORGANISM: Dengue virus

<400> SEQUENCE: 5

Thr Glu Ile Gln Thr Ser Gly Thr Thr Thr Ile Phe Ala Gly His Leu
1               5                   10                  15

Lys Cys

<210> SEQ ID NO 6
<211> LENGTH: 18
<212> TYPE: PRT
<213> ORGANISM: Dengue virus

<400> SEQUENCE: 6

Thr Glu Ile Gln Met Ser Ser Gly Asn Leu Leu Phe Thr Gly His Leu
1               5                   10                  15

Lys Cys

<210> SEQ ID NO 7
<211> LENGTH: 18
<212> TYPE: PRT
<213> ORGANISM: Dengue virus

<400> SEQUENCE: 7

Thr Glu Ile Gln Asn Ser Gly Gly Thr Ser Ile Phe Ala Gly His Leu
1               5                   10                  15

Lys Cys

<210> SEQ ID NO 8
<211> LENGTH: 19
<212> TYPE: PRT
<213> ORGANISM: West Nile virus

<400> SEQUENCE: 8

Ile Pro Val Glu Phe Ser Ser Asn Thr Val Lys Leu Thr Ser Gly His
1               5                   10                  15

Leu Lys Cys

<210> SEQ ID NO 9
<211> LENGTH: 11
<212> TYPE: PRT

```
<213> ORGANISM: Dengue virus

<400> SEQUENCE: 9

His Gly Thr Val Leu Val Gln Val Lys Tyr Glu
1               5                   10

<210> SEQ ID NO 10
<211> LENGTH: 11
<212> TYPE: PRT
<213> ORGANISM: Dengue virus

<400> SEQUENCE: 10

His Gly Thr Ile Val Ile Arg Val Gln Tyr Glu
1               5                   10

<210> SEQ ID NO 11
<211> LENGTH: 11
<212> TYPE: PRT
<213> ORGANISM: Dengue virus

<400> SEQUENCE: 11

His Gly Thr Ile Leu Ile Lys Val Glu Tyr Lys
1               5                   10

<210> SEQ ID NO 12
<211> LENGTH: 11
<212> TYPE: PRT
<213> ORGANISM: West Nile virus

<400> SEQUENCE: 12

His Gly Thr Val Val Leu Glu Leu Gln Tyr Thr
1               5                   10

<210> SEQ ID NO 13
<211> LENGTH: 8
<212> TYPE: PRT
<213> ORGANISM: Dengue virus

<400> SEQUENCE: 13

Pro Ile Val Thr Asp Lys Glu Lys
1               5

<210> SEQ ID NO 14
<211> LENGTH: 8
<212> TYPE: PRT
<213> ORGANISM: Dengue virus

<400> SEQUENCE: 14

Pro Ile Val Thr Glu Lys Asp Ser
1               5

<210> SEQ ID NO 15
<211> LENGTH: 8
<212> TYPE: PRT
<213> ORGANISM: Dengue virus

<400> SEQUENCE: 15

Pro Val Val Thr Lys Lys Glu Glu
1               5

<210> SEQ ID NO 16
<211> LENGTH: 11
<212> TYPE: PRT
<213> ORGANISM: West Nile virus
```

<400> SEQUENCE: 16

Pro Phe Val Ser Val Ala Thr Ala Asn Ala Lys
1               5                   10

<210> SEQ ID NO 17
<211> LENGTH: 410
<212> TYPE: PRT
<213> ORGANISM: Dengue virus

<400> SEQUENCE: 17

Met Arg Cys Val Gly Ile Gly Asn Arg Asp Phe Val Glu Gly Leu Ser
1               5                   10                  15

Gly Ala Thr Trp Val Asp Val Leu Glu His Gly Gly Cys Val Thr
                20                  25                  30

Thr Met Ala Lys Asn Lys Pro Thr Leu Asp Ile Glu Leu Gln Lys Thr
            35                  40                  45

Glu Ala Thr Gln Leu Ala Thr Leu Arg Lys Leu Cys Ile Glu Gly Lys
        50                  55                  60

Ile Thr Asn Ile Thr Thr Asp Ser Arg Cys Pro Thr Gln Gly Glu Ala
65                  70                  75                  80

Val Leu Pro Glu Glu Gln Asp Gln Asn Tyr Val Cys Lys His Thr Tyr
                85                  90                  95

Val Asp Arg Gly Trp Gly Asn Gly Cys Gly Leu Phe Gly Lys Gly Ser
            100                 105                 110

Leu Val Thr Cys Ala Lys Phe Gln Cys Leu Glu Pro Ile Glu Gly Lys
        115                 120                 125

Val Val Gln Tyr Glu Asn Leu Lys Tyr Thr Val Ile Ile Thr Val His
    130                 135                 140

Thr Gly Asp Gln His Gln Val Gly Asn Glu Thr Gln Gly Val Thr Ala
145                 150                 155                 160

Glu Ile Thr Pro Gln Ala Ser Thr Thr Glu Ala Ile Leu Pro Glu Tyr
                165                 170                 175

Gly Thr Leu Gly Leu Glu Cys Ser Pro Arg Thr Gly Leu Asp Phe Asn
            180                 185                 190

Glu Met Ile Leu Leu Thr Met Lys Asn Lys Ala Trp Met Val His Arg
        195                 200                 205

Gln Trp Phe Phe Asp Leu Pro Leu Pro Trp Thr Ser Gly Ala Thr Thr
    210                 215                 220

Glu Thr Pro Thr Trp Asn Arg Lys Glu Leu Leu Val Thr Phe Lys Asn
225                 230                 235                 240

Ala His Ala Lys Lys Gln Glu Val Val Val Leu Gly Ser Gln Glu Gly
                245                 250                 255

Ala Met His Thr Ala Leu Thr Gly Ala Thr Glu Ile Gln Asn Ser Gly
            260                 265                 270

Gly Thr Ser Ile Phe Ala Gly His Leu Lys Cys Arg Leu Lys Met Asp
        275                 280                 285

Lys Leu Glu Leu Lys Gly Met Ser Tyr Ala Met Cys Thr Asn Thr Phe
    290                 295                 300

Val Leu Lys Lys Glu Val Ser Glu Thr Gln His Gly Thr Ile Leu Ile
305                 310                 315                 320

Lys Val Glu Tyr Lys Gly Glu Asp Ala Pro Cys Lys Ile Pro Phe Ser
                325                 330                 335

Thr Glu Asp Gly Gln Gly Lys Ala His Asn Gly Arg Leu Ile Thr Ala
            340                 345                 350

Asn Pro Val Thr Lys Lys Glu Pro Val Asn Ile Glu Ala Glu
           355                 360             365

Pro Pro Phe Gly Glu Ser Asn Ile Val Ile Gly Ile Gly Asp Asn Ala
370                 375                 380

Leu Lys Ile Asn Trp Tyr Lys Lys Gly Ser Ser Ile Gly Lys Met Phe
385                 390                 395                 400

Glu Ala Thr Ala Arg Gly Ala Arg Arg Met
                405             410

<210> SEQ ID NO 18
<211> LENGTH: 410
<212> TYPE: PRT
<213> ORGANISM: Dengue virus

<400> SEQUENCE: 18

Met Arg Cys Val Gly Ile Gly Asn Arg Asp Phe Val Glu Gly Leu Ser
1               5                   10                  15

Gly Ala Thr Trp Val Asp Val Val Leu Glu His Gly Ser Cys Val Thr
            20                  25                  30

Thr Met Ala Lys Asp Lys Pro Thr Leu Asp Ile Glu Leu Leu Lys Thr
        35                  40                  45

Glu Val Thr Asn Pro Ala Val Leu Arg Lys Leu Cys Ile Glu Ala Lys
50                  55                  60

Ile Ser Asn Thr Thr Thr Asp Ser Arg Cys Pro Thr Gln Gly Glu Ala
65                  70                  75                  80

Thr Leu Val Glu Glu Gln Asp Thr Asn Phe Val Cys Arg Arg Thr Phe
                85                  90                  95

Val Asp Arg Gly Trp Gly Asn Gly Cys Gly Leu Phe Gly Lys Gly Ser
            100                 105                 110

Leu Ile Thr Cys Ala Lys Phe Lys Cys Val Thr Lys Leu Glu Gly Lys
        115                 120                 125

Ile Val Gln Tyr Glu Asn Leu Lys Tyr Ser Val Ile Val Thr Val His
130                 135                 140

Thr Gly Asp Gln His Gln Val Gly Asn Glu Thr Thr Glu His Gly Thr
145                 150                 155                 160

Thr Ala Thr Ile Thr Pro Gln Ala Pro Thr Ser Glu Ile Gln Leu Thr
                165                 170                 175

Asp Tyr Gly Ala Leu Thr Leu Asp Cys Ser Pro Arg Thr Gly Leu Asp
            180                 185                 190

Phe Asn Glu Met Val Leu Leu Thr Met Glu Lys Lys Ser Trp Leu Val
        195                 200                 205

His Lys Gln Trp Phe Leu Asp Leu Pro Leu Pro Trp Thr Ser Gly Ala
210                 215                 220

Ser Thr Ser Gln Glu Thr Trp Asn Arg Gln Asp Leu Leu Val Thr Phe
225                 230                 235                 240

Lys Thr Ala His Ala Lys Lys Gln Glu Val Val Val Leu Gly Ser Gln
                245                 250                 255

Glu Gly Ala Met His Thr Ala Leu Thr Gly Ala Thr Glu Ile Gln Thr
            260                 265                 270

Ser Gly Thr Thr Thr Ile Phe Ala Gly His Leu Lys Cys Arg Leu Lys
        275                 280                 285

Met Asp Lys Leu Thr Leu Lys Gly Met Ser Tyr Val Met Cys Thr Gly
290                 295                 300

Ser Phe Lys Leu Glu Lys Glu Val Ala Glu Thr Gln His Gly Thr Val
305                 310                 315                 320

```
Leu Val Gln Val Lys Tyr Glu Gly Thr Asp Ala Pro Cys Lys Ile Pro
                325                 330                 335

Phe Ser Ser Gln Asp Glu Lys Gly Val Thr Gln Asn Gly Arg Leu Ile
            340                 345                 350

Thr Ala Asn Pro Ile Val Thr Asp Lys Glu Lys Pro Val Asn Ile Glu
        355                 360                 365

Ala Glu Pro Pro Phe Gly Glu Ser Tyr Ile Val Val Gly Ala Gly Glu
    370                 375                 380

Lys Ala Leu Lys Leu Ser Trp Phe Lys Lys Gly Ser Ser Ile Gly Lys
385                 390                 395                 400

Met Phe Glu Ala Thr Ala Arg Gly Ala Arg
                405                 410

<210> SEQ ID NO 19
<211> LENGTH: 410
<212> TYPE: PRT
<213> ORGANISM: Dengue virus

<400> SEQUENCE: 19

Met Arg Cys Val Gly Val Gly Asn Arg Asp Phe Val Glu Gly Val Ser
1               5                   10                  15

Gly Gly Ala Trp Val Asp Leu Val Leu Glu His Gly Gly Cys Val Thr
            20                  25                  30

Thr Met Ala Gln Gly Lys Pro Thr Leu Asp Phe Glu Leu Thr Lys Thr
        35                  40                  45

Thr Ala Lys Glu Val Ala Leu Leu Arg Thr Tyr Cys Ile Glu Ala Ser
    50                  55                  60

Ile Ser Asn Ile Thr Thr Ala Thr Arg Cys Pro Thr Gln Gly Glu Pro
65                  70                  75                  80

Tyr Leu Lys Glu Glu Gln Asp Gln Gln Tyr Ile Cys Arg Arg Asp Val
                85                  90                  95

Val Asp Arg Gly Trp Gly Asn Gly Cys Gly Leu Phe Gly Lys Gly Gly
            100                 105                 110

Val Val Thr Cys Ala Lys Phe Ser Cys Ser Gly Lys Ile Thr Gly Asn
        115                 120                 125

Leu Val Gln Ile Glu Asn Leu Glu Tyr Thr Val Val Val Thr Val His
    130                 135                 140

Asn Gly Asp Thr His Ala Val Gly Asn Asp Thr Ser Asn His Gly Val
145                 150                 155                 160

Thr Ala Thr Ile Thr Pro Arg Ser Pro Ser Val Glu Val Lys Leu Pro
                165                 170                 175

Asp Tyr Gly Glu Leu Thr Leu Asp Cys Glu Pro Arg Ser Gly Ile Asp
            180                 185                 190

Phe Asn Glu Met Ile Leu Met Lys Met Lys Lys Thr Trp Leu Val
        195                 200                 205

His Lys Gln Trp Phe Leu Asp Leu Pro Leu Pro Trp Thr Ala Gly Ala
    210                 215                 220

Asp Thr Ser Glu Val His Trp Asn Tyr Lys Glu Arg Met Val Thr Phe
225                 230                 235                 240

Lys Val Pro His Ala Lys Arg Gln Asp Val Thr Val Leu Gly Ser Gln
                245                 250                 255

Glu Gly Ala Met His Ser Ala Leu Ala Gly Ala Thr Glu Val Asp Ser
            260                 265                 270

Gly Asp Gly Asn His Met Phe Ala Gly His Leu Lys Cys Lys Val Arg
```

```
                    275                 280                 285
Met Glu Lys Leu Arg Ile Lys Gly Met Ser Tyr Thr Met Cys Ser Gly
    290                 295                 300
Lys Phe Ser Ile Asp Lys Glu Met Ala Glu Thr Gln His Gly Thr Thr
305                 310                 315                 320
Val Val Lys Val Lys Tyr Glu Gly Ala Gly Ala Pro Cys Lys Val Pro
                325                 330                 335
Ile Glu Ile Arg Asp Val Asn Lys Glu Lys Val Val Gly Arg Val Ile
                340                 345                 350
Ser Ser Thr Pro Leu Ala Glu Asn Thr Asn Ser Val Thr Asn Ile Glu
                355                 360                 365
Leu Glu Pro Pro Phe Gly Asp Ser Tyr Ile Val Ile Gly Val Gly Asn
    370                 375                 380
Ser Ala Leu Thr Leu His Trp Phe Arg Lys Gly Ser Ser Ile Gly Lys
385                 390                 395                 400
Met Phe Glu Ser Thr Tyr Arg Gly Ala Lys
                405                 410

<210> SEQ ID NO 20
<211> LENGTH: 410
<212> TYPE: PRT
<213> ORGANISM: Dengue virus

<400> SEQUENCE: 20

Met Arg Cys Ile Gly Ile Ser Asn Arg Asp Phe Val Glu Gly Val Ser
1               5                   10                  15
Gly Gly Ser Trp Val Asp Ile Val Leu Glu His Gly Ser Cys Val Thr
                20                  25                  30
Thr Met Ala Lys Asn Lys Pro Thr Leu Asp Phe Glu Leu Ile Lys Thr
            35                  40                  45
Glu Ala Lys Gln Pro Ala Thr Leu Arg Lys Tyr Cys Ile Glu Ala Lys
        50                  55                  60
Leu Thr Asn Thr Thr Thr Glu Ser Arg Cys Pro Thr Gln Gly Glu Pro
65                  70                  75                  80
Ser Leu Asn Glu Glu Gln Asp Lys Arg Phe Val Cys Lys His Ser Met
                85                  90                  95
Val Asp Arg Gly Trp Gly Asn Gly Cys Gly Leu Phe Gly Lys Gly Gly
                100                 105                 110
Ile Val Thr Cys Ala Met Phe Thr Cys Lys Lys Asn Met Glu Gly Lys
            115                 120                 125
Val Val Gln Pro Glu Asn Leu Glu Tyr Thr Ile Val Val Thr Pro His
        130                 135                 140
Ser Gly Glu Glu His Ala Val Gly Asn Asp Thr Gly Lys His Gly Lys
145                 150                 155                 160
Glu Ile Lys Val Thr Pro Gln Ser Ser Ile Thr Glu Ala Glu Leu Thr
                165                 170                 175
Gly Tyr Gly Thr Val Thr Met Glu Cys Ser Pro Arg Thr Gly Leu Asp
                180                 185                 190
Phe Asn Glu Met Val Leu Leu Gln Met Glu Asn Lys Ala Trp Leu Val
            195                 200                 205
His Arg Gln Trp Phe Leu Asp Leu Pro Leu Pro Trp Leu Pro Gly Ala
        210                 215                 220
Asp Thr Gln Gly Ser Asn Trp Ile Gln Lys Glu Thr Leu Val Thr Phe
225                 230                 235                 240
```

```
Lys Asn Pro His Ala Lys Lys Gln Asp Val Val Leu Gly Ser Gln
            245                 250                 255

Glu Gly Ala Met His Thr Ala Leu Thr Gly Ala Thr Glu Ile Gln Met
        260                 265                 270

Ser Ser Gly Asn Leu Leu Phe Thr Gly His Leu Lys Cys Arg Leu Arg
        275                 280                 285

Met Asp Lys Leu Gln Leu Lys Gly Met Ser Tyr Ser Met Cys Thr Gly
        290                 295                 300

Lys Phe Lys Val Val Lys Glu Ile Ala Glu Thr Gln His Gly Thr Ile
305                 310                 315                 320

Val Ile Arg Val Gln Tyr Glu Gly Asp Gly Ser Pro Cys Lys Ile Pro
            325                 330                 335

Phe Glu Ile Met Asp Leu Glu Lys Arg His Val Leu Gly Arg Leu Ile
            340                 345                 350

Thr Val Asn Pro Ile Val Thr Glu Lys Asp Ser Pro Val Asn Ile Glu
            355                 360                 365

Ala Glu Pro Pro Phe Gly Asp Ser Tyr Ile Ile Gly Val Asp Pro
        370                 375                 380

Gly Gln Leu Lys Leu Asn Trp Phe Lys Lys Gly Ser Ser Ile Gly Gln
385                 390                 395                 400

Met Phe Glu Thr Thr Met Arg Gly Ala Lys
            405                 410

<210> SEQ ID NO 21
<211> LENGTH: 410
<212> TYPE: PRT
<213> ORGANISM: Yellow fever virus

<400> SEQUENCE: 21

Ala His Cys Ile Gly Ile Thr Asp Arg Asp Phe Ile Glu Gly Val His
1               5                   10                  15

Gly Gly Thr Trp Val Ser Ala Thr Leu Glu Gln Asp Lys Cys Val Thr
            20                  25                  30

Val Met Ala Pro Asp Lys Pro Ser Leu Asp Ile Ser Leu Glu Thr Val
        35                  40                  45

Ala Ile Asp Arg Pro Ala Glu Val Arg Lys Val Cys Tyr Asn Ala Val
    50                  55                  60

Leu Thr His Val Lys Ile Asn Asp Lys Cys Pro Ser Thr Gly Glu Ala
65                  70                  75                  80

His Leu Ala Glu Glu Asn Glu Gly Asp Asn Ala Cys Lys Arg Thr Tyr
                85                  90                  95

Ser Asp Arg Gly Trp Gly Asn Gly Cys Gly Leu Phe Gly Lys Gly Ser
            100                 105                 110

Ile Val Ala Cys Ala Lys Phe Thr Cys Ala Lys Ser Met Ser Leu Phe
        115                 120                 125

Glu Val Asp Gln Thr Lys Ile Gln Tyr Val Ile Arg Ala Gln Leu His
    130                 135                 140

Val Gly Ala Lys Gln Glu Asn Trp Thr Thr Asp Ile Lys Thr Leu Lys
145                 150                 155                 160

Phe Asp Ala Leu Ser Gly Ser Gln Glu Val Glu Phe Ile Gly Tyr Gly
                165                 170                 175

Lys Ala Thr Leu Glu Cys Gln Val Gln Thr Ala Val Asp Phe Gly Asn
            180                 185                 190

Ser Tyr Ile Ala Glu Met Glu Thr Glu Ser Trp Ile Val Asp Arg Gln
        195                 200                 205
```

Trp Ala Gln Asp Leu Thr Leu Pro Trp Gln Ser Gly Ser Gly Gly Val
210                 215                 220

Trp Arg Glu Met His His Leu Val Glu Phe Glu Pro Pro His Ala Ala
225                 230                 235                 240

Thr Ile Arg Val Leu Ala Leu Gly Asn Gln Glu Gly Ser Leu Lys Thr
            245                 250                 255

Ala Leu Thr Gly Ala Met Arg Val Thr Lys Asp Thr Asn Asp Asn Asn
            260                 265                 270

Leu Tyr Lys Leu His Gly Gly His Val Ser Cys Arg Val Lys Leu Ser
        275                 280                 285

Ala Leu Thr Leu Lys Gly Thr Ser Tyr Lys Ile Cys Thr Asp Lys Met
        290                 295                 300

Phe Phe Val Lys Asn Pro Thr Asp Thr Gly His Gly Thr Val Val Met
305                 310                 315                 320

Gln Val Lys Val Ser Lys Gly Ala Pro Cys Arg Ile Pro Val Ile Val
                325                 330                 335

Ala Asp Asp Leu Thr Ala Ala Ile Asn Lys Gly Ile Leu Val Thr Val
            340                 345                 350

Asn Pro Ile Ala Ser Thr Asn Asp Asp Glu Val Leu Ile Glu Val Asn
            355                 360                 365

Pro Pro Phe Gly Asp Ser Tyr Ile Ile Val Gly Arg Gly Asp Ser Arg
370                 375                 380

Leu Thr Tyr Gln Trp His Lys Glu Gly Ser Ser Ile Gly Lys Leu Phe
385                 390                 395                 400

Thr Gln Thr Met Lys Gly Val Glu Arg Leu
                405                 410

<210> SEQ ID NO 22
<211> LENGTH: 410
<212> TYPE: PRT
<213> ORGANISM: Japanese encephalitis virus

<400> SEQUENCE: 22

Phe Asn Cys Leu Gly Met Gly Asn Arg Asp Phe Ile Glu Gly Ala Ser
1               5                   10                  15

Gly Ala Thr Trp Val Asp Leu Val Leu Glu Gly Asp Ser Cys Leu Thr
            20                  25                  30

Ile Met Ala Asn Asp Lys Pro Thr Leu Asp Val Arg Met Ile Asn Ile
        35                  40                  45

Glu Ala Ser Gln Leu Ala Glu Val Arg Ser Tyr Cys Tyr His Ala Ser
    50                  55                  60

Val Thr Asp Ile Ser Thr Val Ala Arg Cys Pro Thr Thr Gly Glu Ala
65                  70                  75                  80

His Asn Glu Lys Arg Ala Asp Ser Ser Tyr Val Cys Lys Gln Gly Phe
                85                  90                  95

Thr Asp Arg Gly Trp Gly Asn Gly Cys Gly Leu Phe Gly Lys Gly Ser
            100                 105                 110

Ile Asp Thr Cys Ala Lys Phe Ser Cys Thr Ser Lys Ala Ile Gly Arg
        115                 120                 125

Thr Ile Gln Pro Glu Asn Ile Lys Tyr Glu Val Gly Ile Phe Val His
    130                 135                 140

Gly Thr Thr Thr Ser Glu Asn His Gly Asn Tyr Ser Ala Gln Val Gly
145                 150                 155                 160

Ala Ser Gln Ala Ala Lys Phe Thr Val Thr Pro Asn Ala Pro Ser Ile

```
                 165                 170                 175
Thr Leu Lys Leu Gly Asp Tyr Gly Glu Val Thr Leu Asp Cys Glu Pro
            180                 185                 190

Arg Ser Gly Leu Asn Thr Glu Ala Phe Tyr Val Met Thr Val Gly Ser
        195                 200                 205

Lys Ser Phe Leu Val His Arg Glu Trp Phe His Asp Leu Ala Leu Pro
    210                 215                 220

Trp Thr Ser Pro Ser Thr Ala Trp Arg Asn Arg Glu Leu Leu Met
225                 230                 235                 240

Glu Phe Glu Glu Ala His Ala Thr Lys Gln Ser Val Val Ala Leu Gly
                245                 250                 255

Ser Gln Glu Gly Gly Leu His Gln Ala Leu Ala Gly Ala Ile Val Val
            260                 265                 270

Glu Tyr Ser Ser Ser Val Lys Leu Thr Ser Gly His Leu Lys Cys Arg
        275                 280                 285

Leu Lys Met Asp Lys Leu Ala Leu Lys Gly Thr Thr Tyr Gly Met Cys
    290                 295                 300

Thr Glu Lys Phe Ser Phe Ala Lys Asn Pro Ala Asp Thr Gly His Gly
305                 310                 315                 320

Thr Val Val Ile Glu Leu Ser Tyr Ser Gly Ser Asp Gly Pro Cys Lys
                325                 330                 335

Ile Pro Ile Val Ser Val Ala Ser Leu Asn Asp Met Thr Pro Val Gly
            340                 345                 350

Arg Leu Val Thr Val Asn Pro Phe Val Ala Thr Ser Ser Ala Asn Ser
        355                 360                 365

Lys Val Leu Val Glu Met Glu Pro Pro Phe Gly Asp Ser Tyr Ile Val
    370                 375                 380

Val Gly Arg Gly Asp Lys Gln Ile Asn His His Trp His Lys Ala Gly
385                 390                 395                 400

Ser Thr Leu Gly Lys Ala Phe Ser Thr Thr
                405                 410
```